United States Patent [19]

Boon et al.

[11] Patent Number: 5,925,729
[45] Date of Patent: Jul. 20, 1999

[54] TUMOR REJECTION ANTIGEN PRECURSORS, TUMOR REJECTION ANTIGENS AND USES THEREOF

[75] Inventors: Thierry Boon; Pierre Van Der Bruggen; Benoit Van Den Eynde; Aline Van Pel; Etienne De Plaen; Christophe Lurquin; Patrick Chomez, all of Brussels, Belgium; Catia Traversari, Milan, Italy

[73] Assignee: Ludwig Institute for Cancer Research, New York, N.Y.

[21] Appl. No.: 08/142,368

[22] Filed: May 2, 1994

Related U.S. Application Data

[63] Continuation-in-part of application No. 07/807,043, Dec. 12, 1991, Pat. No. 5,342,774, which is a continuation-in-part of application No. 07/764,365, Sep. 23, 1991, abandoned, which is a continuation-in-part of application No. 07/728,838, Jul. 9, 1991, abandoned, which is a continuation-in-part of application No. 07/705,702, May 23, 1991, abandoned.

[51] Int. Cl.⁶ .............................. C07K 7/06; A61K 38/08

[52] U.S. Cl. ..................... 530/328; 424/185.1; 514/15; 530/395; 530/806; 530/828

[58] Field of Search ................................. 530/300, 350, 530/868, 806, 828, 395, 328; 424/184.1, 185.1; 514/15

[56] References Cited

U.S. PATENT DOCUMENTS

| | | | |
|---|---|---|---|
| 5,342,774 | 8/1994 | Boon et al. ........................ | 435/240.2 |
| 5,405,940 | 4/1995 | Boon et al. ........................ | 530/328 |
| 5,462,871 | 10/1995 | Boon-Falleur et al. ............ | 435/240.2 |

*Primary Examiner*—Thomas M. Cunningham
*Attorney, Agent, or Firm*—Felfe & Lynch

[57] ABSTRACT

The invention relates to an isolated DNA sequence which codes for an antigen expressed by tumor cells which is recognized by cytotoxic T cells, leading to lysis of the tumor which expresses it. Also described are cells transfected by the DNA sequence, and various therapeutic and diagnostic uses arising out of the properties of the DNA and the antigen for which it codes.

1 Claim, 14 Drawing Sheets

FIG. 9

```
MAGE-3  III  CCTCCCCAGAGTCCTCAGGGAGCCTCCagCcTcCCCACTACCATgAACTaCcCTCtctgGAGcCAAtCCtaTGAGgacTCCAGCAaCCaaGAAGAGGAGG
                                                                                        CHO-3
MAGE-2  II   CCTCCCCAcAGTCCTCAGGGAGCCTCCagCTTctCgACTACCATCAACTaCACTCTttgGAGaCAAtCCgaTGAGGgCTCCAGCAaCCaaGAAGAGGAGG
                                                                                        CHO-2
MAGE-1  I    CCTCCCCAGAGTCCTCAGGGAGCCTCCGCCTTTCCCACTACCATCAACTTCACTGACACAGAGGCAACCAGTGAGGGTTCCAGCAGCCGTGAAGAGGAGG
             225   CHO-8

III  GGCCAAGCACCTtcccTgaCC-TGGAGTCCgaGTTCCaAGCAcACTCAgTAGgAAGGTGGCcGAgTTGGTTcaTTTTCTGCTCCTCAAgTATcGAGCCA
        II   GGCCAAGaatgTtTcccgaCCTtGGAGTCCGAGTTCCaAGCAcAATCAgTAGgAAGaTGGtTGAgTTGGTTcaTTTTCTGCTCCTCAAgTATcGAGCCA
        I    GGCCAAGCACCTCTTGTATCC-TGGAGTCCTTGTTCCGAGCAGTAATCACTAAGAAGGTGGCTGATTTGGTTTCTGCTCCTCAAATATCGAGCCA
             325

III  GGGAGCCggTCACAAAGGCAGAAATGCTGggGAGTGTGCgTCggAAATTggcCAGTATTcTTTTCCTGtGATCTTCAGCAAAGCTtCcagtTCCTTGCAGCT
        II   GGGAGCCggTCACAAAGGCAGAAATGCTGGAGAGTGTCCTCAgAAATTgCCAGgACTtcTTTCCgtGATCTTCAGCAAAGCCTCcGAgTaCTTGCAGCT
        I    GGGAGCCAGTCACAAAGGCAGAAATGCTGGAGAGTGTCATCAAAAATTACAAGCACTGTTTCCTGAGATCTTCGGCAAAGCCTCTGAGTCCTTGCAGCT
             425                                                                                SEQ-4

III  GGTCTTTTGGCATcGAgcTGAtGGAAGtgACCCCAtCGGCCACTtgTAcaTCtTTGCCACCTGCCTGCTCCTAcGATGGCCTGCTGGGTGACAAT
        II   GGTCTTTTGGCATcGAgGTGgtGGAAGtgGtCCCCAtCAgCCACTtgTAcaTCCTTGTCACCTGCCTGGCCTCCTAcGATGGCCTGCTGGGCGACAAT
        I    GGTCTTTTGGCATTGACGTGAAGGAAGCAGACCCCACCGGCCACTCCCATGTCCTTGTCACCTGCCTGCCTAGTCTCTCCTATGATGGCCTGCTGGGTGATAAT
             525

III  CAGATCATGCCCAAGgCAGGCcTCCTGGCcATaATcGTCCTTGATAATcGTCCTGATAATcGCCAAgaGAGGGCGaCtGTGCcCCTGAGGAGAAATCTGGGAGGAGCTGAGTG
        II   CAGgTCATGCCCAAGAGACAGGCcTCCTGGCcATaATcGTCCTGATAATcGTC-TGGcCATaATcGCCAATaGAGGGCGaCtGTGCCCCTGAGGAGAAATCTGGGcGACAGCTGAGTa
        I    CAGATCATGCCCAAGACAGGCTTCCTGGTCTTGATAATTGTCCTGATAATTGTCCTTCCTGATATTGAGATTGCAATGAGGGCGGCCATGCTCCTGAGGAGGAATCTGGGAGGAGCTGAGTG
             625                                                                                                               CHO-9
```

FIG. 11A

| | | Northern blot probed with cross-reactive MAGE-1 probe* | EXPRSSION OF MAGE GENE FAMILY cDNA-PCR product probed with oligonucleotide specific for: | | | RECOGNITION BY ANTI-E CTL tested by: | | Expression of antigen MZ2-E after transfection** |
|---|---|---|---|---|---|---|---|---|
| | | | MAGE-1 | MAGE-2 | MAGE-3† | TNF release‡ | Lysis§ | |
| Cells of patient MZ2 | melanoma cell line MZ2-MEL.3.0 | + | +++ | +++ | +++ | + | + | |
| | tumor sample MZ2 (1982) | + | +++ | +++ | +++ | | | |
| | antigen-loss variant MZ2-MEL.2.2 | + | – | +++ | +++ | – | – | |
| | CTL clone MZ2-CTL.82/30 | – | – | – | – | | | |
| | PHA-activated blood lymphocytes | – | – | – | – | | | |
| Normal tissues | Liver | – | – | – | – | | | |
| | Muscle | – | – | – | – | | | |
| | Skin | – | – | – | – | | | |
| | Lung | – | – | – | – | | | |
| | Brain | – | – | – | – | | | |
| | Kidney | – | – | – | – | | | |
| Melanoma cell lines of HLA-A1 patients | LB34-MEL | + | ++ | +++ | +++ | + | +– | |
| | MI665/2-MEL | – | – | – | – | – | – | |
| | MI10221-MEL | + | – | ++ | +++ | + | – | ++ |
| | MI13443-MEL | + | +++ | +++ | +++ | + | + | |
| | SK33-MEL | + | – | +++ | +++ | – | – | – |
| | SK23-MEL | + | – | +++ | +++ | – | – | + |

* Data obtained in the conditions of figure 5.
† Data obtained as described in figure 6.
‡ TNF release by CTL 82/30 after stimulation with the tumor cells as described in (11).
§ Lysis of 51 Cr labelled target by CTL 82/30 in the conditions of figure 1.
** Cells transfected with the 2.4 kb fragment of gene MAGE-1 were tested for their ability to stimulate TNF release by CTL 82/30

FIG. 11B

EXPRESSION OF MAGE GENE FAMILY / RECOGNITION BY ANTI-E CTL

| | | Northern blot probed with cross-reactive MAGE-1 probe* | cDNA-PCR product probed with oligonucleotide specific for: | | | TNF release‡ | Lysis§ | Expression of antigen MZ2-E after transfection** |
|---|---|---|---|---|---|---|---|---|
| | | | MAGE-1 | MAGE-2 | MAGE-3† | | | |
| Melanoma cell lines of other patients | LB17-MEL | + | + | +++ | +++ | − | − | − |
| | LB33-MEL | + | − | +++ | +++ | − | − | − |
| | LB4-MEL | − | − | − | − | − | − | |
| | LB41-MEL | − | − | − | − | − | − | |
| | MI4024-MEL | + | +++ | +++ | +++ | − | − | |
| | SK29-MEL | − | − | − | − | − | − | |
| | MZ3-MEL | + | + | +++ | +++ | − | − | |
| | MZ5-MEL | + | − | +++ | +++ | − | − | |
| Melanoma tumor sample | BB5-MEL | + | +++ | ++ | +++ | − | − | |
| Other tumor cell lines | small cell lung cancer H209 | + | − | +++ | +++ | − | − | |
| | small cell lung cancer H345 | + | − | +++ | +++ | − | − | |
| | small cell lung cancer H510 | + | − | +++ | +++ | − | − | |
| | small cell lung cancer LB11 | + | + | +++ | +++ | − | − | |
| | bronchial squamous cell carcinoma LB37 | + | − | − | − | − | − | |
| | thyroid medullary carcinoma TT | + | +++ | +++ | +++ | − | − | |
| | colon carcinoma LB31 | + | − | +++ | +++ | − | − | |
| | colon carcinoma LS411 | − | − | − | − | − | | |
| Other tumor samples | chronic myeloid leukemia LLC5 | − | − | − | − | | | |
| | acute myeloid leukemia TA | − | − | − | − | | | |

\* Data obtained in the conditions of figure 5.
† Data obtained as described in figure 6.
‡ TNF release by CTL 82/30 after stimulation with the tumor cells as described in figure 1.
§ Lysis of 51 Cr labelled target by CTL 82/30 in the conditions of figure 1.
\*\* Cells transfected with the 2.4 kb fragment of gene MAGE-1 were tested for their ability to stimulate TNF release by CTL 82/30

```
                           SEQUENCE LISTING (1) GENERAL INFORMATION:

(iii) NUMBER OF SEQUENCES:  26

(2) INFORMATION FOR SEQ ID NO: 1:

(i) SEQUENCE CHARACTERISTICS:
        (A) LENGTH:  462 base pairs
        (B) TYPE:  nucleic acid
        (C) STRANDEDNESS:  single
        (D) TOPOLOGY:  linear (ii) MOLECULE TYPE:  genomic DNA (xi) SEQUENCE DESCRIPTION:  SEQ ID NO: 1:

ACCACAGGAG AATGAAAAGA ACCCGGGACT CCCAAAGACG CTAGATGTGT GAAGATCCTG         60

ATCACTCATT GGGTGTCTGA GTTCTGCGAT ATTCATCCCT CAGCCAATGA GCTTACTGTT       120

CTCGTGGGGG GTTTGTGAGC CTTGGGTAGG AAGTTTTGCA AGTTCCGCCT ACAGCTCTAG       180

CTTGTGAATT TGTACCCTTT CACGTAAAAA AGTAGTCCAG AGTTTACTAC ACCCTCCCTC       240

CCCCCTCCCA CCTCGTGCTG TGCTGAGTTT AGAAGTCTTC CTTATAGAAG TCTTCCGTAT       300

AGAACTCTTC CGGAGGAAGG AGGGAGGACC CCCCCCCTTT GCTCTCCCAG CATGCATTGT       360

GTCAACGCCA TTGCACTGAG CTGGTCGAAG AAGTAAGCCG CTAGCTTGCG ACTCTACTCT       420

TATCTTAACT TAGCTCGGCT TCCTGCTGGT ACCCTTTGTG CC                         462

(2) INFORMATION FOR SEQ ID NO: 2:
```

(i) SEQUENCE CHARACTERISTICS:
    (A) LENGTH: 675 base pairs
    (B) TYPE: nucleic acid
    (C) STRANDEDNESS: single
    (D) TOPOLOGY: linear (ii) MOLECULE TYPE: genomic DNA (xi) SEQUENCE DESCRIPTION: SEQ ID NO: 2:

| | | | | | | | | | | | | | | | | |
|---|---|---|---|---|---|---|---|---|---|---|---|---|---|---|---|---|
| ATG | TCT | GAT | AAC | AAG | AAA | CCA | GAC | AAA | GCC | CAC | AGT | GGC | TCA | GGT | GGT | 48 |
| Met | Ser | Asp | Asn | Lys | Lys | Pro | Asp | Lys | Ala | His | Ser | Gly | Ser | Gly | Gly | |
| | | | | 5 | | | | 10 | | | | | 15 | | | |
| GAC | GGT | GAT | GGG | AAT | AGG | TGC | AAT | TTA | TTG | CAC | CGG | TAC | TCC | CTG | GAA | 96 |
| Asp | Gly | Asp | Gly | Asn | Arg | Cys | Asn | Leu | Leu | His | Arg | Tyr | Ser | Leu | Glu | |
| | | | | 20 | | | | 25 | | | | | 30 | | | |
| GAA | ATT | CTG | CCT | TAT | CTA | GGG | TGG | CTG | GTC | TTC | GCT | GTT | GTC | ACA | ACA | 144 |
| Glu | Ile | Leu | Pro | Tyr | Leu | Gly | Trp | Leu | Val | Phe | Ala | Val | Val | Thr | Thr | |
| | | | | 35 | | | | 40 | | | | | 45 | | | |
| AGT | TTT | CTG | GCG | CTC | CAG | ATG | TTC | ATA | GAC | GCC | CTT | TAT | GAG | GAG | CAG | 192 |
| Ser | Phe | Leu | Ala | Leu | Gln | Met | Phe | Ile | Asp | Ala | Leu | Tyr | Glu | Glu | Gln | |
| | | | | 50 | | | | 55 | | | | | 60 | | | |
| TAT | GAA | AGG | GAT | GTG | GCC | TGG | ATA | GCC | AGG | CAA | AGC | AAG | CGC | ATG | TCC | 240 |
| Tyr | Glu | Arg | Asp | Val | Ala | Trp | Ile | Ala | Arg | Gln | Ser | Lys | Arg | Met | Ser | |
| 65 | | | | 70 | | | | 75 | | | | | 80 | | | |
| TCT | GTC | GAT | GAG | GAT | GAA | GAC | GAT | GAG | GAT | GAT | GAG | GAT | GAC | TAC | TAC | 288 |
| Ser | Val | Asp | Glu | Asp | Glu | Asp | Asp | Glu | Asp | Asp | Glu | Asp | Asp | Tyr | Tyr | |
| | | | | 85 | | | | 90 | | | | | 95 | | | |
| GAC | GAC | GAG | GAC | GAC | GAC | GAC | GAT | GCC | TTC | TAT | GAT | GAT | GAG | GAT | GAT | 336 |
| Asp | Asp | Glu | Asp | Asp | Asp | Asp | Asp | Ala | Phe | Tyr | Asp | Asp | Glu | Asp | Asp | |
| | | | | 100 | | | | 105 | | | | | 110 | | | |
| GAG | GAA | GAA | GAA | TTG | GAG | AAC | CTG | ATG | GAT | GAT | GAA | TCA | GAA | GAT | GAG | 384 |
| Glu | Glu | Glu | Glu | Leu | Glu | Asn | Leu | Met | Asp | Asp | Glu | Ser | Glu | Asp | Glu | |
| | | | | 115 | | | | 120 | | | | | 125 | | | |
| GCC | GAA | GAA | GAG | ATG | AGC | GTG | GAA | ATG | GGT | GCC | GGA | GCT | GAG | GAA | ATG | 432 |
| Ala | Glu | Glu | Glu | Met | Ser | Val | Glu | Met | Gly | Ala | Gly | Ala | Glu | Glu | Met | |
| | | | | 130 | | | | 135 | | | | | 140 | | | |
| GGT | GCT | GGC | GCT | AAC | TGT | GCC | TGT | GTT | CCT | GGC | CAT | CAT | TTA | AGG | AAG | 480 |
| Gly | Ala | Gly | Ala | Asn | Cys | Ala | Cys | Val | Pro | Gly | His | His | Leu | Arg | Lys | |
| 145 | | | | 150 | | | | 155 | | | | | 160 | | | |
| AAT | GAA | GTG | AAG | TGT | AGG | ATG | ATT | TAT | TTC | TTC | CAC | GAC | CCT | AAT | TTC | 528 |
| Asn | Glu | Val | Lys | Cys | Arg | Met | Ile | Tyr | Phe | Phe | His | Asp | Pro | Asn | Phe | |
| | | | | 165 | | | | 170 | | | | | 175 | | | |
| CTG | GTG | TCT | ATA | CCA | GTG | AAC | CCT | AAG | GAA | CAA | ATG | GAG | TGT | AGG | TGT | 576 |
| Leu | Val | Ser | Ile | Pro | Val | Asn | Pro | Lys | Glu | Gln | Met | Glu | Cys | Arg | Cys | |
| | | | | 180 | | | | 185 | | | | | 190 | | | |
| GAA | AAT | GCT | GAT | GAA | GAG | GTT | GCA | ATG | GAA | GAG | GAA | GAA | GAA | GAA | GAG | 624 |
| Glu | Asn | Ala | Asp | Glu | Glu | Val | Ala | Met | Glu | Glu | Glu | Glu | Glu | Glu | Glu | |
| | | | | 195 | | | | 200 | | | | | 210 | | | |
| GAG | GAG | GAG | GAG | GAA | GAG | GAA | ATG | GGA | AAC | CCG | GAT | GGC | TTC | TCA | CCT | 672 |
| Glu | Glu | Glu | Glu | Glu | Glu | Glu | Met | Gly | Asn | Pro | Asp | Gly | Phe | Ser | Pro | |
| 220 | | | | | 225 | | | | 230 | | | | | 235 | | |
| TAG | | | | | | | | | | | | | | | | 675 |

(2) INFORMATION FOR SEQ ID NO: 3:

(i) SEQUENCE CHARACTERISTICS:
    (A) LENGTH: 228 base pairs
    (B) TYPE: nucleic acid
    (C) STRANDEDNESS: single
    (D) TOPOLOGY: linear (ii) MOLECULE TYPE: genomic DNA (xi) SEQUENCE DESCRIPTION: SEQ ID NO: 3:

```
GCATGCAGTT GCAAAGCCCA AAGAAAGAA ATGGACAGCG GAAGAAGTGG TTGTTTTTTT        60
```

```
GCATGCAGTT GCAAAGCCCA GAAGAAAGAA ATGGACAGCG GAAGAAGTGG TTGTTTTTTT        60
TTCCCCTTCA TTAATTTTCT AGTTTTTAGT AATCCAGAAA ATTTGATTTT GTTCTAAAGT       120
TCATTATGCA AAGATGTCAC CAACAGACTT CTGACTGCAT GGTGAACTTT CATATGATAC       180
ATAGGATTAC ACTTGTACCT GTTAAAAATA AAGTTTGAC TTGCATAC                    228
```

(2) INFORMATION FOR SEQ ID NO: 4:

(i) SEQUENCE CHARACTERISTICS:
        (A) LENGTH: 1365 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 4:

```
ACCACAGGAG AATGAAAAGA ACCCGGGACT CCCAAAGACG CTAGATGTGT                   50
GAAGATCCTG ATCACTCATT GGGTGTCTGA GTTCTGCGAT ATTCATCCCT                  100
CAGCCAATGA GCTTACTGTT CTCGTGGGGG GTTTGTGAGC CTTGGGTAGG                  150
AAGTTTTGCA AGTTCCGCCT ACAGCTCTAG CTTGTGAATT TGTACCCTTT                  200
CACGTAAAAA AGTAGTCCAG AGTTTACTAC ACCCTCCCTC CCCCCTCCCA                  250
CCTCGTGCTG TGCTGAGTTT AGAAGTCTTC CTTATAGAAG TCTTCCGTAT                  300
AGAACTCTTC CGGAGGAAGG AGGGAGGACC CCCCCCCTTT GCTCTCCCAG                  350
CATGCATTGT GTCAACGCCA TTGCACTGAG CTGGTCGAAG AAGTAAGCCG                  400
CTAGCTTGCG ACTCTACTCT TATCTTAACT TAGCTCGGCT TCCTGCTGGT                  450
ACCCTTTGTG CC                                                          462
ATG TCT GAT AAC AAG AAA CCA GAC AAA GCC CAC AGT GGC TCA                 504
GGT GGT GAC GGT GAT GGG AAT AGG TGC AAT TTA TTG CAC CGG                 546
TAC TCC CTG GAA GAA ATT CTG CCT TAT CTA GGG TGG CTG GTC                 588
TTC GCT GTT GTC ACA ACA AGT TTT CTG GCG CTC CAG ATG TTC                 630
ATA GAC GCC CTT TAT GAG GAG CAG TAT GAA AGG GAT GTG GCC                 672
TGG ATA GCC AGG CAA AGC AAG CGC ATG TCC TCT GTC GAT GAG                 714
GAT GAA GAC GAT GAG GAT GAT GAG GAT GAC TAC TAC GAC GAC                 756
GAG GAC GAC GAC GAC GAT GCC TTC TAT GAT GAT GAG GAT GAT                 798
GAG GAA GAA GAA TTG GAG AAC CTG ATG GAT GAT GAA TCA GAA                 840
GAT GAG GCC GAA GAA GAG ATG AGC GTG GAA ATG GGT GCC GGA                 882
GCT GAG GAA ATG GGT GCT GGC GCT AAC TGT GCC TGT GTT CCT                 924
GGC CAT CAT TTA AGG AAG AAT GAA GTG AAG TGT AGG ATG ATT                 966
TAT TTC TTC CAC GAC CCT AAT TTC CTG GTG TCT ATA CCA GTG                1008
AAC CCT AAG GAA CAA ATG GAG TGT AGG TGT GAA AAT GCT GAT                1050
GAA GAG GTT GCA ATG GAA GAG GAA GAA GAA GAA GAG GAG GAG                1092
GAG GAG GAA GAG GAA ATG GGA AAC CCG GAT GGC TTC TCA CCT                1134
TAG                                                                   1137
GCATGCAGTT GCAAAGCCCA GAAGAAAGAA ATGGACAGCG GAAGAAGTGG                 1187
```

-continued

| | |
|---|---|
| TTGTTTTTTT TTCCCCTTCA TTAATTTTCT AGTTTTTAGT AATCCAGAAA | 1237 |
| ATTTGATTTT GTTCTAAAGT TCATTATGCA AAGATGTCAC CAACAGACTT | 1287 |
| CTGACTGCAT GGTGAACTTT CATATGATAC ATAGGATTAC ACTTGTACCT | 1337 |
| GTTAAAAATA AAAGTTTGAC TTGCATAC | 1365 |

(2) INFORMATION FOR SEQ ID NO: 5:

(i) SEQUENCE CHARACTERISTICS:
        (A) LENGTH: 4698 base pairs
        (B) TYPE: nucleic acid
        (C) STRANDEDNESS: single
        (D) TOPOLOGY: linear (ii) MOLECULE TYPE: genomic DNA (xi) SEQUENCE DESCRIPTION: SEQ ID NO: 5:

| | |
|---|---|
| ACCACAGGAG AATGAAAAGA ACCCGGGACT CCCAAAGACG CTAGATGTGT | 50 |
| GAAGATCCTG ATCACTCATT GGGTGTCTGA GTTCTGCGAT ATTCATCCCT | 100 |
| CAGCCAATGA GCTTACTGTT CTCGTGGGGG GTTTGTGAGC CTTGGGTAGG | 150 |
| AAGTTTTGCA AGTTCCGCCT ACAGCTCTAG CTTGTGAATT TGTACCCTTT | 200 |
| CACGTAAAAA AGTAGTCCAG AGTTTACTAC ACCCTCCCTC CCCCCTCCCA | 250 |
| CCTCGTGCTG TGCTGAGTTT AGAAGTCTTC CTTATAGAAG TCTTCCGTAT | 300 |
| AGAACTCTTC CGGAGGAAGG AGGGAGGACC CCCCCCCTTT GCTCTCCCAG | 350 |
| CATGCATTGT GTCAACGCCA TTGCACTGAG CTGGTCGAAG AAGTAAGCCG | 400 |
| CTAGCTTGCG ACTCTACTCT TATCTTAACT TAGCTCGGCT TCCTGCTGGT | 450 |
| ACCCTTTGTG CC | 462 |
| ATG TCT GAT AAC AAG AAA CCA GAC AAA GCC CAC AGT GGC TCA | 504 |
| GGT GGT GAC GGT GAT GGG AAT AGG TGC AAT TTA TTG CAC CGG | 546 |
| TAC TCC CTG GAA GAA ATT CTG CCT TAT CTA GGG TGG CTG GTC | 588 |
| TTC GCT GTT GTC ACA ACA AGT TTT CTG GCG CTC CAG ATG TTC | 630 |
| ATA GAC GCC CTT TAT GAG GAG CAG TAT GAA AGG GAT GTG GCC | 672 |
| TGG ATA GCC AGG CAA AGC AAG CGC ATG TCC TCT GTC GAT GAG | 714 |
| GAT GAA GAC GAT GAG GAT GAT GAG GAT GAC TAC TAC GAC GAC | 756 |
| GAG GAC GAC GAC GAC GAT GCC TTC TAT GAT GAT GAG GAT GAT | 798 |
| GAG GAA GAA GAA TTG GAG AAC CTG ATG GAT GAT GAA TCA GAA | 840 |
| GAT GAG GCC GAA GAA GAG ATG AGC GTG GAA ATG GGT GCC GGA | 882 |
| GCT GAG GAA ATG GGT GCT GGC GCT AAC TGT GCC T | 916 |
| GTGAGTAACC CGTGGTCTTT ACTCTAGATT CAGGTGGGGT GCATTCTTTA | 966 |
| CTCTTGCCCA CATCTGTAGT AAAGACCACA TTTTGGTTGG GGGTCATTGC | 1016 |
| TGGAGCCATT CCTGGCTCTC CTGTCCACGC CTATCCCCGC TCCTCCCATC | 1066 |
| CCCCACTCCT TGCTCCGCTC TCTTTCCTTT TCCCACCTTG CCTCTGGAGC | 1116 |
| TTCAGTCCAT CCTGCTCTGC TCCCTTTCCC CTTTGCTCTC CTTGCTCCCC | 1166 |
| TCCCCCTCGG CTCAACTTTT CGTGCCTTCT GCTCTCTGAT CCCCACCCTC | 1216 |
| TTCAGGCTTC CCCATTTGCT CCTCTCCCGA AACCCTCCCC TTCCTGTTCC | 1266 |
| CCTTTTCGCG CCTTTTCTTT CCTGCTCCCC TCCCCCTCCC TATTTACCTT | 1316 |
| TCACCAGCTT TGCTCTCCCT GCTCCCCTCC CCCTTTTGCA CCTTTTCTTT | 1366 |

```
TCCTGCTCCC CTCCCCCTCC CCTCCCTGTT TACCCTTCAC CGCTTTTCCT      1416

CTACCTGCTT CCCTCCCCCT TGCTGCTCCC TCCCTATTTG CATTTTCGGG      1466

TGCTCCTCCC TCCCCCTCCC CCTCCCTCCC TATTTGCATT TTCGGGTGCT      1516

CCTCCCTCCC CCTCCCCAGG CCTTTTTTTT TTTTTTTTTT TTTTTTTTTT      1566

TTGGTTTTTC GAGACAGGGT TTCTCTTTGT ATCCCTGGCT GTCCTGGCAC      1616

TCACTCTGTA GACCAGGCTG GCCTCAAACT CAGAAATCTG CCTGCCTCTG      1666

CCTCCCAAAT GCTGGGATTA AAGGCTTGCA CCAGGACTGC CCCAGTGCAG      1716

GCCTTTCTTT TTTCTCCTCT CTGGTCTCCC TAATCCCTTT TCTGCATGTT      1766

AACTCCCCTT TTGGCACCTT TCCTTTACAG GACCCCCTCC CCCTCCCTGT      1816

TTCCCTTCCG GCACCCTTCC TAGCCCTGCT CTGTTCCCTC TCCCTGCTCC      1866

CCTCCCCCTC TTTGCTCGAC TTTTAGCAGC CTTACCTCTC CCTGCTTTCT      1916

GCCCCGTTCC CCTTTTTTGT GCCTTTCCTC CTGGCTCCCC TCCACCTTCC      1966

AGCTCACCTT TTTGTTTGTT TGGTTGTTTG GTTGTTTGGT TTGCTTTTTT      2016

TTTTTTTTTT GCACCTTGTT TTCCAAGATC CCCCTCCCCC TCCGGCTTCC      2066

CCTCTGTGTG CCTTTCCTGT TCCCTCCCCC TCGCTGGCTC CCCCTCCCTT      2116

TCTGCCTTTC CTGTCCCTGC TCCCTTCTCT GCTAACCTTT TAATGCCTTT      2166

CTTTTCTAGA CTCCCCCCTC CAGGCTTGCT GTTTGCTTCT GTGCACTTTT      2216

CCTGACCCTG CTCCCCTTCC CCTCCCAGCT CCCCCCTCTT TTCCCACCTC      2266

CCTTTCTCCA GCCTGTCACC CCTCCTTCTC TCCTCTCTGT TTCTCCCACT      2316

TCCTGCTTCC TTTACCCCTT CCCTCTCCCT ACTCTCCTCC CTGCCTGCTG      2366

GACTTCCTCT CCAGCCGCCC AGTTCCCTGC AGTCCTGGAG TCTTTCCTGC      2416

CTCTCTGTCC ATCACTTCCC CCTAGTTTCA CTTCCCTTTC ACTCTCCCCT      2466

ATGTGTCTCT CTTCCTATCT ATCCCTTCCT TTCTGTCCCC TCTCCTCTGT      2516

CCATCACCTC TCTCCTCCCT TCCCTTTCCT CTCTCTTCCA TTTTCTTCCA      2566

CCTGCTTCTT TACCCTGCCT CTCCCATTGC CCTCTTACCT TTATGCCCAT      2616

TCCATGTCCC CTCTCAATTC CCTGTCCCAT TGTGCTCCCT CACATCTTCC      2666

ATTTCCCTCT TTCTCCCTTA GCCTCTTCTT CCTCTTCTCT TGTATCTCCC      2716

TTCCCTTTGC TTCTCCCTCC TCCTTTCCCC TTCCCCTATG CCCTCTACTC      2766

TACTTGATCT TCTCTCCTCT CCACATACCC TTTTTCCTTT CCACCCTGCC      2816

CTTTGTCCCC AGACCCTACA GTATCCTGTG CACAGGAAGT GGGAGGTGCC      2866

ATCAACAACA AGGAGGCAAG AAACAGAGCA AAATCCCAAA ATCAGCAGGA      2916

AAGGCTGGAT GAAAATAAGG CCAGGTTCTG AGGACAGCTG GAATCTAGCC      2966

AAGTGGCTCC TATAACCCTA AGTACCAAGG GAGAAAGTGA TGGTGAAGTT      3016

CTTGATCCTT GCTGCTTCTT TTACATATGT TGGCACATCT TTCTCAAATG      3066

CAGGCCATGC TCCATGCTTG GCGCTTGCTC AGCGTGGTTA AGTAATGGGA      3116

GAATCTGAAA ACTAGGGGCC AGTGGTTTGT TTTGGGGACA AATTAGCACG      3166

TAGTGATATT TCCCCCTAAA AATTATAACA AACAGATTCA TGATTTGAGA      3216

TCCTTCTACA GGTGAGAAGT GGAAAAATTG TCACTATGAA GTTCTTTTTA      3266

GGCTAAAGAT ACTTGGAACC ATAGAAGCGT TGTTAAAATA CTGCTTTCTT      3316

TTGCTAAAAT ATTCTTTCTC ACATATTCAT ATTCTCCAG                 3355
```

| | |
|---|---|
| GT GTT CCT GGC CAT CAT TTA AGG AAG AAT GAA GTG AAG TGT | 3396 |
| AGG ATG ATT TAT TTC TTC CAC GAC CCT AAT TTC CTG GTG TCT | 3438 |
| ATA CCA GTG AAC CCT AAG GAA CAA ATG GAG TGT AGG TGT GAA | 3480 |
| AAT GCT GAT GAA GAG GTT GCA ATG GAA GAG GAA GAA GAA GAA | 3522 |
| GAG GAG GAG GAG GAG GAA GAG GAA ATG GGA AAC CCG GAT GGC | 3564 |
| TTC TCA CCT TAG | 3576 |
| GCATGCAGGT ACTGGCTTCA CTAACCAACC ATTCCTAACA TATGCCTGTA | 3626 |
| GCTAAGAGCA TCTTTTTAAA AAATATTATT GGTAAACTAA ACAATTGTTA | 3676 |
| TCTTTTTACA TTAATAAGTA TTAAATTAAT CCAGTATACA GTTTTAAGAA | 3726 |
| CCCTAAGTTA AACAGAAGTC AATGATGTCT AGATGCCTGT TCTTTAGATT | 3776 |
| GTAGTGAGAC TACTTACTAC AGATGAGAAG TTGTTAGACT CGGGAGTAGA | 3826 |
| GACCAGTAAA AGATCATGCA GTGAAATGTG GCCATGGAAA TCGCATATTG | 3876 |
| TTCTTATAGT ACCTTTGAGA CAGCTGATAA CAGCTGACAA AAATAAGTGT | 3926 |
| TTCAAGAAAG ATCACACGCC ATGGTTCACA TGCAAATTAT TATTTTGTCG | 3976 |
| TTCTGATTTT TTTCATTTCT AGACCTGTGG TTTTAAAGAG ATGAAAATCT | 4026 |
| CTTAAAATTT CCTTCATCTT TAATTTTCCT TAACTTTAGT TTTTTTCACT | 4076 |
| TAGAATTCAA TTCAAATTCT TAATTCAATC TTAATTTTTA GATTTCTTAA | 4126 |
| AATGTTTTTT AAAAAAAATG CAAATCTCAT TTTTAAGAGA TGAAAGCAGA | 4176 |
| GTAACTGGGG GGCTTAGGGA ATCTGTAGGG TTGCGGTATA GCAATAGGGA | 4226 |
| GTTCTGGTCT CTGAGAAGCA GTCAGAGAGA ATGGAAAACC AGGCCCTTGC | 4276 |
| CAGTAGGTTA GTGAGGTTGA TATGATCAGA TTATGGACAC TCTCCAAATC | 4326 |
| ATAAATACTC TAACAGCTAA GGATCTCTGA GGGAAACACA ACAGGGAAAT | 4376 |
| ATTTTAGTTT CTCCTTGAGA AACAATGACA AGACATAAAA TTGGCAAGAA | 4426 |
| AGTCAGGAGT GTATTCTAAT AAGTGTTGCT TATCTCTTAT TTTCTTCTAC | 4476 |
| AGTTGCAAAG CCCAGAAGAA AGAAATGGAC AGCGGAAGAA GTGGTTGTTT | 4526 |
| TTTTTTCCCC TTCATTAATT TTCTAGTTTT TAGTAATCCA GAAAATTTGA | 4576 |
| TTTTGTTCTA AAGTTCATTA TGCAAAGATG TCACCAACAG ACTTCTGACT | 4626 |
| GCATGGTGAA CTTTCATATG ATACATAGGA TTACACTTGT ACCTGTTAAA | 4676 |
| AATAAAAGTT TGACTTGCAT AC | 4698 |

(2) INFORMATION FOR SEQ ID NO: 6:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 6:

Leu Pro Tyr Leu Gly Trp Leu Val Phe
             5

(2) INFORMATION FOR SEQ ID NO: 7:

(i) SEQUENCE CHARACTERISTICS:
        (A) LENGTH: 2419 base pairs (B) TYPE:  nucleic acid
       (C) STRANDEDNESS:  single
       (D) TOPOLOGY:  linear (ii) MOLECULE TYPE:  genomic DNA (xi) SEQUENCE DESCRIPTION:  SEQ ID NO: 7:

| | | |
|---|---|---|
| GGATCCAGGC CCTGCCAGGA AAAATATAAG GGCCCTGCGT GAGAACAGAG | 50 |
| GGGGTCATCC ACTGCATGAG AGTGGGGATG TCACAGAGTC CAGCCCACCC | 100 |
| TCCTGGTAGC ACTGAGAAGC CAGGGCTGTG CTTGCGGTCT GCACCCTGAG | 150 |
| GGCCCGTGGA TTCCTCTTCC TGGAGCTCCA GGAACCAGGC AGTGAGGCCT | 200 |
| TGGTCTGAGA CAGTATCCTC AGGTCACAGA GCAGAGGATG CACAGGGTGT | 250 |
| GCCAGCAGTG AATGTTTGCC CTGAATGCAC ACCAAGGGCC CCACCTGCCA | 300 |
| CAGGACACAT AGGACTCCAC AGAGTCTGGC CTCACCTCCC TACTGTCAGT | 350 |
| CCTGTAGAAT CGACCTCTGC TGGCCGGCTG TACCCTGAGT ACCCTCTCAC | 400 |
| TTCCTCCTTC AGGTTTTCAG GGACAGGCC AACCCAGAGG ACAGGATTCC | 450 |
| CTGGAGGCCA CAGAGGAGCA CCAAGGAGAA GATCTGTAAG TAGGCCTTTG | 500 |
| TTAGAGTCTC CAAGGTTCAG TTCTCAGCTG AGGCCTCTCA CACACTCCCT | 550 |
| CTCTCCCCAG GCCTGTGGGT CTTCATTGCC CAGCTCCTGC CCACACTCCT | 600 |
| GCCTGCTGCC CTGACGAGAG TCATCATGTC TCTTGAGCAG AGGAGTCTGC | 650 |
| ACTGCAAGCC TGAGGAAGCC CTTGAGGCCC AACAAGAGGC CCTGGGCCTG | 700 |
| GTGTGTGTGC AGGCTGCCAC CTCCTCCTCC TCTCCTCTGG TCCTGGGCAC | 750 |
| CCTGGAGGAG GTGCCCACTG CTGGGTCAAC AGATCCTCCC CAGAGTCCTC | 800 |
| AGGGAGCCTC CGCCTTTCCC ACTACCATCA ACTTCACTCG ACAGAGGCAA | 850 |
| CCCAGTGAGG GTTCCAGCAG CCGTGAAGAG GAGGGGCCAA GCACCTCTTG | 900 |
| TATCCTGGAG TCCTTGTTCC GAGCAGTAAT CACTAAGAAG GTGGCTGATT | 950 |
| TGGTTGGTTT TCTGCTCCTC AAATATCGAG CCAGGGAGCC AGTCACAAAG | 1000 |
| GCAGAAATGC TGGAGAGTGT CATCAAAAAT TACAAGCACT GTTTTCCTGA | 1050 |
| GATCTTCGGC AAAGCCTCTG AGTCCTTGCA GCTGGTCTTT GGCATTGACG | 1100 |
| TGAAGGAAGC AGACCCCACC GGCCACTCCT ATGTCCTTGT CACCTGCCTA | 1150 |
| GGTCTCTCCT ATGATGGCCT GCTGGGTGAT AATCAGATCA TGCCCAAGAC | 1200 |
| AGGCTTCCTG ATAATTGTCC TGGTCATGAT TGCAATGGAG GGCGGCCATG | 1250 |
| CTCCTGAGGA GGAAATCTGG GAGGAGCTGA GTGTGATGGA GGTGTATGAT | 1300 |
| GGGAGGGAGC ACAGTGCCTA TGGGGAGCCC AGGAAGCTGC TCACCCAAGA | 1350 |
| TTTGGTGCAG GAAAAGTACC TGGAGTACGG CAGGTGCCGG ACAGTGATCC | 1400 |
| CGCACGCTAT GAGTTCCTGT GGGGTCCAAG GGCCCTCGCT GAAACCAGCT | 1450 |
| ATGTGAAAGT CCTTGAGTAT GTGATCAAGG TCAGTGCAAG AGTTCGCTTT | 1500 |
| TTCTTCCCAT CCCTGCGTGA AGCAGCTTTG AGAGAGGAGG AAGAGGGAGT | 1550 |
| CTGAGCATGA GTTGCAGCCA AGGCCAGTGG GAGGGGACT GGGCCAGTGC | 1600 |
| ACCTTCCAGG GCCGCGTCCA GCAGCTTCCC CTGCCTCGTG TGACATGAGG | 1650 |
| CCCATTCTTC ACTCTGAAGA GAGCGGTCAG TGTTCTCAGT AGTAGGTTTC | 1700 |
| TGTTCTATTG GGTGACTTGG AGATTTATCT TTGTTCTCTT TTGGAATTGT | 1750 |
| TCAAATGTTT TTTTTTAAGG GATGGTTGAA TGAACTTCAG CATCCAAGTT | 1800 |

-continued

```
TATGAATGAC AGCAGTCACA CAGTTCTGTG TATATAGTTT AAGGGTAAGA           1850

GTCTTGTGTT TTATTCAGAT TGGGAAATCC ATTCTATTTT GTGAATTGGG           1900

ATAATAACAG CAGTGGAATA AGTACTTAGA AATGTGAAAA ATGAGCAGTA           1950

AAATAGATGA GATAAAGAAC TAAAGAAATT AAGAGATAGT CAATTCTTGC           1000

CTTATACCTC AGTCTATTCT GTAAAATTTT TAAAGATATA TGCATACCTG           1050

GATTTCCTTG GCTTCTTTGA GAATGTAAGA GAAATTAAAT CTGAATAAAG           1100

AATTCTTCCT GTTCACTGGC TCTTTTCTTC TCCATGCACT GAGCATCTGC           1150

TTTTTGGAAG GCCCTGGGTT AGTAGTGGAG ATGCTAAGGT AAGCCAGACT           1200

CATACCCACC CATAGGGTCG TAGAGTCTAG GAGCTGCAGT CACGTAATCG           1250

AGGTGGCAAG ATGTCCTCTA AGATGTAGG GAAAAGTGAG AGAGGGGTGA            1300

GGGTGTGGGG CTCCGGGTGA GAGTGGTGGA GTGTCAATGC CCTGAGCTGG           1350

GGCATTTTGG GCTTTGGGAA ACTGCAGTTC CTTCTGGGGG AGCTGATTGT           1400

AATGATCTTG GGTGGATCC                                             1419
```

(2) INFORMATION FOR SEQ ID NO: 8:

(i) SEQUENCE CHARACTERISTICS:
        (A) LENGTH: 5674 base pairs
        (B) TYPE: nucleic acid
        (C) STRANDEDNESS: single
        (D) TOPOLOGY: linear (ii) MOLECULE TYPE: genomic DNA (ix) FEATURE:
        (A) NAME/KEY: MAGE-1 gene (xi) SEQUENCE DESCRIPTION: SEQ ID NO: 8:

```
CCCGGGGCAC CACTGGCATC CCTCCCCCTA CCACCCCCAA TCCCTCCCTT            50

TACGCCACCC ATCCAAACAT CTTCACGCTC ACCCCCAGCC CAAGCCAGGC           100

AGAATCCGGT TCCACCCCTG CTCTCAACCC AGGGAAGCCC AGGTGCCCAG           150

ATGTGACGCC ACTGACTTGA GCATTAGTGG TTAGAGAGAA GCGAGGTTTT           200

CGGTCTGAGG GGCGGCTTGA GATCGGTGGA GGGAAGCGGG CCCAGCTCTG           250

TAAGGAGGCA AGGTGACATG CTGAGGGAGG ACTGAGGACC CACTTACCCC           300

AGATAGAGGA CCCCAAATAA TCCCTTCATG CCAGTCCTGG ACCATCTGGT           350

GGTGGACTTC TCAGGCTGGG CCACCCCCAG CCCCCTTGCT GCTTAAACCA           400

CTGGGGACTC GAAGTCAGAG CTCCGTGTGA TCAGGGAAGG GCTGCTTAGG           450

AGAGGGCAGC GTCCAGGCTC TGCCAGACAT CATGCTCAGG ATTCTCAAGG           500

AGGGCTGAGG GTCCCTAAGA CCCCACTCCC GTGACCCAAC CCCCACTCCA           550

ATGCTCACTC CCGTGACCCA ACCCCCTCTT CATTGTCATT CCAACCCCCA           600

CCCCACATCC CCCACCCCAT CCCTCAACCC TGATGCCCAT CCGCCCAGCC           650

ATTCCACCCT CACCCCCACC CCCACCCCCA CGCCCACTCC CACCCCCACC           700

CAGGCAGGAT CCGGTTCCCG CCAGGAAACA TCCGGGTGCC CGGATGTGAC           750

GCCACTGACT TGCGCATTGT GGGGCAGAGA GAAGCGAGGT TTCCATTCTG           800

AGGGACGGCG TAGAGTTCGG CCGAAGGAAC CTGACCCAGG CTCTGTGAGG           850

AGGCAAGGTG AGAGGCTGAG GGAGGACTGA GGACCCCGCC ACTCCAAATA           900

GAGAGCCCCA AATATTCCAG CCCCGCCCTT GCTGCCAGCC CTGGCCCACC           950
```

```
CGCGGGAAGA CGTCTCAGCC TGGGCTGCCC CCAGACCCCT GCTCCAAAAG      1000

CCTTGAGAGA CACCAGGTTC TTCTCCCCAA GCTCTGGAAT CAGAGGTTGC      1050

TGTGACCAGG GCAGGACTGG TTAGGAGAGG GCAGGGCACA GGCTCTGCCA      1100

GGCATCAAGA TCAGCACCCA AGAGGGAGGG CTGTGGGCCC CCAAGACTGC      1150

ACTCCAATCC CCACTCCCAC CCCATTCGCA TTCCCATTCC CCACCCAACC      1200

CCCATCTCCT CAGCTACACC TCCACCCCCA TCCCTACTCC TACTCCGTCA      1250

CCTGACCACC ACCCTCCAGC CCCAGCACCA GCCCCAACCC TTCTGCCACC      1300

TCACCCTCAC TGCCCCCAAC CCCACCCTCA TCTCTCTCAT GTGCCCCACT      1350

CCCATCGCCT CCCCCATTCT GGCAGAATCC GGTTTGCCCC TGCTCTCAAC      1400

CCAGGGAAGC CCTGGTAGGC CCGATGTGAA ACCACTGACT TGAACCTCAC      1450

AGATCTGAGA GAAGCCAGGT TCATTTAATG GTTCTGAGGG GCGGCTTGAG      1500

ATCCACTGAG GGGAGTGGTT TTAGGCTCTG TGAGGAGGCA AGGTGAGATG      1550

CTGAGGGAGG ACTGAGGAGG CACACACCCC AGGTAGATGG CCCCAAAATG      1600

ATCCAGTACC ACCCCTGCTG CCAGCCCTGG ACCACCCGGC CAGGACAGAT      1650

GTCTCAGCTG GACCACCCCC CGTCCCGTCC CACTGCCACT TAACCCACAG      1700

GGCAATCTGT AGTCATAGCT TATGTGACCG GGGCAGGGTT GGTCAGGAGA      1750

GGCAGGGCCC AGGCATCAAG GTCCAGCATC CGCCCGGCAT TAGGGTCAGG      1800

ACCCTGGGAG GGAACTGAGG GTTCCCCACC CACACCTGTC TCCTCATCTC      1850

CACCGCCACC CCACTCACAT TCCCATACCT ACCCCCTACC CCCAACCTCA      1900

TCTTGTCAGA ATCCCTGCTG TCAACCCACG GAAGCCACGG GAATGGCGGC      1950

CAGGCACTCG GATCTTGACG TCCCCATCCA GGGTCTGATG GAGGGAAGGG      2000

GCTTGAACAG GGCCTCAGGG GAGCAGAGGG AGGGCCCTAC TGCGAGATGA      2050

GGGAGGCCTC AGAGGACCCA GCACCCTAGG ACACCGCACC CCTGTCTGAG      2100

ACTGAGGCTG CCACTTCTGG CCTCAAGAAT CAGAACGATG GGGACTCAGA      2150

TTGCATGGGG GTGGGACCCA GGCCTGCAAG GCTTACGCGG AGGAAGAGGA      2200

GGGAGGACTC AGGGGACCTT GGAATCCAGA TCAGTGTGGA CCTCGGCCCT      2250

GAGAGGTCCA GGGCACGGTG GCCACATATG GCCCATATTT CCTGCATCTT      2300

TGAGGTGACA GGACAGAGCT GTGGTCTGAG AAGTGGGGCC TCAGGTCAAC      2350

AGAGGGAGGA GTTCCAGGAT CCATATGGCC CAAGATGTGC CCCCTTCATG      2400

AGGACTGGGG ATATCCCCGG CTCAGAAAGA AGGGACTCCA CACAGTCTGG      2450

CTGTCCCCTT TTAGTAGCTC TAGGGGGACC AGATCAGGGA TGGCGGTATG      2500

TTCCATTCTC ACTTGTACCA CAGGCAGGAA GTTGGGGGGC CCTCAGGGAG      2550

ATGGGTCTT GGGGTAAAGG GGGGATGTCT ACTCATGTCA GGGAATTGGG       2600

GGTTGAGGAA GCACAGGCGC TGGCAGGAAT AAAGATGAGT GAGACAGACA      2650

AGGCTATTGG AATCCACACC CCAGAACCAA AGGGGTCAGC CCTGGACACC      2700

TCACCCAGGA TGTGGCTTCT TTTTCACTCC TGTTTCCAGA TCTGGGGCAG      2750

GTGAGGACCT CATTCTCAGA GGGTGACTCA GGTCAACGTA GGGACCCCCA      2800

TCTGGTCTAA AGACAGAGCG GTCCCAGGAT CTGCCATGCG TTCGGGTGAG      2850

GAACATGAGG GAGGACTGAG GGTACCCCAG GACCAGAACA CTGAGGGAGA      2900

CTGCACAGAA ATCAGCCCTG CCCCTGCTGT CACCCCAGAG AGCATGGGCT      2950
```

```
GGGCCGTCTG CCGAGGTCCT TCCGTTATCC TGGGATCATT GATGTCAGGG       3000

ACGGGGAGGC CTTGGTCTGA GAAGGCTGCG CTCAGGTCAG TAGAGGGAGC       3050

GTCCCAGGCC CTGCCAGGAG TCAAGGTGAG GACCAAGCGG GCACCTCACC       3100

CAGGACACAT TAATTCCAAT GAATTTTGAT ATCTCTTGCT GCCCTTCCCC       3150

AAGGACCTAG GCACGTGTGG CCAGATGTTT GTCCCCTCCT GTCCTTCCAT       3200

TCCTTATCAT GGATGTGAAC TCTTGATTTG GATTTCTCAG ACCAGCAAAA       3250

GGGCAGGATC CAGGCCCTGC CAGGAAAAAT ATAAGGGCCC TGCGTGAGAA       3300

CAGAGGGGGT CATCCACTGC ATGAGAGTGG GGATGTCACA GAGTCCAGCC       3350

CACCCTCCTG GTAGCACTGA GAAGCCAGGG CTGTGCTTGC GGTCTGCACC       3400

CTGAGGGCCC GTGGATTCCT CTTCCTGGAG CTCCAGGAAC CAGGCAGTGA       3450

GGCCTTGGTC TGAGACAGTA TCCTCAGGTC ACAGAGCAGA GGATGCACAG       3500

GGTGTGCCAG CAGTGAATGT TTGCCCTGAA TGCACACCAA GGGCCCCACC       3550

TGCCACAGGA CACATAGGAC TCCACAGAGT CTGGCCTCAC CTCCCTACTG       3600

TCAGTCCTGT AGAATCGACC TCTGCTGGCC GGCTGTACCC TGAGTACCCT       3650

CTCACTTCCT CCTTCAGGTT TTCAGGGGAC AGGCCAACCC AGAGGACAGG       3700

ATTCCCTGGA GGCCACAGAG GAGCACCAAG GAGAAGATCT GTAAGTAGGC       3750

CTTTGTTAGA GTCTCCAAGG TTCAGTTCTC AGCTGAGGCC TCTCACACAC       3800

TCCCTCTCTC CCCAGGCCTG TGGGTCTTCA TTGCCCAGCT CCTGCCCACA       3850

CTCCTGCCTG CTGCCCTGAC GAGAGTCATC                             3880

ATG TCT CTT GAG CAG AGG AGT CTG CAC TGC AAG CCT GAG GAA     3922

GCC CTT GAG GCC CAA CAA GAG GCC CTG GGC CTG GTG TGT GTG     3964

CAG GCT GCC ACC TCC TCC TCC TCT CCT CTG GTC CTG GGC ACC     4006

CTG GAG GAG GTG CCC ACT GCT GGG TCA ACA GAT CCT CCC CAG     4048

AGT CCT CAG GGA GCC TCC GCC TTT CCC ACT ACC ATC AAC TTC     4090

ACT CGA CAG AGG CAA CCC AGT GAG GGT TCC AGC AGC CGT GAA     4132

GAG GAG GGG CCA AGC ACC TCT TGT ATC CTG GAG TCC TTG TTC     4174

CGA GCA GTA ATC ACT AAG AAG GTG GCT GAT TTG GTT GGT TTT     4216

CTG CTC CTC AAA TAT CGA GCC AGG GAG CCA GTC ACA AAG GCA     4258

GAA ATG CTG GAG AGT GTC ATC AAA AAT TAC AAG CAC TGT TTT     4300

CCT GAG ATC TTC GGC AAA GCC TCT GAG TCC TTG CAG CTG GTC     4342

TTT GGC ATT GAC GTG AAG GAA GCA GAC CCC ACC GGC CAC TCC     4384

TAT GTC CTT GTC ACC TGC CTA GGT CTC TCC TAT GAT GGC CTG     4426

CTG GGT GAT AAT CAG ATC ATG CCC AAG ACA GGC TTC CTG ATA     4468

ATT GTC CTG GTC ATG ATT GCA ATG GAG GGC GGC CAT GCT CCT     4510

GAG GAG GAA ATC TGG GAG GAG CTG AGT GTG ATG GAG GTG TAT     4552

GAT GGG AGG GAG CAC AGT GCC TAT GGG GAG CCC AGG AAG CTG     4594

CTC ACC CAA GAT TTG GTG CAG GAA AAG TAC CTG GAG TAC GGC     4636

AGG TGC CGG ACA GTG ATC CCG CAC GCT ATG AGT CCT GTG GGG     4678

GTC CAA GGG CCC TCG CTG AAA CCA GCT ATG TGA                 4711

AAGTCCTTGA GTATGTGATC AAGGTCAGTG CAAGAGTTC                   4750
```

-continued

| | |
|---|---|
| GCTTTTTCTT CCCATCCCTG CGTGAAGCAG CTTTGAGAGA GGAGGAAGAG | 4800 |
| GGAGTCTGAG CATGAGTTGC AGCCAAGGCC AGTGGGAGGG GGACTGGGCC | 4850 |
| AGTGCACCTT CCAGGGCCGC GTCCAGCAGC TTCCCCTGCC TCGTGTGACA | 4900 |
| TGAGGCCCAT TCTTCACTCT GAAGAGAGCG GTCAGTGTTC TCAGTAGTAG | 4950 |
| GTTTCTGTTC TATTGGGTGA CTTGGAGATT TATCTTTGTT CTCTTTTGGA | 5000 |
| ATTGTTCAAA TGTTTTTTTT TAAGGGATGG TTGAATGAAC TTCAGCATCC | 5050 |
| AAGTTTATGA ATGACAGCAG TCACACAGTT CTGTGTATAT AGTTTAAGGG | 5100 |
| TAAGAGTCTT GTGTTTTATT CAGATTGGGA AATCCATTCT ATTTTGTGAA | 5150 |
| TTGGGATAAT AACAGCAGTG GAATAAGTAC TTAGAAATGT GAAAAATGAG | 5200 |
| CAGTAAAATA GATGAGATAA AGAACTAAAG AAATTAAGAG ATAGTCAATT | 5250 |
| CTTGCCTTAT ACCTCAGTCT ATTCTGTAAA ATTTTTAAAG ATATATGCAT | 5300 |
| ACCTGGATTT CCTTGGCTTC TTTGAGAATG TAAGAGAAAT TAAATCTGAA | 5350 |
| TAAAGAATTC TTCCTGTTCA CTGGCTCTTT TCTTCTCCAT GCACTGAGCA | 5400 |
| TCTGCTTTTT GGAAGGCCCT GGGTTAGTAG TGGAGATGCT AAGGTAAGCC | 5450 |
| AGACTCATAC CCACCCATAG GGTCGTAGAG TCTAGGAGCT GCAGTCACGT | 5500 |
| AATCGAGGTG GCAAGATGTC CTCTAAAGAT GTAGGGAAAA GTGAGAGAGG | 5550 |
| GGTGAGGGTG TGGGGCTCCG GGTGAGAGTG GTGGAGTGTC AATGCCCTGA | 5600 |
| GCTGGGGCAT TTTGGGCTTT GGGAAACTGC AGTTCCTTCT GGGGGAGCTG | 5650 |
| ATTGTAATGA TCTTGGGTGG ATCC | 5674 |

(2) INFORMATION FOR SEQ ID NO: 9:

(i) SEQUENCE CHARACTERISTICS:
        (A) LENGTH: 4157 base pairs
        (B) TYPE: nucleic acid
        (C) STRANDEDNESS: single
        (D) TOPOLOGY: linear (ii) MOLECULE TYPE: genomic DNA (ix) FEATURE:
        (A) NAME/KEY: MAGE-2 gene (xi) SEQUENCE DESCRIPTION: SEQ ID NO: 9:

| | |
|---|---|
| CCCATCCAGA TCCCCATCCG GGCAGAATCC GGTTCCACCC TTGCCGTGAA | 50 |
| CCCAGGGAAG TCACGGGCCC GGATGTGACG CCACTGACTT GCACATTGGA | 100 |
| GGTCAGAGGA CAGCGAGATT CTCGCCCTGA GCAACGGCCT GACGTCGGCG | 150 |
| GAGGGAAGCA GGCGCAGGCT CCGTGAGGAG GCAAGGTAAG ACGCCGAGGG | 200 |
| AGGACTGAGG CGGGCCTCAC CCCAGACAGA GGGCCCCCAA TTAATCCAGC | 250 |
| GCTGCCTCTG CTGCCGGGCC TGGACCACCC TGCAGGGGAA GACTTCTCAG | 300 |
| GCTCAGTCGC CACCACCTCA CCCCGCCACC CCCCGCCGCT TTAACCGCAG | 350 |
| GGAACTCTGG CGTAAGAGCT TTGTGTGACC AGGGCAGGGC TGGTTAGAAG | 400 |
| TGCTCAGGGC CCAGACTCAG CCAGGAATCA AGGTCAGGAC CCCAAGAGGG | 450 |
| GACTGAGGGC AACCCACCCC CTACCCTCAC TACCAATCCC ATCCCCCAAC | 500 |
| ACCAACCCCA CCCCCATCCC TCAAACACCA ACCCCACCCC CAAACCCCAT | 550 |
| TCCCATCTCC TCCCCCACCA CCATCCTGGC AGAATCCGGC TTTGCCCCTG | 600 |
| CAATCAACCC ACGGAAGCTC CGGGAATGGC GGCCAAGCAC GCGGATCCTG | 650 |

| | |
|---|---|
| ACGTTCACAT GTACGGCTAA GGGAGGGAAG GGGTTGGGTC TCGTGAGTAT | 700 |
| GGCCTTTGGG ATGCAGAGGA AGGGCCCAGG CCTCCTGGAA GACAGTGGAG | 750 |
| TCCTTAGGGG ACCCAGCATG CCAGGACAGG GGGCCCACTG TACCCCTGTC | 800 |
| TCAAACTGAG CCACCTTTTC ATTCAGCCGA GGGAATCCTA GGGATGCAGA | 850 |
| CCCACTTCAG GGGGTTGGGG CCCAGCCTGC GAGGAGTCAA GGGGAGGAAG | 900 |
| AAGAGGGAGG ACTGAGGGGA CCTTGGAGTC CAGATCAGTG GCAACCTTGG | 950 |
| GCTGGGGGAT CCTGGGCACA GTGGCCGAAT GTGCCCCGTG CTCATTGCAC | 1000 |
| CTTCAGGGTG ACAGAGAGTT GAGGGCTGTG GTCTGAGGGC TGGGACTTCA | 1050 |
| GGTCAGCAGA GGGAGGAATC CCAGGATCTG CCGGACCCAA GGTGTGCCCC | 1100 |
| CTTCATGAGG ACTCCCCATA CCCCCGGCCC AGAAAGAAGG GATGCCACAG | 1150 |
| AGTCTGGAAG TAAATTGTTC TTAGCTCTGG GGGAACCTGA TCAGGGATGG | 1200 |
| CCCTAAGTGA CAATCTCATT TGTACCACAG GCAGGAGGTT GGGGAACCCT | 1250 |
| CAGGGAGATA AGGTGTTGGT GTAAAGAGGA GCTGTCTGCT CATTTCAGGG | 1300 |
| GGTTCCCCCT TGAGAAAGGG CAGTCCCTGG CAGGAGTAAA GATGAGTAAC | 1350 |
| CCACAGGAGG CCATCATAAC GTTCACCCTA GAACCAAAGG GGTCAGCCCT | 1400 |
| GGACAACGCA CGTGGGTAA CAGGATGTGG CCCCTCCTCA CTTGTCTTTC | 1450 |
| CAGATCTCAG GGAGTTGATG ACCTTGTTTT CAGAAGGTGA CTCAGTCAAC | 1500 |
| ACAGGGGCCC CTCTGGTCGA CAGATGCAGT GGTTCTAGGA TCTGCCAAGC | 1550 |
| ATCCAGGTGG AGAGCCTGAG GTAGGATTGA GGGTACCCCT GGGCCAGAAT | 1600 |
| GCAGCAAGGG GGCCCCATAG AAATCTGCCC TGCCCCTGCG GTTACTTCAG | 1650 |
| AGACCCTGGG CAGGGCTGTC AGCTGAAGTC CCTCCATTAT CTGGGATCTT | 1700 |
| TGATGTCAGG GAAGGGGAGG CCTTGGTCTG AAGGGGCTGG AGTCAGGTCA | 1750 |
| GTAGAGGGAG GGTCTCAGGC CCTGCCAGGA GTGGACGTGA GGACCAAGCG | 1800 |
| GACTCGTCAC CCAGGACACC TGGACTCCAA TGAATTTGAC ATCTCTCGTT | 1850 |
| GTCCTTCGCG GAGGACCTGG TCACGTATGG CCAGATGTGG GTCCCCTCTA | 1900 |
| TCTCCTTCTG TACCATATCA GGGATGTGAG TTCTTGACAT GAGAGATTCT | 1950 |
| CAAGCCAGCA AAAGGGTGGG ATTAGGCCCT ACAAGGAGAA AGGTGAGGGC | 2000 |
| CCTGAGTGAG CACAGAGGGG ACCCTCCACC CAAGTAGAGT GGGGACCTCA | 2050 |
| CGGAGTCTGG CCAACCCTGC TGAGACTTCT GGGAATCCGT GGCTGTGCTT | 2100 |
| GCAGTCTGCA CACTGAAGGC CCGTGCATTC CTCTCCCAGG AATCAGGAGC | 2150 |
| TCCAGGAACC AGGCAGTGAG GCCTTGGTCT GAGTCAGTGC CTCAGGTCAC | 2200 |
| AGAGCAGAGG GGACGCAGAC AGTGCCAACA CTGAAGGTTT GCCTGGAATG | 2250 |
| CACACCAAGG GCCCCACCCG CCCAGAACAA ATGGGACTCC AGAGGGCCTG | 2300 |
| GCCTCACCCT CCCTATTCTC AGTCCTGCAG CCTGAGCATG TGCTGGCCGG | 2350 |
| CTGTACCCTG AGGTGCCCTC CCACTTCCTC CTTCAGGTTC TGAGGGGAC | 2400 |
| AGGCTGACAA GTAGGACCCG AGGCACTGGA GGAGCATTGA AGGAGAAGAT | 2450 |
| CTGTAAGTAA GCCTTTGTCA GAGCCTCCAA GGTTCAGTTC AGTTCTCACC | 2500 |
| TAAGGCCTCA CACACGCTCC TTCTCTCCCC AGGCCTGTGG GTCTTCATTG | 2550 |
| CCCAGCTCCT GCCCGCACTC CTGCCTGCTG CCCTGACCAG AGTCATC | 2597 |
| ATG CCT CTT GAG CAG AGG AGT CAG CAC TGC AAG CCT GAA GAA | 2639 |

```
GGC CTT GAG GCC CGA GGA GAG GCC CTG GGC CTG GTG GGT GCG        2681

CAG GCT CCT GCT ACT GAG GAG CAG CAG ACC GCT TCT TCC TCT        2723

TCT ACT CTA GTG GAA GTT ACC CTG GGG GAG GTG CCT GCT GCC        2765

GAC TCA CCG AGT CCT CCC CAC AGT CCT CAG GGA GCC TCC AGC        2807

TTC TCG ACT ACC ATC AAC TAC ACT CTT TGG AGA CAA TCC GAT        2849

GAG GGC TCC AGC AAC CAA GAA GAG GAG GGG CCA AGA ATG TTT        2891

CCC GAC CTG GAG TCC GAG TTC CAA GCA GCA ATC AGT AGG AAG        2933

ATG GTT GAG TTG GTT CAT TTT CTG CTC CTC AAG TAT CGA GCC        2975

AGG GAG CCG GTC ACA AAG GCA GAA ATG CTG GAG AGT GTC CTC        3017

AGA AAT TGC CAG GAC TTC TTT CCC GTG ATC TTC AGC AAA GCC        3059

TCC GAG TAC TTG CAG CTG GTC TTT GGC ATC GAG GTG GTG GAA        3101

GTG GTC CCC ATC AGC CAC TTG TAC ATC CTT GTC ACC TGC CTG        3143

GGC CTC TCC TAC GAT GGC CTG CTG GGC GAC AAT CAG GTC ATG        3185

CCC AAG ACA GGC CTC CTG ATA ATC GTC CTG GCC ATA ATC GCA        3227

ATA GAG GGC GAC TGT GCC CCT GAG GAG AAA ATC TGG GAG GAG        3269

CTG AGT ATG TTG GAG GTG TTT GAG GGG AGG GAG GAC AGT GTC        3311

TTC GCA CAT CCC AGG AAG CTG CTC ATG CAA GAT CTG GTG CAG        3353

GAA AAC TAC CTG GAG TAC CGG CAG GTG CCC GGC AGT GAT CCT        3395

GCA TGC TAC GAG TTC CTG TGG GGT CCA AGG GCC CTC ATT GAA        3437

ACC AGC TAT GTG AAA GTC CTG CAC CAT ACA CTA AAG ATC GGT        3479

GGA GAA CCT CAC ATT TCC TAC CCA CCC CTG CAT GAA CGG GCT        3521

TTG AGA GAG GGA GAA GAG TGA                                   3542

GTCTCAGCAC ATGTTGCAGC CAGGGCCAGT GGGAGGGGGT CTGGGCCAGT          3592

GCACCTTCCA GGGCCCCATC CATTAGCTTC CACTGCCTCG TGTGATATGA          3642

GGCCCATTCC TGCCTCTTTG AAGAGAGCAG TCAGCATTCT TAGCAGTGAG          3692

TTTCTGTTCT GTTGGATGAC TTTGAGATTT ATCTTTCTTT CCTGTTGGAA          3742

TTGTTCAAAT GTTCCTTTTA ACAAATGGTT GGATGAACTT CAGCATCCAA          3792

GTTTATGAAT GACAGTAGTC ACACATAGTG CTGTTTATAT AGTTTAGGGG          3842

TAAGAGTCCT GTTTTTTATT CAGATTGGGA AATCCATTCC ATTTTGTGAG          3892

TTGTCACATA ATAACAGCAG TGGAATATGT ATTTGCCTAT ATTGTGAACG          3942

AATTAGCAGT AAAATACATG ATACAAGGAA CTCAAAAGAT AGTTAATTCT          3992

TGCCTTATAC CTCAGTCTAT TATGTAAAAT TAAAAATATG TGTATGTTTT          4042

TGCTTCTTTG AGAATGCAAA AGAAATTAAA TCTGAATAAA TTCTTCCTGT          4092

TCACTGGCTC ATTTCTTTAC CATTCACTCA GCATCTGCTC TGTGGAAGGC          4142

CCTGGTAGTA GTGGG                                                4157

(2) INFORMATION FOR SEQ ID NO: 10:

(i) SEQUENCE CHARACTERISTICS:
        (A) LENGTH:  662 base pairs
        (B) TYPE:    nucleic acid
        (C) STRANDEDNESS: single
        (D) TOPOLOGY: linear (ii) MOLECULE TYPE: genomic DNA
```

(ix) FEATURE:
    (A) NAME/KEY: MAGE-21 gene (xi) SEQUENCE DESCRIPTION: SEQ ID NO: 10:

```
GGATCCCCAT GGATCCAGGA AGAATCCAGT TCCACCCCTG CTGTGAACCC          50
AGGGAAGTCA CGGGGCCGGA TGTGACGCCA CTGACTTGCG CGTTGGAGGT         100
CAGAGAACAG CGAGATTCTC GCCCTGAGCA ACGGCCTGAC GTCGGCGGAG         150
GGAAGCAGGC GCAGGCTCCG TGAGGAGGCA AGGTAAGATG CCGAGGGAGG         200
ACTGAGGCGG GCCTCACCCC AGACAGAGGG CCCCCAATAA TCCAGCGCTG         250
CCTCTGCTGC CAGGCCTGGA CCACCCTGCA GGGGAAGACT TCTCAGGCTC         300
AGTCGCCACC ACCTCACCCC GCCACCCCCC GCCGCTTTAA CCGCAGGGAA         350
CTCTGGTGTA AGAGCTTTGT GTGACCAGGG CAGGGCTGGT TAGAAGTGCT         400
CAGGGCCCAG ACTCAGCCAG GAATCAAGGT CAGGACCCCA AGAGGGGACT         450
GAGGGTAACC CCCCCGCACC CCCACCACCA TTCCCATCCC CCAACACCAA         500
CCCCACCCCC ATCCCCCAAC ACCAAACCCA CCACCATCGC TCAAACATCA         550
ACGGCACCCC CAAACCCCGA TTCCCATCCC CACCCATCCT GGCAGAATCG         600
GAGCTTTGCC CCTGCAATCA ACCCACGGAA GCTCCGGGAA TGGCGGCCAA         650
GCACGCGGAT CC                                                 662
```

(2) INFORMATION FOR SEQ ID NO: 11:

(i) SEQUENCE CHARACTERISTICS:
        (A) LENGTH: 1640 base pairs
        (B) TYPE: nucleic acid
        (C) STRANDEDNESS: single
        (D) TOPOLOGY: linear (ii) MOLECULE TYPE: cDNA to mRNA (ix) FEATURE:
        (A) NAME/KEY: cDNA MAGE-3

(xi) SEQUENCE DESCRIPTION: SEQ ID NO: 11:

```
GCCGCGAGGG AAGCCGGCCC AGGCTCGGTG AGGAGGCAAG GTTCTGAGGG          50
GACAGGCTGA CCTGGAGGAC CAGAGGCCCC CGGAGGAGCA CTGAAGGAGA         100
AGATCTGCCA GTGGGTCTCC ATTGCCCAGC TCCTGCCCAC ACTCCCGCCT         150
GTTGCCCTGA CCAGAGTCAT C                                       171
ATG CCT CTT GAG CAG AGG AGT CAG CAC TGC AAG CCT GAA GAA        213
GGC CTT GAG GCC CGA GGA GAG GCC CTG GGC CTG GTG GGT GCG        255
CAG GCT CCT GCT ACT GAG GAG CAG GAG GCT GCC TCC TCC TCT        297
TCT ACT CTA GTT GAA GTC ACC CTG GGG GAG GTG CCT GCT GCC        339
GAG TCA CCA GAT CCT CCC CAG AGT CCT CAG GGA GCC TCC AGC        381
CTC CCC ACT ACC ATG AAC TAC CCT CTC TGG AGC CAA TCC TAT        423
GAG GAC TCC AGC AAC CAA GAA GAG GAG GGG CCA AGC ACC TTC        465
CCT GAC CTG GAG TCC GAG TTC CAA GCA GCA CTC AGT AGG AAG        507
GTG GCC GAG TTG GTT CAT TTT CTG CTC CTC AAG TAT CGA GCC        549
AGG GAG CCG GTC ACA AAG GCA GAA ATG CTG GGG AGT GTC GTC        591
GGA AAT TGG CAG TAT TTC TTT CCT GTG ATC TTC AGC AAA GCT        633
```

-continued

```
TCC AGT TCC TTG CAG CTG GTC TTT GGC ATC GAG CTG ATG GAA        675

GTG GAC CCC ATC GGC CAC TTG TAC ATC TTT GCC ACC TGC CTG        717

GGC CTC TCC TAC GAT GGC CTG CTG GGT GAC AAT CAG ATC ATG        759

CCC AAG GCA GGC CTC CTG ATA ATC GTC CTG GCC ATA ATC GCA        801

AGA GAG GGC GAC TGT GCC CCT GAG GAG AAA ATC TGG GAG GAG        843

CTG AGT GTG TTA GAG GTG TTT GAG GGG AGG GAA GAC AGT ATG        885

TTG GGG GAT CCC AAG AAG CTG CTC ACC CAA CAT TTC GTG CAG        927

GAA AAC TAC CTG GAG TAC CGG CAG GTC CCC GGC AGT GAT CCT        969

GCA TGT TAT GAA TTC CTG TGG GGT CCA AGG GCC CTC GTT GAA       1011

ACC AGC TAT GTG AAA GTC CTG CAC CAT ATG GTA AAG ATC AGT       1053

GGA GGA CCT CAC ATT TCC TAC CCA CCC CTG CAT GAG TGG GTT       1095

TTG AGA GAG GGG GAA GAG TGA                                   1116

GTCTGAGCAC GAGTTGCAGC CAGGGCCAGT GGGAGGGGGT CTGGGCCAGT        1166

GCACCTTCCG GGGCCGCATC CCTTAGTTTC CACTGCCTCC TGTGACGTGA        1216

GGCCCATTCT TCACTCTTTG AAGCGAGCAG TCAGCATTCT TAGTAGTGGG        1266

TTTCTGTTCT GTTGGATGAC TTTGAGATTA TTCTTTGTTT CCTGTTGGAG        1316

TTGTTCAAAT GTTCCTTTTA ACGGATGGTT GAATGAGCGT CAGCATCCAG        1366

GTTTATGAAT GACAGTAGTC ACACATAGTG CTGTTTATAT AGTTTAGGAG        1416

TAAGAGTCTT GttTTTTACT CAAATTgGGA AATCCATTCC ATTTTGTGAA        1466

TTGTGACATA ATAATAGCAG TGGTAAAAGT ATTTGCTTAA AATTGTGAGC        1516

GAATTAGCAA TAACATACAT GAGATAACTC AAGAAATCAA AAGATAGTTG        1566

ATTCTTGCCT TGTACCTCAA TCTATTCTGT AAAATTAAAC AAATATGCAA        1616

ACCAGGATTT CCTTGACTTC TTTG                                    1640
```

(2) INFORMATION FOR SEQ ID NO: 12:

(i) SEQUENCE CHARACTERISTICS:
        (A) LENGTH: 943 base pairs
        (B) TYPE: nucleic acid
        (C) STRANDEDNESS: single
        (D) TOPOLOGY: linear (ii) MOLECULE TYPE: genomic DNA (ix) FEATURE:
        (A) NAME/KEY: MAGE-31 gene (xi) SEQUENCE DESCRIPTION: SEQ ID NO: 12:

```
GGATCCTCCA CCCCAGTAGA GTGGGGACCT CACAGAGTCT GGCCAACCCT          50

CCTGACAGTT CTGGGAATCC GTGGCTGCGT TTGCTGTCTG CACATTGGGG         100

GCCCGTGGAT TCCTCTCCCA GGAATCAGGA GCTCCAGGAA CAAGGCAGTG         150

AGGACTTGGT CTGAGGCAGT GTCCTCAGGT CACAGAGTAG AGGGGgCTCA         200

GATAGTGCCA ACGGTGAAGG TTTGCCTTGG ATTCAAACCA AGGGCCCCAC         250

CTGCCCCAGA ACACATGGAC TCCAGAGCGC CTGGCCTCAC CCTCAATACT         300

TTCAGTCCTG CAGCCTCAGC ATGCGCTGGC CGGATGTACC CTGAGGTGCC         350

CTCTCACTTC TCCCTTCAGG TTCTGAGGGG ACAGGCTGAC CTGGAGGACC         400

AGAGGCCCCC GGAGGAGCAC TGAAGGAGAA GATCTGTAAG TAAGCCTTTG         450
```

-continued

```
TTAGAGCCTC CAAGGTTCCA TTCAGTACTC AGCTGAGGTC TCTCACATGC        500

TCCCTCTCTC CCCAGGCCAG TGGGTCTCCA TTGCCCAGCT CCTGCCCACA        550

CTCCCGCCTG TTGCCCTGAC CAGAGTCATC                              580

ATG CCT CTT GAG CAG AGG AGT CAG CAC TGC AAG CCT GAA GAA       622

GGC CTT GAG GCC CGA GGA GAg GCC CTG GGC CTG GTG GGT GCG       664

CAG GCT CCT GCT ACT GAG GAG CAG GAG GCT GCC TCC TCC TCT       706

TCT AGT GTA GTT GAA GTC ACC CTG GGG GAG GTG CCT GCT GCC       748

GAG TCA CCA GAT CCT CCC CAG AGT CCT CAG GGA GCC TCC AGC       790

CTC CCC ACT ACC ATG AAC TAC CCT CTC TGG AGC CAA TCC TAT       832

GAG GAC TCC AGC AAC CAA GAA GAG GAG GGG CCA AGC ACC TTC       874

CCT GAC CTG GAG TCT GAG TTC CAA GCA GCA CTC AGT AGG AAG       916

GTG GCC AAG TTG GTT CAT TTT CTG CTC                           943
```

(2) INFORMATION FOR SEQ ID NO: 13:

(i) SEQUENCE CHARACTERISTICS:
        (A) LENGTH:  2531 base pairs
        (B) TYPE:  nucleic acid
        (C) STRANDEDNESS: single
        (D) TOPOLOGY:  linear (ii) MOLECULE TYPE:  genomic DNA (ix) FEATURE:
        (A) NAME/KEY:  MAGE-4 gene (xi) SEQUENCE DESCRIPTION:  SEQ ID NO: 13:

```
GGATCCAGGC CCTGCCTGGA GAAATGTGAG GGCCCTGAGT GAACACAGTG         50

GGGATCATCC ACTCCATGAG AGTGGGGACC TCACAGAGTC CAGCCTACCC        100

TCTTGATGGC ACTGAGGGAC CGGGGCTGTG CTTACAGTCT GCACCCTAAG        150

GGCCCATGGA TTCCTCTCCT AGGAGCTCCA GGAACAAGGC AGTGAGGCCT        200

TGGTCTGAGA CAGTGTCCTC AGGTTACAGA GCAGAGGATG CACAGGCTGT        250

GCCAGCAGTG AATGTTTGCC CTGAATGCAC ACCAAGGGCC CCACCTGCCA        300

CAAGACACAT AGGACTCCAA AGAGTCTGGC CTCACCTCCC TACCATCAAT        350

CCTGCAGAAT CGACCTCTGC TGGCCGGCTA TACCCTGAGG TGCTCTCTCA        400

CTTCCTCCTT CAGGTTCTGA GCAGACAGGC CAACCGGAGA CAGGATTCCC        450

TGGAGGCCAC AGAGGAGCAC CAAGGAGAAG ATCTGTAAGT AAGCCTTTGT        500

TAGAGCCTCT AAGATTTGGT TCTCAGCTGA GGTCTCTCAC ATGCTCCCTC        550

TCTCCGTAGG CCTGTGGGTC CCCATTGCCC AGCTTTTGCC TGCACTCTTG        600

CCTGCTGCCC TGACCAGAGT CATC                                    624

ATG TCT TCT GAG CAG AAG AGT CAG CAC TGC AAG CCT GAG GAA       666

GGC GTT GAG GCC CAA GAA GAG GCC CTG GGC CTG GTG GGT GCA       708

CAG GCT CCT ACT ACT GAG GAG CAG GAG GCT GCT GTC TCC TCC       750

TCC TCT CCT CTG GTC CCT GGC ACC CTG GAG GAA GTG CCT GCT       792

GCT GAG TCA GCA GGT CCT CCC CAG AGT CCT CAG GGA GCC TCT       834

GCC TTA CCC ACT ACC ATC AGC TTC ACT TGC TGG AGG CAA CCC       876

AAT GAG GGT TCC AGC AGC CAA GAA GAG GAG GGG CCA AGC ACC       918
```

| | |
|---|---|
| TCG CCT GAC GCA GAG TCC TTG TTC CGA GAA GCA CTC AGT AAC | 960 |
| AAG GTG GAT GAG TTG GCT CAT TTT CTG CTC CGC AAG TAT CGA | 1002 |
| GCC AAG GAG CTG GTC ACA AAG GCA GAA ATG CTG GAG AGA GTC | 1044 |
| ATC AAA AAT TAC AAG CGC TGC TTT CCT GTG ATC TTC GGC AAA | 1086 |
| GCC TCC GAG TCC CTG AAG ATG ATC TTT GGC ATT GAC GTG AAG | 1128 |
| GAA GTG GAC CCC GCC AGC AAC ACC TAC ACC CTT GTC ACC TGC | 1170 |
| CTG GGC CTT TCC TAT GAT GGC CTG CTG GGT AAT AAT CAG ATC | 1212 |
| TTT CCC AAG ACA GGC CTT CTG ATA ATC GTC CTG GGC ACA ATT | 1254 |
| GCA ATG GAG GGC GAC AGC GCC TCT GAG GAG GAA ATC TGG GAG | 1296 |
| GAG CTG GGT GTG ATG GGG GTG TAT GAT GGG AGG GAG CAC ACT | 1338 |
| GTC TAT GGG GAG CCC AGG AAA CTG CTC ACC CAA GAT TGG GTG | 1380 |
| CAG GAA AAC TAC CTG GAG TAC CGG CAG GTA CCC GGC AGT AAT | 1422 |
| CCT GCG CGC TAT GAG TTC CTG TGG GGT CCA AGG GCT CTG GCT | 1464 |
| GAA ACC AGC TAT GTG AAA GTC CTG GAG CAT GTG GTC AGG GTC | 1506 |
| AAT GCA AGA GTT CGC ATT GCC TAC CCA TCC CTG CGT GAA GCA | 1548 |
| GCT TTG TTA GAG GAG GAA GAG GGA GTC TGA | 1578 |
| GCATGAGTTG CAGCCAGGGC TGTGGGAAG GGGCAGGGCT GGGCCAGTGC | 1628 |
| ATCTAACAGC CCTGTGCAGC AGCTTCCCTT GCCTCGTGTA ACATGAGGCC | 1678 |
| CATTCTTCAC TCTGTTTGAA GAAAATAGTC AGTGTTCTTA GTAGTGGGTT | 1728 |
| TCTATTTTGT TGGATGACTT GGAGATTTAT CTCTGTTTCC TTTTACAATT | 1778 |
| GTTGAAATGT TCCTTTTAAT GGATGGTTGA ATTAACTTCA GCATCCAAGT | 1828 |
| TTATGAATCG TAGTTAACGT ATATTGCTGT TAATATAGTT TAGGAGTAAG | 1878 |
| AGTCTTGTTT TTTATTCAGA TTGGGAAATC CGTTCTATTT TGTGAATTTG | 1928 |
| GGACATAATA ACAGCAGTGG AGTAAGTATT TAGAAGTGTG AATTCACCGT | 1978 |
| GAAATAGGTG AGATAAATTA AAAGATACTT AATTCCCGCC TTATGCCTCA | 2028 |
| GTCTATTCTG TAAAATTTAA AAATATATAT GCATACCTGG ATTTCCTTGG | 2078 |
| CTTCGTGAAT GTAAGAGAAA TTAAATCTGA ATAAATAATT CTTTCTGTTA | 2128 |
| ACTGGCTCAT TTCTTCTCTA TGCACTGAGC ATCTGCTCTG TGGAAGGCCC | 2178 |
| AGGATTAGTA GTGGAGATAC TAGGGTAAGC CAGACACACA CCTACCGATA | 2228 |
| GGGTATTAAG AGTCTAGGAG CGCGGTCATA TAATTAAGGT GACAAGATGT | 2278 |
| CCTCTAAGAT GTAGGGGAAA AGTAACGAGT GTGGGTATGG GGCTCCAGGT | 2328 |
| GAGAGTGGTC GGGTGTAAAT TCCCTGTGTG GGGCCTTTTG GGCTTTGGGA | 2378 |
| AACTGCATTT TCTTCTGAGG GATCTGATTC TAATGAAGCT TGGTGGGTCC | 2428 |
| AGGGCCAGAT TCTCAGAGGG AGAGGGAAAA GCCCAGATTG GAAAAGTTGC | 2478 |
| TCTGAGCAGT TCCTTTGTGA CAATGGATGA ACAGAGAGGA GCCTCTACCT | 2528 |
| GGG | 2531 |

(2) INFORMATION FOR SEQ ID NO: 14:

(i) SEQUENCE CHARACTERISTICS:
        (A) LENGTH: 2531 base pairs
        (B) TYPE: nucleic acid
        (C) STRANDEDNESS: single
        (D) TOPOLOGY: linear (ii) MOLECULE TYPE: genomic DNA (ix) FEATURE:
  (A) NAME/KEY: MAGE-41 gene (xi) SEQUENCE DESCRIPTION: SEQ ID NO: 14:

| | |
|---|---:|
| GGATCCAGGC CCTGCCTGGA GAAATGTGAG GGCCCTGAGT GAACACAGTG | 50 |
| GGGATCATCC ACTCCATGAG AGTGGGGACC TCACAGAGTC CAGCCTACCC | 100 |
| TCTTGATGGC ACTGAGGGAC CGGGGCTGTG CTTACAGTCT GCACCCTAAG | 150 |
| GGCCCATGGA TTCCTCTCCT AGGAGCTCCA GGAACAAGGC AGTGAGGCCT | 200 |
| TGGTCTGAGA CAGTGTCCTC AGGTTACAGA GCAGAGGATG CACAGGCTGT | 250 |
| GCCAGCAGTG AATGTTTGCC CTGAATGCAC ACCAAGGGCC CCACCTGCCA | 300 |
| CAAGACACAT AGGACTCCAA AGAGTCTGGC CTCACCTCCC TACCATCAAT | 350 |
| CCTGCAGAAT CGACCTCTGC TGGCCGGCTA TACCCTGAGG TGCTCTCTCA | 400 |
| CTTCCTCCTT CAGGTTCTGA GCAGACAGGC CAACCGGAGA CAGGATTCCC | 450 |
| TGGAGGCCAC AGAGGAGCAC CAAGGAGAAG ATCTGTAAGT AAGCCTTTGT | 500 |
| TAGAGCCTCT AAGATTTGGT TCTCAGCTGA GGTCTCTCAC ATGCTCCCTC | 550 |
| TCTCCGTAGG CCTGTGGGTC CCCATTGCCC AGCTTTTGCC TGCACTCTTG | 600 |
| CCTGCTGCCC TGAGCAGAGT CATC | 624 |
| ATG TCT TCT GAG CAG AAG AGT CAG CAC TGC AAG CCT GAG GAA | 666 |
| GGC GTT GAG GCC CAA GAA GAG GCC CTG GGC CTG GTG GGT GCG | 708 |
| CAG GCT CCT ACT ACT GAG GAG CAG GAG GCT GCT GTC TCC TCC | 750 |
| TCC TCT CCT CTG GTC CCT GGC ACC CTG GAG GAA GTG CCT GCT | 792 |
| GCT GAG TCA GCA GGT CCT CCC CAG AGT CCT CAG GGA GCC TCT | 834 |
| GCC TTA CCC ACT ACC ATC AGC TTC ACT TGC TGG AGG CAA CCC | 876 |
| AAT GAG GGT TCC AGC AGC CAA GAA GAG GAG GGG CCA AGC ACC | 918 |
| TCG CCT GAC GCA GAG TCC TTG TTC CGA GAA GCA CTC AGT AAC | 960 |
| AAG GTG GAT GAG TTG GCT CAT TTT CTG CTC CGC AAG TAT CGA | 1002 |
| GCC AAG GAG CTG GTC ACA AAG GCA GAA ATG CTG GAG AGA GTC | 1044 |
| ATC AAA AAT TAC AAG CGC TGC TTT CCT GTG ATC TTC GGC AAA | 1086 |
| GCC TCC GAG TCC CTG AAG ATG ATC TTT GGC ATT GAC GTG AAG | 1128 |
| GAA GTG GAC CCC ACC AGC AAC ACC TAC ACC CTT GTC ACC TGC | 1170 |
| CTG GGC CTT TCC TAT GAT GGC CTG CTG GGT AAT AAT CAG ATC | 1212 |
| TTT CCC AAG ACA GGC CTT CTG ATA ATC GTC CTG GCA CAA ATT | 1254 |
| GCA ATG GAG GGC GAC AGC GCC TCT GAG GAG GAA ATC TGG GAG | 1296 |
| GAG CTG GGT GTG ATG GGG GTG TAT GAT GGG AGG GAG CAC ACT | 1338 |
| GTC TAT GGG GAG CCC AGG AAA CTG CTC ACC CAA GAT TGG GTG | 1380 |
| CAG GAA AAC TAC CTG GAG TAC CGG CAG GTA CCC GGC AGT AAT | 1422 |
| CCT GCG CGC TAT GAG TTC CTG TGG GGT CCA AGG GCT CTG GCT | 1464 |
| GAA ACC AGC TAT GTG AAA GTC CTG GAG CAT GTG GTC AGG GTC | 1506 |
| AAT GCA AGA GTT CGC ATT GCC TAC CCA TCC CTG CGT GAA GCA | 1548 |
| GCT TTG TTA GAG GAG GAA GAG GGA GTC TGA | 1578 |

```
GCATGAGTTG CAGCCAGGGC TGTGGGGAAG GGGCAGGGCT GGGCCAGTGC        1628

ATCTAACAGC CCTGTGCAGC AGCTTCCCTT GCCTCGTGTA ACATGAGGCC        1678

CATTCTTCAC TCTGTTTGAA GAAAATAGTC AGTGTTCTTA GTAGTGGGTT        1728

TCTATTTTGT TGGATGACTT GGAGATTTAT CTCTGTTTCC TTTTACAATT        1778

GTTGAAATGT TCCTTTTAAT GGATGGTTGA ATTAACTTCA GCATCCAAGT        1828

TTATGAATCG TAGTTAACGT ATATTGCTGT TAATATAGTT TAGGAGTAAG        1878

AGTCTTGTTT TTTATTCAGA TTGGGAAATC CGTTCTATTT TGTGAATTTG        1928

GGACATAATA ACAGCAGTGG AGTAAGTATT TAGAAGTGTG AATTCACCGT        1978

GAAATAGGTG AGATAAATTA AAAGATACTT AATTCCCGCC TTATGCCTCA        2028

GTCTATTCTG TAAAATTTAA AAATATATAT GCATACCTGG ATTTCCTTGG        2078

CTTCGTGAAT GTAAGAGAAA TTAAATCTGA ATAAATAATT CTTTCTGTTA        2128

ACTGGCTCAT TTCTTCTCTA TGCACTGAGC ATCTGCTCTG TGGAAGGCCC        2178

AGGATTAGTA GTGGAGATAC TAGGGTAAGC CAGACACACA CCTACCGATA        2228

GGGTATTAAG AGTCTAGGAG CGCGGTCATA TAATTAAGGT GACAAGATGT        2278

CCTCTAAGAT GTAGGGGAAA AGTAACGAGT GTGGGTATGG GGCTCCAGGT        2328

GAGAGTGGTC GGGTGTAAAT TCCCTGTGTG GGGCCTTTTG GGCTTTGGGA        2378

AACTCCATTT TCTTCTGAGG GATCTGATTC TAATGAAGCT TGGTGGGTCC        2428

AGGGCCAGAT TCTCAGAGGG AGAGGGAAAA GCCCAGATTG GAAAAGTTGC        2478

TCTGAGCGGT TCCTTTGTGA CAATGGATGA ACAGAGAGGA GCCTCTACCT        2528

GGG                                                          2531

(2) INFORMATION FOR SEQ ID NO: 15:

(i) SEQUENCE CHARACTERISTICS:
        (A) LENGTH: 1068 base pairs
        (B) TYPE: nucleic acid
        (C) STRANDEDNESS: single
        (D) TOPOLOGY: linear (ii) MOLECULE TYPE: cDNA to mRNA (ix) FEATURE:
        (A) NAME/KEY: cDNA MAGE-4

(xi) SEQUENCE DESCRIPTION: SEQ ID NO: 15:

G GGG CCA AGC ACC TCG CCT GAC GCA GAG TCC TTG TTC CGA          40

GAA GCA CTC AGT AAC AAG GTG GAT GAG TTG GCT CAT TTT CTG        82

CTC CGC AAG TAT CGA GCC AAG GAG CTG GTC ACA AAG GCA GAA       124

ATG CTG GAG AGA GTC ATC AAA AAT TAC AAG CGC TGC TTT CCT       166

GTG ATC TTC GGC AAA GCC TCC GAG TCC CTG AAG ATG ATC TTT       208

GGC ATT GAC GTG AAG GAA GTG GAC CCC GCC AGC AAC ACC TAC       250

ACC CTT GTC ACC TGC CTG GGC CTT TCC TAT GAT GGC CTG CTG       292

GGT AAT AAT CAG ATC TTT CCC AAG ACA GGC CTT CTG ATA ATC       334

GTC CTG GGC ACA ATT GCA ATG GAG GGC GAC AGC GCC TCT GAG       376

GAG GAA ATC TGG GAG GAG CTG GGT GTG ATG GGG GTG TAT GAT       418

GGG AGG GAG CAC ACT GTC TAT GGG GAG CCC AGG AAA CTG CTC       460

ACC CAA GAT TGG GTG CAG GAA AAC TAC CTG GAG TAC CGG CAG       502
```

-continued

| | |
|---|---|
| GTA CCC GGC AGT AAT CCT GCG CGC TAT GAG TTC CTG TGG GGT | 544 |
| CCA AGG GCT CTG GCT GAA ACC AGC TAT GTG AAA GTC CTG GAG | 586 |
| CAT GTG GTC AGG GTC AAT GCA AGA GTT CGC ATT GCC TAC CCA | 628 |
| TCC CTG CGT GAA GCA GCT TTG TTA GAG GAG GAA GAG GGA GTC | 670 |
| TGAGCATGAG TTGCAGCCAG GGCTGTGGGG AAGGGGCAGG GCTGGGCCAG | 720 |
| TGCATCTAAC AGCCCTGTGC AGCAGCTTCC CTTGCCTCGT GTAACATGAG | 770 |
| GCCCATTCTT CACTCTGTTT GAAGAAAATA GTCAGTGTTC TTAGTAGTGG | 820 |
| GTTTCTATTT TGTTGGATGA CTTGGAGATT TATCTCTGTT TCCTTTTACA | 870 |
| ATTGTTGAAA TGTTCCTTTT AATGGATGGT TGAATTAACT TCAGCATCCA | 920 |
| AGTTTATGAA TCGTAGTTAA CGTATATTGC TGTTAATATA GTTTAGGAGT | 970 |
| AAGAGTCTTG TTTTTTATTC AGATTGGGAA ATCCGTTCTA TTTTGTGAAT | 1020 |
| TTGGGACATA ATAACAGCAG TGGAGTAAGT ATTTAGAAGT GTGAATTC | 1068 |

(2) INFORMATION FOR SEQ ID NO: 16:
    (i) SEQUENCE CHARACTERISTICS:
        (A) LENGTH: 2226 base pairs
        (B) TYPE: nucleic acid
        (C) STRANDEDNESS: single
        (D) TOPOLOGY: linear (ii) MOLECULE TYPE: genomic DNA (ix) FEATURE:
        (A) NAME/KEY: MAGE-5 gene (xi) SEQUENCE DESCRIPTION: SEQ ID NO: 16:

| | |
|---|---|
| GGATCCAGGC CTTGCCAGGA GAAAGGTGAG GGCCCTGTGT GAGCACAGAG | 50 |
| GGACCATTC ACCCCAAGAG GGTGGAGACC TCACAGATTC CAGCCTACCC | 100 |
| TCCTGTTAGC ACTGGGGGCC TGAGGCTGTG CTTGCAGTCT GCACCCTGAG | 150 |
| GGCCCATGCA TTCCTCTTCC AGGAGCTCCA GGAAACAGAC ACTGAGGCCT | 200 |
| TGGTCTGAGG CCGTGCCCTC AGGTCACAGA GCAGAGGAGA TGCAGACGTC | 250 |
| TAGTGCCAGC AGTGAACGTT TGCCTTGAAT GCACACTAAT GGCCCCCATC | 300 |
| GCCCCAGAAC ATATGGGACT CCAGAGCACC TGGCCTCACC CTCTCTACTG | 350 |
| TCAGTCCTGC AGAATCAGCC TCTGCTTGCT TGTGTACCCT GAGGTGCCCT | 400 |
| CTCACTTTTT CCTTCAGGTT CTCAGGGGAC AGGCTGACCA GGATCACCAG | 450 |
| GAAGCTCCAG AGGATCCCCA GGAGGCCCTA GAGGAGCACC AAAGGAGAAG | 500 |
| ATCTGTAAGT AAGCCTTTGT TAGAGCCTCC AAGGTTCAGT TTTTAGCTGA | 550 |
| GGCTTCTCAC ATGCTCCCTC TCTCTCCAGG CCAGTGGGTC TCCATTGCCC | 600 |
| AGCTCCTGCC CACACTCCTG CCTGTTGCGG TGACCAGAGT CGTC | 644 |
| ATG TCT CTT GAG CAG AAG AGT CAG CAC TGC AAG CCT GAG GAA | 686 |
| CTC CTC TGG TCC CAG GCA CCC TGG GGG AGG TGC CTG CTG CTG | 728 |
| GGT CAC CAG GTC CTC TCA AGA GTC CTC AGG GAG CCT CCG CCA | 770 |
| TCC CCA CTG CCA TCG ATT TCA CTC TAT GGA GGC AAT CCA TTA | 812 |
| AGG GCT CCA GCA ACC AAG AAG AGG AGG GGC CAA GCA CCT CCC | 854 |
| CTG ACC CAG AGT CTG TGT TCC GAG CAG CAC TCA GTA AGA AGG | 896 |
| TGG CTG ACT TGA | 908 |
| TTCATTTTCT GCTCCTCAAG TATTAAGTCA AGGAGCTGGT CACAAAGGCA | 958 |

```
GAAATGCTGG AGAGCGTCAT CAAAAATTAC AAGCGCTGCT TTCCTGAGAT        1008

CTTCGGCAAA GCCTCCGAGT CCTTGCAGCT GGTCTTTGGC ATTGACGTGA        1058

AGGAAGCGGA CCCCACCAGC AACACCTACA CCCTTGTCAC CTGCCTGGGA        1108

CTCCTATGAT GGCCTGCTGG TTGATAATAA TCAGATCATG CCCAAGACGG        1158

GCCTCCTGAT AATCGTCTTG GCATGATTG CAATGGAGGG CAAATGCGTC         1208

CCTGAGGAGA AAATCTGGGA GGAGCTGAGT GTGATGAAGG TGTATGTTGG        1258

GAGGGAGCAC AGTGTCTGTG GGGAGCCCAG GAAGCTGCTC ACCCAAGATT        1308

TGGTGCAGGA AAACTACCTG GAGTACCGGC AGGTGCCCAG CAGTGATCCC        1358

ATATGCTATG AGTTACTGTG GGGTCCAAGG GCACTCGCTG CTTGAAAGTA        1408

CTGGAGCACG TGGTCAGGGT CAATGCAAGA GTTCTCATTT CCTACCCATC        1458

CCTGCGTGAA GCAGCTTTGA GAGGAGGA AGAGGGAGTC TGAGCATGAG          1508

CTGCAGCCAG GGCCACTGCG AGGGGGCTG GGCCAGTGCA CCTTCCAGGG         1558

CTCCGTCCAG TAGTTTCCCC TGCCTTAATG TGACATGAGG CCCATTCTTC        1608

TCTCTTTGAA GAGAGCAGTC AACATTCTTA GTAGTGGGTT TCTGTTCTAT        1658

TGGATGACTT TGAGATTTGT CTTTGTTTCC TTTTGGAATT GTTCAAATGT        1708

TTCTTTTAAT GGGTGGTTGA ATGAACTTCA GCATTCAAAT TTATGAATGA        1758

CAGTAGTCAC ACATAGTGCT GTTTATATAG TTTAGGAGTA AGAGTCTTGT        1808

TTTTTATTCA GATTGGGAAA TCCATTCCAT TTTGTGAATT GGGACATAGT        1858

TACAGCAGTG GAATAAGTAT TCATTTAGAA ATGTGAATGA GCAGTAAAAC        1908

TGATGACATA AAGAAATTAA AAGATATTTA ATTCTTGCTT ATACTCAGTC        1958

TATTCGGTAA AATTTTTTTT AAAAAATGTG CATACCTGGA TTTCCTTGGC        2008

TTCTTTGAGA ATGTAAGACA AATTAAATCT GAATAAATCA TTCTCCCTGT        2058

TCACTGGCTC ATTTATTCTC TATGCACTGA GCATTTGCTC TGTGGAAGGC        2108

CCTGGGTTAA TAGTGGAGAT GCTAAGGTAA GCCAGACTCA CCCCTACCCA        2158

CAGGGTAGTA AAGTCTAGGA GCAGCAGTCA TATAATTAAG GTGGAGAGAT        2208

GCCCTCTAAG ATGTAGAG                                          2226
```

(2) INFORMATION FOR SEQ ID NO: 17:

(i) SEQUENCE CHARACTERISTICS:
        (A) LENGTH:  2305 base pairs
        (B) TYPE:  nucleic acid
        (C) STRANDEDNESS: single
        (D) TOPOLOGY:  linear (ii) MOLECULE TYPE:  genomic DNA (ix) FEATURE:
        (A) NAME/KEY:  MAGE-51 gene (xi) SEQUENCE DESCRIPTION:  SEQ ID NO: 17:

```
GGATCCAGGC CTTGCCAGGA GAAAGGTGAG GGCCCTGTGT GAGCACAGAG         50

GGGACCATTC ACCCCAAGAG GGTGGAGACC TCACAGATTC CAGCCTACCC        100

TCCTGTTAGC ACTGGGGGCC TGAGGCTGTG CTTGCAGTCT GCACCCTGAG        150

GGCCCATGCA TTCCTCTTCC AGGAGCTCCA GGAAACAGAC ACTGAGGCCT        200

TGGTCTGAGG CCGTGCCCTC AGGTCACAGA GCAGAGGAGA TGCAGACGTC        250

TAGTGCCAGC AGTGAACGTT TGCCTTGAAT GCACACTAAT GGCCCCCATC        300
```

```
GCCCCAGAAC ATATGGGACT CCAGAGCACC TGGCCTCACC CTCTCTACTG       350

TCAGTCCTGC AGAATCAGCC TCTGCTTGCT TGTGTACCCT GAGGTGCCCT       400

CTCACTTTTT CCTTCAGGTT CTCAGGGAC AGGCTGACCA GGATCACCAG        450

GAAGCTCCAG AGGATCCCCA GGAGGCCCTA GAGGAGCACC AAAGGAGAAG       500

ATCTGTAAGT AAGCCTTTGT TAGAGCCTCC AAGGTTCAGT TTTTAGCTGA       550

GGCTTCTCAC ATGCTCCCTC TCTCTCCAGG CCAGTGGGTC TCCATTGCCC       600

AGCTCCTGCC CACACTCCTG CCTGTTGCGG TGACCAGAGT CGTC             644

ATG TCT CTT GAG CAG AAG AGT CAG CAC TGC AAG CCT GAG GAA      686

GGC CTT GAC ACC CAA GAA GAG CCC TGG GCC TGG TGG GTG TGC      728

AGG CTG CCA CTA CTG AGG AGC AGG AGG CTG TGT CCT CCT CCT      770

CTC CTC TGG TCC CAG GCA CCC TGG GGG AGG TGC CTG CTG CTG      812

GGT CAC CAG GTC CTC TCA AGA GTC CTC AGG GAG CCT CCG CCA      854

TCC CCA CTG CCA TCG ATT TCA CTC TAT GGA GGC AAT CCA TTA      896

AGG GCT CCA GCA ACC AAG AAG AGG AGG GGC CAA GCA CCT CCC      938

CTG ACC CAG AGT CTG TGT TCC GAG CAG CAC TCA GTA AGA AGG      980

TGG CTG ACT TGA                                              992

TTCATTTTCT GCTCCTCAAG TATTAAGTCA AGGAGCCGGT CACAAAGGCA       1042

GAAATGCTGG AGAGCGTCAT CAAAAATTAC AAGCGCTGCT TCCTGAGAT        1092

CTTCGGCAAA GCCTCCGAGT CCTTGCAGCT GGTCTTTGGC ATTGACGTGA       1142

AGGAAGCGGA CCCCACCAGC AACACCTACA CCCTTGTCAC CTGCCTGGGA       1192

CTCCTATGAT GGCCTGGTGG TTTAATCAGA TCATGCCCAA GACGGGCCTC       1242

CTGATAATCG TCTTGGGCAT GATTGCAATG GAGGGCAAAT GCGTCCCTGA       1292

GGAGAAAATC TGGGAGGAGC TGGGTGTGAT GAAGGTGTAT GTTGGGAGGG       1342

AGCACAGTGT CTGTGGGGAG CCCAGGAAGC TGCTCACCCA AGATTTGGTG       1392

CAGGAAAACT ACCTGGAGTA CCGCAGGTGC CCAGCAGTGA TCCCATATGC       1442

TATGAGTTAC TGTGGGGTCC AAGGGCACTC GCTGCTTGAA AGTACTGGAG       1492

CACGTGGTCA GGGTCAATGC AAGAGTTCTC ATTTCCTACC CATCCCTGCA       1542

TGAAGCAGCT TTGAGAGAGG AGGAAGAGGG AGTCTGAGCA TGAGCTGCAG       1592

CCAGGGCCAC TGCGAGGGGG GCTGGGCCAG TGCACCTTCC AGGGCTCCGT       1642

CCAGTAGTTT CCCCTGCCTT AATGTGACAT GAGGCCCATT CTTCTCTCTT       1692

TGAAGAGAGC AGTCAACATT CTTAGTAGTG GGTTTCTGTT CTATTGGATG       1742

ACTTTGAGAT TTGTCTTTGT TTCCTTTTGG AATTGTTCAA ATGTTCCTTT       1792

TAATGGGTGG TTGAATGAAC TTCAGCATTC AAATTTATGA ATGACAGTAG       1842

TCACACATAG TGCTGTTTAT ATAGTTTAGG AGTAAGAGTC TTGTTTTTTA       1892

TTCAGATTGG GAAATCCATT CCATTTTGTG AATTGGGACA TAGTTACAGC       1942

AGTGGAATAA GTATTCATTT AGAAATGTGA ATGAGCAGTA AAACTGATGA       1992

GATAAAGAAA TTAAAGATA TTTAATTCTT GCCTTATACT CAGTCTATTC        2042

GGTAAAATTT TTTTTAAAA ATGTGCATAC CTGGATTTCC TTGGCTTCTT        2092

TGAGAATGTA AGACAAATTA AATCTGAATA AATCATTCTC CCTGTTCACT       2142

GGCTCATTTA TTCTCTATGC ACTGAGCATT TGCTCTGTGG AAGGCCCTGG      2192
```

```
GTTAATAGTG GAGATGCTAA GGTAAGCCAG ACTCACCCCT ACCCACAGGG           2242

TAGTAAAGTC TAGGAGCAGC AGTCATATAA TTAAGGTGGA GAGATGCCCT           2292

CTAAGATGTA GAG                                                   2305

(2) INFORMATION FOR SEQ ID NO: 18:

(i) SEQUENCE CHARACTERISTICS:
        (A) LENGTH:   225 base pairs
        (B) TYPE:     nucleic acid
        (C) STRANDEDNESS: single
        (D) TOPOLOGY: linear (ii) MOLECULE TYPE: cDNA (ix) FEATURE:
        (A) NAME/KEY: MAGE-6 gene (xi) SEQUENCE DESCRIPTION: SEQ ID NO: 18:

TAT TTC TTT CCT GTG ATC TTC AGC AAA GCT TCC GAT TCC TTG            42

CAG CTG GTC TTT GGC ATC GAG CTG ATG GAA GTG GAC CCC ATC            84

GGC CAC GTG TAC ATC TTT GCC ACC TGC CTG GGC CTC TCC TAC           126

GAT GGC CTG CTG GGT GAC AAT CAG ATC ATG CCC AGG ACA GGC           168

TTC CTG ATA ATC ATC CTG GCC ATA ATC GCA AGA GAG GGC GAC           210

TGT GCC CCT GAG GAG                                               225

(2) INFORMATION FOR SEQ ID NO: 19:

(i) SEQUENCE CHARACTERISTICS:
        (A) LENGTH:   1947 base pairs
        (B) TYPE:     nucleic acid
        (C) STRANDEDNESS: single
        (D) TOPOLOGY: linear (ii) MOLECULE TYPE: genomic DNA (ix) FEATURE:
        (A) NAME/KEY: MAGE-7 gene (xi) SEQUENCE DESCRIPTION: SEQ ID NO: 19:

TGAATGGACA CAAGGGCCCC CACACTCCCC AGAACACAAG GGACTCCAGA             50

GAGCCCAGCC TCACCTTCCC TACTGTCAGT CCTGCAGCCT CAGCCTCTGC            100

TGGCCGGCTG TACCCTGAGG TGCCCTCTCA CTTCCTCCTT CAGGTTCTCA            150

GCGGACAGGC CGGCCAGGAG GTCAGAAGCC CCAGGAGGCC CCAGAGGAGC            200

ACCGAAGGAG AAGATCTGTA AGTAGGCCTT TGTTAGGGCC TCCAGGGCGT            250

GGTTCACAAA TGAGGCCCCT CACAAGCTCC TTCTCTCCCC AGATCTGTGG            300

GTTCCTCCCC ATCGCCCAGC TGCTGCCCGC ACTCCAGCCT GCTGCCCTGA            350

CCAGAGTCAT CATGTCTTCT GAGCAGAGGA GTCAGCACTG CAAGCCTGAG            400

GATGCCTTGA GGCCCAAGGA CAGGAGGCTC TGGGCCTGGT GGGTGCGCAG            450

GCTCCCGCCA CCGAGGAGCA CGAGGCTGCC TCCTCCTTCA CTCTGATTGA            500

AGGCACCCTG GAGGAGGTGC CTGCTGCTGG GTCCCCCAGT CCTCCCCTGA            550

GTCTCAGGGT TCCTCCTTTT CCCTGACCAT CAGCAACAAC ACTCTATGGA            600

GCCAATCCAG TGAGGGCACC AGCAGCCGGG AAGAGGAGGG GCCAACCACC            650

TAGACACACC CCGCTCACCT GGCGTCCTTG TTCCA                            685

ATG GGA AGG TGG CTG AGT TGG TTC GCT TCC TGC TGC ACA AGT           727
```

```
ATC GAG TCA AGG AGC TGG TCA CAA AGG CAG AAA TGC TGG ACA        769

GTG TCA TCA AAA ATT ACA AGC ACT AGT TTC CTT GTG ATC TAT        811

GGC AAA GCC TCA GAG TGC ATG CAG GTG ATG TTT GGC ATT GAC        853

ATG AAG GAA GTG GAC CCC GCG GCC ACT CCT ACG TCC TTG TCA        895

CCT GCT TGG GCC TCT CCT ACA ATG GCC TGC TGG GTG ATG ATC        937

AGA GCA TGC CCG AGA CCG GCC TTC TGA                            964

TTATGGTCTT GACCATGATC TTAATGGAGG GCCACTGTGC CCCTGAGGAG         1014

GCAATCTGGG AAGCGTTGAG TGTAATGGTG TATGATGGGA TGGAGCAGTT         1064

TCTTTGGGCA GCTGAGGAAG CTGCTCACCC AAGATTGGGT GCAGGAAAAC         1114

TACCTGCAAT ACCGCCAGGT GCCCAGCAGT GATCCCCCGT GCTACCAGTT         1164

CCTGTGGGGT CCAAGGGCCC TCATTGAAAC CAGCTATGTG AAAGTCCTGG         1214

AGTATGCAGC CAGGGTCAGT ACTAAAGAGA GCATTTCCTA CCCATCCCTG         1264

CATGAAGAGG CTTTGGGAGA GGAGGAAGAG GGAGTCTGAG CAGAAGTTGC         1314

AGCCAGGGCC AGTGGGGCAG ATTGGGGGAG GGCCTGGGCA GTGCACGTTC         1364

CACACATCCA CCACCTTCCC TGTCCTGTTA CATGAGGCCC ATTCTTCACT         1414

CTGTGTTTGA AGAGAGCAGT CAATGTTCTC AGTAGCGGGG AGTGTGTTGG         1464

GTGTGAGGGA ATACAAGGTG GACCATCTCT CAGTTCCTGT TCTCTTGGGC         1514

GATTTGGAGG TTTATCTTTG TTTCCTTTTG CAGTCGTTCA AATGTTCCTT         1564

TTAATGGATG GTGTAATGAA CTTCAACATT CATTTCATGT ATGACAGTAG         1614

GCAGACTTAC TGTTTTTTAT ATAGTTAAAA GTAAGTGCAT TGTTTTTTAT         1664

TTATGTAAGA AAATCTATGT TATTTCTTGA ATTGGGACAA CATAACATAG         1714

CAGAGGATTA AGTACCTTTT ATAATGTGAA AGAACAAAGC GGTAAAATGG         1764

GTGAGATAAA GAAATAAAGA AATTAAATTG GCTGGGCACG GTGGCTCACG         1814

CCTGTAATCC CAGCACTTTA GGAGGCAGAG GCACGGGGAT CACGAGGTCA         1864

GGAGATCGAG ACCATTCTGG CTAACACAGT GAAACACCAT CTCTATTAAA         1914

AATACAAAAC TTAGCCGGGC GTGGTGGCGG GTG                           1947

(2) INFORMATION FOR SEQ ID NO: 20:

(i) SEQUENCE CHARACTERISTICS:
        (A) LENGTH:  1810 base pairs
        (B) TYPE:  nucleic acid
        (C) STRANDEDNESS: single
        (D) TOPOLOGY:  linear (ii) MOLECULE TYPE:  genomic DNA (ix) FEATURE:
        (A) NAME/KEY:  MAGE-8 gene (xi) SEQUENCE DESCRIPTION:  SEQ ID NO: 20:

GAGCTCCAGG AACCAGGCTG TGAGGTCTTG GTCTGAGGCA GTATCTTCAA           50

TCACAGAGCA TAAGAGGCCC AGGCAGTAGT AGCAGTCAAG CTGAGGTGGT          100

GTTTCCCCTG TATGTATACC AGAGGCCCCT CTGGCATCAG AACAGCAGGA          150

ACCCCACAGT TCCTGGCCCT ACCAGCCCTT TTGTCAGTCC TGGAGCCTTG          200

GCCTTTGCCA GGAGGCTGCA CCCTGAGATG CCCTCTCAAT TTCTCCTTCA          250

GGTTCGCAGA GAACAGGCCA GCCAGGAGGT CAGGAGGCCC CAGAGAAGCA          300
```

| | |
|---|---|
| CTGAAGAAGA CCTGTAAGTA GACCTTTGTT AGGGCATCCA GGGTGTAGTA | 350 |
| CCCAGCTGAG GCCTCTCACA CGCTTCCTCT CTCCCCAGGC CTGTGGGTCT | 400 |
| CAATTGCCCA GCTCCGGCCC ACACTCTCCT GCTGCCCTGA CCTGAGTCAT | 450 |
| C | 451 |
| ATG CTT CTT GGG CAG AAG AGT CAG CGC TAC AAG GCT GAG GAA | 493 |
| GGC CTT CAG GCC CAA GGA GAG GCA CCA GGG CTT ATG GAT GTG | 535 |
| CAG ATT CCC ACA GCT GAG GAG CAG AAG GCT GCA TCC TCC TCC | 577 |
| TCT ACT CTG ATC ATG GGA ACC CTT GAG GAG GTG ACT GAT TCT | 619 |
| GGG TCA CCA AGT CCT CCC CAG AGT CCT GAG GGT GCC TCC TCT | 661 |
| TCC CTG ACT GTC ACC GAC AGC ACT CTG TGG AGC CAA TCC GAT | 703 |
| GAG GGT TCC AGC AGC AAT GAA GAG GAG GGG CCA AGC ACC TCC | 745 |
| CCG GAC CCA GCT CAC CTG GAG TCC CTG TTC CGG GAA GCA CTT | 787 |
| GAT GAG AAA GTG GCT GAG TTA GTT CGT TTC CTG CTC CGC AAA | 829 |
| TAT CAA ATT AAG GAG CCG GTC ACA AAG GCA GAA ATG CTT GAG | 871 |
| AGT GTC ATC AAA AAT TAC AAG AAC CAC TTT CCT GAT ATC TTC | 913 |
| AGC AAA GCC TCT GAG TGC ATG CAG GTG ATC TTT GGC ATT GAT | 955 |
| GTG AAG GAA GTG GAC CCT GCC GGC CAC TCC TAC ATC CTT GTC | 997 |
| ACC TGC CTG GGC CTC TCC TAT GAT GGC CTG CTG GGT GAT GAT | 1039 |
| CAG AGT ACG CCC AAG ACC GGC CTC CTG ATA ATC GTC CTG GGC | 1081 |
| ATG ATC TTA ATG GAG GGC AGC CGC GCC CCG GAG GAG GCA ATC | 1123 |
| TGG GAA GCA TTG AGT GTG ATG GGG GCT GTA TGA | 1156 |
| TGGGAGGGAG CACAGTGTCT ATTGGAAGCT CAGGAAGCTG CTCACCCAAG | 1206 |
| AGTGGGTGCA GGAGAACTAC CTGGAGTACC GCCAGGCGCC CGGCAGTGAT | 1256 |
| CCTGTGCGCT ACGAGTTCCT GTGGGGTCCA AGGGCCCTTG CTGAAACCAG | 1306 |
| CTATGTGAAA GTCCTGGAGC ATGTGGTCAG GGTCAATGCA AGAGTTCGCA | 1356 |
| TTTCCTACCC ATCCCTGCAT GAAGAGGCTT TGGGAGAGGA GAAAGGAGTT | 1406 |
| TGAGCAGGAG TTGCAGCTAG GGCCAGTGGG GCAGGTTGTG GGAGGGCCTG | 1456 |
| GGCCAGTGCA CGTTCCAGGG CCACATCCAC CACTTTCCCT GCTCTGTTAC | 1506 |
| ATGAGGCCCA TTCTTCACTC TGTGTTTGAA GAGAGCAGTC ACAGTTCTCA | 1556 |
| GTAGTGGGGA GCATGTTGGG TGTGAGGGAA CACAGTGTGG ACCATCTCTC | 1606 |
| AGTTCCTGTT CTATTGGGCG ATTTGGAGGT TTATCTTTGT TTCCTTTTGG | 1656 |
| AATTGTTCCA ATGTTCCTTC TAATGGATGG TGTAATGAAC TTCAACATTC | 1706 |
| ATTTTATGTA TGACAGTAGA CAGACTTACT GCTTTTTATA TAGTTTAGGA | 1756 |
| GTAAGAGTCT TGCTTTTCAT TTATACTGGG AAACCCATGT TATTTCTTGA | 1806 |
| ATTC | 1810 |

(2) INFORMATION FOR SEQ ID NO: 21:
    (i) SEQUENCE CHARACTERISTICS:
        (A) LENGTH: 1412 base pairs
        (B) TYPE: nucleic acid
        (C) STRANDEDNESS: single
        (D) TOPOLOGY: linear (ii) MOLECULE TYPE: genomic DNA (ix) FEATURE:
    (A) NAME/KEY: MAGE-9 gene (xi) SEQUENCE DESCRIPTION: SEQ ID NO: 21:

| | |
|---|---|
| TCTGAGACAG TGTCCTCAGG TCGCAGAGCA GAGGAGACCC AGGCAGTGTC | 50 |
| AGCAGTGAAG GTGAAGTGTT CACCCTGAAT GTGCACCAAG GGCCCCACCT | 100 |
| GCCCCAGCAC ACATGGGACC CCATAGCACC TGGCCCCATT CCCCCTACTG | 150 |
| TCACTCATAG AGCCTTGATC TCTGCAGGCT AGCTGCACGC TGAGTAGCCC | 200 |
| TCTCACTTCC TCCCTCAGGT TCTCGGGACA GGCTAACCAG GAGGACAGGA | 250 |
| GCCCCAAGAG GCCCCAGAGC AGCACTGACG AAGACCTGTA AGTCAGCCTT | 300 |
| TGTTAGAACC TCCAAGGTTC GGTTCTCAGC TGAAGTCTCT CACACACTCC | 350 |
| CTCTCTCCCC AGGCCTGTGG GTCTCCATCG CCCAGCTCCT GCCCACGCTC | 400 |
| CTGACTGCTG CCCTGACCAG AGTCATC | 427 |
| ATG TCT CTC GAG CAG AGG AGT CCG CAC TGC AAG CCT GAT GAA | 469 |
| GAC CTT GAA GCC CAA GGA GAG GAC TTG GGC CTG ATG GGT GCA | 511 |
| CAG GAA CCC ACA GGC GAG GAG GAG GAG ACT ACC TCC TCC TCT | 553 |
| GAC AGC AAG GAG GAG GAG GTG TCT GCT GCT GGG TCA TCA AGT | 595 |
| CCT CCC CAG AGT CCT CAG GGA GGC GCT TCC TCC TCC ATT TCC | 637 |
| GTC TAC TAC ACT TTA TGG AGC CAA TTC GAT GAG GGC TCC AGC | 679 |
| AGT CAA GAA GAG GAA GAG CCA AGC TCC TCG GTC GAC CCA GCT | 721 |
| CAG CTG GAG TTC ATG TTC CAA GAA GCA CTG AAA TTG AAG GTG | 763 |
| GCT GAG TTG GTT CAT TTC CTG CTC CAC AAA TAT CGA GTC AAG | 805 |
| GAG CCG GTC ACA AAG GCA GAA ATG CTG GAG AGC GTC ATC AAA | 847 |
| AAT TAC AAG CGC TAC TTT CCT GTG ATC TTC GGC AAA GCC TCC | 889 |
| GAG TTC ATG CAG GTG ATC TTT GGC ACT GAT GTG AAG GAG GTG | 931 |
| GAC CCC GCC GGC CAC TCC TAC ATC CTT GTC ACT GCT CTT GGC | 973 |
| CTC TCG TGC GAT AGC ATG CTG GGT GAT GGT CAT AGC ATG CCC | 1015 |
| AAG GCC GCC CTC CTG ATC ATT GTC CTG GGT GTG ATC CTA ACC | 1057 |
| AAA GAC AAC TGC GCC CCT GAA GAG GTT ATC TGG GAA GCG TTG | 1099 |
| AGT GTG ATG GGG GTG TAT GTT GGG AAG GAG CAC ATG TTC TAC | 1141 |
| GGG GAG CCC AGG AAG CTG CTC ACC CAA GAT TGG GTG CAG GAA | 1183 |
| AAC TAC CTG GAG TAC CGG CAG GTG CCC GGC AGT GAT CCT GCG | 1225 |
| CAC TAC GAG TTC CTG TGG GGT TCC AAG GCC CAC GCT GAA ACC | 1267 |
| AGC TAT GAG AAG GTC ATA AAT TAT TTG GTC ATG CTC AAT GCA | 1309 |
| AGA GAG CCC ATC TGC TAC CCA TCC CTT TAT GAA GAG GTT TTG | 1351 |
| GGA GAG GAG CAA GAG GGA GTC TGA | 1375 |
| GCACCAGCCG CAGCCGGGGC AAAGTTTGT GGGGTCA | 1412 |

(2) INFORMATION FOR SEQ ID NO: 22:

(i) SEQUENCE CHARACTERISTICS:
        (A) LENGTH: 920 base pairs
        (B) TYPE: nucleic acid
        (C) STRANDEDNESS: single
        (D) TOPOLOGY: linear (ii) MOLECULE TYPE: genomic DNA (ix) FEATURE:
            (A) NAME/KEY: MAGE-10 gene (xi) SEQUENCE DESCRIPTION: SEQ ID NO: 22:

| | |
|---|---|
| ACCTGCTCCA GGACAAAGTG GACCCCACTG CATCAGCTCC ACCTACCCTA | 50 |
| CTGTCAGTCC TGGAGCCTTG GCCTCTGCCG GCTGCATCCT GAGGAGCCAT | 100 |
| CTCTCACTTC CTTCTTCAGG TTCTCAGGGG ACAGGGAGAG CAAGAGGTCA | 150 |
| AGAGCTGTGG GACACCACAG AGCAGCACTG AAGGAGAAGA CCTGTAAGTT | 200 |
| GGCCTTTGTT AGAACCTCCA GGGTGTGGTT CTCAGCTGTG GCCACTTACA | 250 |
| CCCTCCCTCT CTCCCCAGGC CTGTGGGTCC CCATCGCCCA AGTCCTGCCC | 300 |
| ACACTCCCAC CTGCTACCCT GATCAGAGTC ATC | 333 |
| ATG CCT CGA GCT CCA AAG CGT CAG CGC TGC ATG CCT GAA GAA | 375 |
| GAT CTT CAA TCC CAA AGT GAG ACA CAG GGC CTC GAG GGT GCA | 417 |
| CAG GCT CCC CTG GCT GTG GAG GAG GAT GCT TCA TCA TCC ACT | 459 |
| TCC ACC AGC TCC TCT TTT CCA TCC TCT TTT CCC TCC TCC TCC | 501 |
| TCT TCC TCC TCC TCC TCC TGC TAT CCT CTA ATA CCA AGC ACC | 543 |
| CCA GAG GAG GTT TCT GCT GAT GAT GAG ACA CCA AAT CCT CCC | 585 |
| CAG AGT GCT CAG ATA GCC TGC TCC TCC CCC TCG TCG TTG GCT | 627 |
| TCC CTT CCA TTA GAT CAA TCT GAT GAG GGC TCC AGC AGC CAA | 669 |
| AAG GAG GAG AGT CCA AGC ACC CTA CAG GTC CTG CCA GAC AGT | 711 |
| GAG TCT TTA CCC AGA AGT GAG ATA GAT GAA AAG GTG ACT GAT | 753 |
| TTG GTG CAG TTT CTG CTC TTC AAG TAT CAA ATG AAG GAG CCG | 795 |
| ATC ACA AAG GCA GAA ATA CTG GAG AGT GTC ATA AAA AAT TAT | 837 |
| GAA GAC CAC TTC CCT TTG TTG TTT AGT GAA GCC TCC GAG TGC | 879 |
| ATG CTG CTG GTC TTT GGC ATT GAT GTA AAG GAA GTG GAT CC | 920 |

(2) INFORMATION FOR SEQ ID NO: 23:

(i) SEQUENCE CHARACTERISTICS:
        (A) LENGTH: 1107 base pairs
        (B) TYPE: nucleic acid
        (C) STRANDEDNESS: single
        (D) TOPOLOGY: linear (ii) MOLECULE TYPE: genomic DNA (ix) FEATURE:
        (A) NAME/KEY: MAGE-11 gene (xi) SEQUENCE DESCRIPTION: SEQ ID NO: 23:

| | |
|---|---|
| AGAGAACAGG CCAACCTGGA GGACAGGAGT CCCAGGAGAA CCCAGAGGAT | 50 |
| CACTGGAGGA GAACAAGTGT AAGTAGGCCT TTGTTAGATT CTCCATGGTT | 100 |
| CATATCTCAT CTGAGTCTGT TCTCACGCTC CCTCTCTCCC CAGGCTGTGG | 150 |
| GGCCCCATCA CCCAGATATT TCCCACAGTT CGGCCTGCTG ACCTAACCAG | 200 |
| AGTCATCATG CCTCTTGAGC AAAGAAGTCA GCACTGCAAG CCTGAGGAAG | 250 |
| CCTTCAGGCC CAAGAAGAAG ACCTGGGCCT GGTGGGTGCA CAGGCTCTCC | 300 |
| AAGCTGAGGA GCAGGAGGCT GCCTTCTTCT CCTCTACTCT GAATGTGGGC | 350 |

```
ACTCTAGAGG AGTTGCCTGC TGCTGAGTCA CCAAGTCCTC CCCAGAGTCC          400

TCAGGAAGAG TCCTTCTCTC CCACTGCCAT GGATGCCATC TTTGGGAGCC          450

TATCTGATGA GGGCTCTGGC AGCCAAGAAA AGGAGGGGCC AAGTACCTCG          500

CCTGACCTGA TAGACCCTGA GTCCTTTTCC CAAGATATAC TACATGACAA          550

GATAATTGAT TTGGTTCATT TATTCTCCGC AAGTATCGAG TCAAGGGGCT          600

GATCACAAAG GCAGAA                                               616

ATG CTG GGG AGT GTC ATC AAA AAT TAT GAG GAC TAC TTT CCT         658

GAG ATA TTT AGG GAA GCC TCT GTA TGC ATG CAA CTG CTC TTT         700

GGC ATT GAT GTG AAG GAA GTG GAC CCC ACT AGC CAC TCC TAT         742

GTC CTT GTC ACC TCC CTC AAC CTC TCT TAT GAT GGC ATA CAG         784

TGT AAT GAG CAG AGC ATG CCC AAG TCT GGC CTC CTG ATA ATA         826

GTC CTG GGT GTA ATC TTC ATG GAG GGG AAC TGC ATC CCT GAA         868

GAG GTT ATG TGG GAA GTC CTG AGC ATT ATG GGG GTG TAT GCT         910

GGA AGG GAG CAC TTC CTC TTT GGG GAG CCC AAG AGG CTC CTT         952

ACC CAA AAT TGG GTG CAG GAA AAG TAC CTG GTG TAC CGG CAG         994

GTG CCC GGC ACT GAT CCT GCA TGC TAT GAG TTC CTG TGG GGT        1036

CCA AGG GCC CAC GCT GAG ACC AGC AAG ATG AAA GTT CTT GAG        1078

TAC ATA GCC AAT GCC AAT GGG AGG GAT CC                         1107

(2) INFORMATION FOR SEQ ID NO: 24:

(i) SEQUENCE CHARACTERISTICS:
        (A) LENGTH: 2150 base pairs
        (B) TYPE:   nucleic acid
        (C) STRANDEDNESS: single
        (D) TOPOLOGY: linear (ii) MOLECULE TYPE: genomic DNA (ix) FEATURE:
        (A) NAME/KEY: smage-I (xi) SEQUENCE DESCRIPTION: SEQ ID NO: 24:

TCTGTCTGCA TATGCCTCCA CTTGTGTGTA GCAGTCTCAA ATGGATCTCT           50

CTCTACAGAC CTCTGTCTGT GTCTGGCACC CTAAGTGGCT TTGCATGGGC          100

ACAGGTTTCT GCCCCTGCAT GGAGCTTAAA TAGATCTTTC TCCACAGGCC          150

TATACCCCTG CATTGTAAGT TTAAGTGGCT TTATGTGGAT ACAGGTCTCT          200

GCCCTTGTAT GCAGGCCTAA GTTTTTCTGT CTGCTTAACC CCTCCAAGTG          250

AAGCTAGTGA AAGATCTAAC CCACTTTTGG AAGTCTGAAA CTAGACTTTT          300

ATGCAGTGGC CTAACAAGTT TTAATTTCTT CCACAGGGTT TGCAGAAAAG          350

AGCTTGATCC ACGAGTTCAG AAGTCCTGGT ATGTTCCTAG AAAG               394

ATG TTC TCC TGG AAA GCT TCA AAA GCC AGG TCT CCA TTA AGT         436

CCA AGG TAT TCT CTA CCT GGT AGT ACA GAG GTA CTT ACA GGT         478

TGT CAT TCT TAT CCT TCC AGA TTC CTG TCT GCC AGC TCT TTT         520

ACT TCA GCC CTG AGC ACA GTC AAC ATG CCT AGG GGT CAA AAG         562

AGT AAG ACC CGC TCC CGT GCA AAA CGA CAG CAG TCA CGC AGG         604

GAG GTT CCA GTA GTT CAG CCC ACT GCA GAG GAA GCA GGG TCT         646
```

| | |
|---|---|
| TCT CCT GTT GAC CAG AGT GCT GGG TCC AGC TTC CCT GGT GGT | 688 |
| TCT GCT CCT CAG GGT GTG AAA ACC CCT GGA TCT TTT GGT GCA | 730 |
| GGT GTA TCC TGC ACA GGC TCT GGT ATA GGT GGT AGA AAT GCT | 772 |
| GCT GTC CTG CCT GAT ACA AAA AGT TCA GAT GGC ACC CAG GCA | 814 |
| GGG ACT TCC ATT CAG CAC ACA CTG AAA GAT CCT ATC ATG AGG | 856 |
| AAG GCT AGT GTG CTG ATA GAA TTC CTG CTA GAT AAA TTT AAG | 898 |
| ATG AAA GAA GCA GTT ACA AGG AGT GAA ATG CTG GCA GTA GTT | 940 |
| AAC AAG AAG TAT AAG GAG CAA TTC CCT GAG ATC CTC AGG AGA | 982 |
| ACT TCT GCA CGC CTA GAA TTA GTC TTT GGT CTT GAG TTG AAG | 1024 |
| GAA ATT GAT CCC AGC ACT CAT TCC TAT TTG CTG GTA GGC AAA | 1066 |
| CTG GGT CTT TCC ACT GAG GGA AGT TTG AGT AGT AAC TGG GGG | 1108 |
| TTG CCT AGG ACA GGT CTC CTA ATG TCT GTC CTA GGT GTG ATC | 1150 |
| TTC ATG AAG GGT AAC CGT GCC ACT GAG CAA GAG GTC TGG CAA | 1192 |
| TTT CTG CAT GGA GTG GGG GTA TAT GCT GGG AAG AAG CAC TTG | 1234 |
| ATC TTT GGC GAG CCT GAG GAG TTT ATA AGA GAT GTA GTG CGG | 1276 |
| GAA AAT TAC CTG GAG TAC CGC CAG GTA CCT GGC AGT GAT CCC | 1318 |
| CCA AGC TAT GAG TTC CTG TGG GGA CCC AGA GCC CAT GCT GAA | 1360 |
| ACA ACC AAG ATG AAA GTC CTG GAA GTT TTA GCT AAA GTC AAT | 1402 |
| GGC ACA GTC CCT AGT GCC TTC CCT AAT CTC TAC CAG TTG GCT | 1444 |
| CTT AGA GAT CAG GCA GGA GGG GTG CCA AGA AGG AGA GTT CAA | 1486 |
| GGC AAG GGT GTT CAT TCC AAG GCC CCA TCC CAA AAG TCC TCT | 1528 |
| AAC ATG TAG | 1537 |
| TTGAGTCTGT TCTGTTGTGT TTGAAAAACA GTCAGGCTCC TAATCAGTAG | 1587 |
| AGAGTTCATA GCCTACCAGA ACCAACATGC ATCCATTCTT GGCCTGTTAT | 1637 |
| ACATTAGTAG AATGGAGGCT ATTTTTGTTA CTTTTCAAAT GTTTGTTTAA | 1687 |
| CTAAACAGTG CTTTTTGCCA TGCTTCTTGT TAACTGCATA AAGAGGTAAC | 1737 |
| TGTCACTTGT CAGATTAGGA CTTGTTTTGT TATTTGCAAC AAACTGGAAA | 1787 |
| ACATTATTTT GTTTTTACTA AAACATTGTG TAACATTGCA TTGGAGAAGG | 1837 |
| GATTGTCATG GCAATGTGAT ATCATACAGT GGTGAAACAA CAGTGAAGTG | 1887 |
| GGAAAGTTTA TATTGTTAAT TTGAAAATT TTATGAGTGT GATTGCTGTA | 1937 |
| TACTTTTTTC TTTTTTGTAT AATGCTAAGT GAAATAAAGT TGGATTTGAT | 1987 |
| GACTTTACTC AAATTCATTA GAAAGTAAAT CGTAAAACTC TATTACTTTA | 2037 |
| TTATTTTCTT CAATTATGAA TTAAGCATTG GTTATCTGGA AGTTTCTCCA | 2087 |
| GTAGCACAGG ATCTAGTATG AAATGTATCT AGTATAGGCA CTGACAGTGA | 2137 |
| GTTATCAGAG TCT | 2150 |

(2) INFORMATION FOR SEQ ID NO: 25:

(i) SEQUENCE CHARACTERISTICS:
        (A) LENGTH: 2099 base pairs
        (B) TYPE: nucleic acid
        (C) STRANDEDNESS: single
        (D) TOPOLOGY: linear (ii) MOLECULE TYPE: genomic DNA (ix) FEATURE:
    (A) NAME/KEY: smage-II (xi) SEQUENCE DESCRIPTION: SEQ ID NO: 25:

| | | |
|---|---|---|
| ACCTTATTGG GTCTGTCTGC ATATGCCTCC ACTTGTGTGT AGCAGTCTCA | 50 |
| AATGGATCTC TCTCTACAGA CCTCTGTCTG TGTCTGGCAC CCTAAGTGGC | 100 |
| TTTGCATGGG CACAGGTTTC TGCCCCTGCA TGGAGCTTAA ATAGATCTTT | 150 |
| CTCCACAGGC CTATACCCCT GCATTGTAAG TTTAAGTGGC TTTATGTGGA | 200 |
| TACAGGTCTC TGCCCTTGTA TGCAGGCCTA AGTTTTTCTG TCTGCTTAGC | 250 |
| CCCTCCAAGT GAAGCTAGTG AAAGATCTAA CCCACTTTTG GAAGTCTGAA | 300 |
| ACTAGACTTT TATGCAGTGG CCTAACAAGT TTTAATTTCT TCCACAGGGT | 350 |
| TTGCAGAAAA GAGCTTGATC CACGAGTTCG GAAGTCCTGG TATGTTCCTA | 400 |
| GAAAGATGTT CTCCTGGAAA GCTTCAAAAG CCAGGTCTCC ATTAAGTCCA | 450 |
| AGGTATTCTC TACCTGGTAG TACAGAGGTA CTTACAGGTT GTCATTCTTA | 500 |
| TCTTTCCAGA TTCCTGTCTG CCAGCTCTTT TACTTCAGCC CTGAGCACAG | 550 |
| TCAACATGCC TAGGGGTCAA AAGAGTAAGA CCCGCTCCCG TGCAAAACGA | 600 |
| CAGCAGTCAC GCAGGGAGGT TCCAGTAGTT CAGCCCACTG CAGAGGAAGC | 650 |
| AGGGTCTTCT CCTGTTGACC AGAGTGCTGG GTCCAGCTTC CCTGGTGGTT | 700 |
| CTGCTCCTCA GGGTGTGAAA ACCCCTGGAT CTTTTGGTGC AGGTGTATCC | 750 |
| TGCACAGGCT CTGGTATAGG TGGTAGAAAT GCTGCTGTCC TGCCTGATAC | 800 |
| AAAAAGTTCA GATGGCACCC AGGCAGGGAC TTCCATTCAG CACACACTGA | 850 |
| AAGATCCTAT CATGAGGAAG GCTAGTGTGC TGATAGAATT CCTGCTAGAT | 900 |
| AAGTTTAAGA TGAAAGAAGC AGTTACAAGG AGTGAAATGC TGGCAGTAGT | 950 |
| TAACAAGAAG TATAAGGAGC AATTCCCTGA GATCCTCAGG AGAACTTCTG | 1000 |
| CACGCCTAGA ATTAGTCTTT GGTCTTGAGT TGAAGGAAAT TGATCCCAGC | 1050 |
| ACTCATTCCT ATTTGCTGGT AGGCAAACTG GGTCTTTCCA CTGAGGGAAG | 1100 |
| TTTGAGTAGT AACTGGGGGT TGCCTAGGAC AGGTCTCCTA ATGTCTGTCC | 1150 |
| TAGGTGTGAT CTTCATGAAG GGTAACCGTG CCACTGAGCA AGAGGTCTGG | 1200 |
| CAATTTCTGC ATGGAGTGGG GGTATATGCT GGGAAGAAGC ACTTGATCTT | 1250 |
| TGGCGAGCCT GAGGAGTTTA TAAGAGATGT AGTGCGGGAA AATTACCTGG | 1300 |
| AGTACCGCCA GGTACCTGGC AGTGATCCCC CAAGCTATGA GTTCCTGTGG | 1350 |
| GGACCCAGAG CCCATGCTGA AACAACCAAG ATGAAAGTCC TGGAAGTTTT | 1400 |
| AGCTAAAGTC AATGGCACAG TCCCTAGTGC CTTCCCTAAT CTCTACCAGT | 1450 |
| TGGCTCTTAG AGATCAGGCA GGAGGGGTGC CAAGAAGGAG AGTTCAAGGC | 1500 |
| AAGGGTGTTC ATTCCAAGGC CCCATCCCAA AAGTCCTCTA ACATGTAGTT | 1550 |
| GAGTCTGTTC TGTTGTGTTT GAAAAACAGT CAGGCTCCTA ATCAGTAGAG | 1600 |
| AGTTCATAGC CTACCAGAAC CAACATGCAT CCATTCTTGG CCTGTTATAC | 1650 |
| ATTAGTAGAA TGGAGGCTAT TTTTGTTACT TTTCAAATGT TTGTTTAACT | 1700 |
| AAACAGTGCT TTTTGCCATG CTTCTTGTTA ACTGCATAAA GAGGTAACTG | 1750 |
| TCACTTGTCA GATTAGGACT TGTTTTGTTA TTTGCAACAA ACTGGAAAAC | 1800 |
| ATTATTTTGT TTTTACTAAA ACATTGTGTA ACATTGCATT GGAGAAGGGA | 1850 |

-continued

```
TTGTCATGGC AATGTGATAT CATACAGTGG TGAAACAACA GTGAAGTGGG        1900

AAAGTTTATA TTGTTAGTTT TGAAAATTTT ATGAGTGTGA TTGCTGTATA        1950

CTTTTTTCTT TTTTGTATAA TGCTAAGTGA AATAAAGTTG GATTTGATGA        2000

CTTTACTCAA ATTCATTAGA AAGTAAATCA TAAAACTCTA TTACTTTATT        2050

ATTTTCTTCA ATTATTAATT AAGCATTGGT TATCTGGAAG TTTCTCCAG         2099

(2) INFORMATION FOR SEQ ID NO: 26:

(i) SEQUENCE CHARACTERISTICS:
        (A) LENGTH:  9 amino acids
        (B) TYPE:    amino acids
        (D) TOPOLOGY:   linear (ii) MOLECULE TYPE:  protein (xi) SEQUENCE DESCRIPTION:  SEQ ID NO: 26:

Glu Ala Asp Pro Thr Gly His Ser Tyr
```

TUMOR REJECTION ANTIGEN PRECURSORS, TUMOR REJECTION ANTIGENS AND USES THEREOF

This application is a continuation-in-part of Ser. No. 07/807,043, filed Dec. 12, 1991, now U.S. Pat. No. 5,342,774 which is a continuation-in-part of Ser. No. 07/764,365, filed Sep. 23, 1991 now abandoned, which is a continuation-in-part of Ser. No. 07/728,838, filed Jul. 9, 1991 now abandoned, which is a continuation-in-part of Ser. No. 07/705,702, filed May 23, 1991, and now abandoned.

FIELD OF THE INVENTION

This invention relates in general to the field of immunogenetics as applied to the study of oncology. More specifically, it relates to the study and analysis of mechanisms by which tumors are recognized by the organism's immune system such as through the presentation of so-called tumor rejection antigens, and the expression of what will be referred to herein as "tumor rejection antigen precursors".

BACKGROUND AND PRIOR ART

The study of the recognition or lack of recognition of cancer cells by a host organism has proceeded in many different directions. Understanding of the field presumes some understanding of both basic immunology and oncology.

Early research on mouse tumors revealed that these displayed molecules which led to rejection of tumor cells when transplanted into syngeneic animals. These molecules are "recognized" by T-cells in the recipient animal, and provoke a cytolytic T-cell response with lysis of the transplanted cells. This evidence was first obtained with tumors induced in vitro by chemical carcinogens, such as methylcholanthrene. The antigens expressed by the tumors and which elicited the T-cell response were found to be different for each tumor. See Prehn, et al., J. Natl. Canc. Inst. 18: 769–778 (1957); Klein et al., Cancer Res. 20: 1561–1572 (1960); Gross, Cancer Res. 3: 326–333 (1943), Basombrio, Cancer Res. 30: 2458–2462 (1970) for general teachings on inducing tumors with chemical carcinogens and differences in cell surface antigens. This class of antigens has come to be known as "tumor specific transplantation antigens" or "TSTAs". Following the observation of the presentation of such antigens when induced by chemical carcinogens, similar results were obtained when tumors were induced in vitro via ultraviolet radiation. see Kripke, J. Natl. Canc. Inst. 53: 333–1336 (1974).

While T-cell mediated immune responses were observed for the types of tumor described supra, spontaneous tumors were thought to be generally non-immunogenic. These were therefore believed not to present antigens which provoked a response to the tumor in the tumor carrying subject. See Hewitt, et al., Brit. J. Cancer 33: 241–259 (1976).

The family of tum$^-$ antigen presenting cell lines are immunogenic variants obtained by mutagenesis of mouse tumor cells or cell lines, as described by Boon et al., J. Exp. Med. 152: 1184–1193 (1980), the disclosure of which is incorporated by reference. To elaborate, tum$^-$ antigens are obtained by mutating tumor cells which do not generate an immune response in syngeneic mice and will form tumors (i.e., "tum$^+$" cells). When these tum$^+$ cells are mutagenized, they are rejected by syngeneic mice, and fail to form tumors (thus "tum$^-$"). See Boon et al., Proc. Natl. Acad. Sci. USA 74: 272 (1977), the disclosure of which is incorporated by reference. Many tumor types have been shown to exhibit this phenomenon. See, e.g., Frost et al., Cancer Res. 43: 125 (1983).

It appears that tum$^-$ variants fail to form progressive tumors because they elicit an immune rejection process. The evidence in favor of this hypothesis includes the ability of "tum$^-$" variants of tumors, i.e., those which do not normally form tumors, to do so in mice with immune systems suppressed by sublethal irradiation, Van Pel et al., Proc. Natl, Acad. Sci. USA 76: 5282–5285 (1979); and the observation that intraperitoneally injected tum$^-$ cells of mastocytoma P815 multiply exponentially for 12–15 days, and then are eliminated in only a few days in the midst of an influx of lymphocytes and macrophages (Uyttenhove et al., J. Exp. Med. 152: 1175–1183 (1980)). Further evidence includes the observation that mice acquire an immune memory which permits them to resist subsequent challenge to the same tum$^-$ variant, even when immunosuppressive amounts of radiation are administered with the following challenge of cells (Boon et al., Proc. Natl, Acad. Sci. USA 74: 272–275 (1977); Van Pel et al., supra; Uyttenhove et al., supra).

Later research found that when spontaneous tumors were subjected to mutagenesis, immunogenic variants were produced which did generate a response. Indeed, these variants were able to elicit an immune protective response against the original tumor. See Van Pel et al., J. Exp. Med. 157: 1992–2001 (1983). Thus, it has been shown that it is possible to elicit presentation of a so-called "tumor rejection antigen" in a tumor which is a target for a syngeneic rejection response. Similar results have been obtained when foreign genes have been transfected into spontaneous tumors. See Fearson et al., Cancer Res. 48: 2975–1980 (1988) in this regard.

A class of antigens has been recognized which are presented on the surface of tumor cells and are recognized by cytotoxic T cells, leading to lysis. This class of antigens will be referred to as "tumor rejection antigens" or "TRAs" hereafter. TRAs may or may not elicit antibody responses. The extent to which these antigens have been studied, has been via cytolytic T cell characterization studies, in vitro i.e., the study of the identification of the antigen by a particular cytolytic T cell ("CTL" hereafter) subset. The subset proliferates upon recognition of the presented tumor rejection antigen, and the cells presenting the antigen are lysed. Characterization studies have identified CTL clones which specifically lyse cells expressing the antigens. Examples of this work may be found in Levy et al., Adv. Cancer Res. 24: 1–59 (1977); Boon et al., J. Exp. Med. 152: 1184–1193 (1980); Brunner et al., J. Immunol. 124: 1627–1634 (1980); Maryanski et al., Eur. J. Immunol. 124: 1627–1634 (1980); Maryanski et al., Eur. J. Immunol. 12: 406–412 (1982); Palladino et al., Canc. Res. 47: 5074–5079 (1987). This type of analysis is required for other types of antigens recognized by CTLs, including minor histocompatibility antigens, the male specific H-Y antigens, and a class of antigens, referred to as "tum$^-$" antigens, and discussed herein.

A tumor exemplary of the subject matter described supra is known as P815. See DePlaen et al., Proc. Natl. Acad. Sci. USA 85: 2274–2278 (1988); Szikora et al., EKBO J 9: 1041–1050 (1990), and Sibille et al., J. Exp. Med. 172: 35–45 (1990), the disclosures of which are incorporated by reference. The P815 tumor is a mastocytoma, induced in a DBA/2 mouse with methyl-cholanthrene and cultured as both an in vitro tumor and a cell line. The P815 line has generated many tum$^-$ variants following mutagenesis, including variants referred to as P91A (DePlaen, surra), 35B (Szikora, supra), and P198 (Sibille, supra). In contrast to tumor rejection antigens —and this is a key distinction—the tum antigens are only present after the tumor cells are mutagenized. Tumor rejection antigens are present on cells of a given tumor without mutagenesis. Hence, with reference to the literature, a cell line can be tum+, such as the line referred to as "P1", and can be provoked to produce turn variants. Since the tum− phenotype differs from that of the parent cell line, one expects a difference in the DNA of tum− cell lines as compared to their tum+ parental lines, and this difference can be exploited to locate the gene of interest in tum− cells. As a result, it was found that genes of tum− variants such as P91A, 35B and P198 differ from their normal alleles by point mutations in the coding regions of the gene. See Szikora and Sibille, supra, and Lurguin et al., Cell 58: 293–303 (1989). This has proved not to be the case with the TRAs of this invention. These papers also demonstrated that peptides derived from the tum− antigen are presented by the $L^d$ molecule for recognition by CTLs. P91A is presented by $L^d$, P35 by $D^d$ and P198 by $K^d$.

It has now been found that the genes which code for the molecules which are processed to form the presentation tumor rejection antigens (referred to as "tumor rejection antigen precursors", "precursor molecules" or "TRAPs" hereafter), are not expressed in most normal adult tissues but are expressed in tumor cells. Genes which code for the TRAPs have now been isolated and cloned, and represent a portion of the invention disclosed herein.

The gene is useful as a source for the isolated and purified tumor rejection antigen precursor and the TRA themselves, either of which can be used as an agent for treating the cancer for which the antigen is a "marker", as well as in various diagnostic and surveillance approaches to oncology, discussed infra. It is known, for example, that tum− cells can be used to generate CTLs which lyse cells presenting different tum− antigens as well as tum+ cells. See, e.g., Maryanski et al., Eur. J. Immunol 12: 401 (1982); and Van den Eynde et al., Modern Trends in Leukemia IX (June 1990), the disclosures of which are incorporated by reference. The tumor rejection antigen precursor may be expressed in cells transfected by the gene, and then used to generate an immune response against a tumor of interest.

In the parallel case of human neoplasms, it has been observed that autologous mixed lymphocyte-tumor cell cultures ("MLTC" hereafter) frequently generate responder lymphocytes which lyse autologous tumor cells and do not lyse natural killer targets, autologous EBV-transformed B cells, or autologous fibroblasts (see Anichini et al., Immunol. Today 8: 385–389 (1987)). This response has been particularly well studied for melanomas, and MLTC have been carried out either with peripheral blood cells or with tumor infiltrating lymphocytes. Examples of the literature in this area including Knuth et al., Proc. Natl. Acad. sci. USA 86: 2804–2802 (1984); Mukherji et al., J. Exp. Med. 158: 240 (1983); Herin et all, Int. J. Canc. 39: 390–396 (1987); Topalian et al, J. Clin. Oncol 6: 839–853 (1988). Stable cytotoxic T cell clones ("CTLs" hereafter) have been derived from MLTC responder cells, and these clones are specific for the tumor cells. See Mukherji et al., supra, Herin et all, supra, Knuth et al., supra. The antigens recognized on tumor cells by these autologous CTLs do not appear to represent a cultural artifact, since they are found on fresh tumor cells. Topalian et al., supra; Degiovanni et al., Eur. J. Immunol. 20: 1865–1868 (1990). These observations, coupled with the techniques used herein to isolate the genes for specific murine tumor rejection antigen precursors, have led to the isolation of nucleic acid sequences coding for tumor rejection antigen precursors of TRAs presented on human tumors. It is now possible to isolate the nucleic acid sequences which code for tumor rejection antigen precursors, including, but not being limited to those most characteristic of a particular tumor, with ramifications that are described infra. These isolated nucleic acid sequences for human tumor rejection antigen precursors and applications thereof, as described infra, are also the subject of this invention.

These and various other aspects of the invention are elaborated upon in the disclosure which follows.

BRIEF DESCRIPTION OF THE FIGURES

FIG. 9 shows homology of sections of exon 3 from genes mage 1, 2 and 3.

FIGS. 11A and 11B present the data of FIG. 13 in table form.

BRIEF DESCRIPTION OF SEQUENCES

Figure 1A:
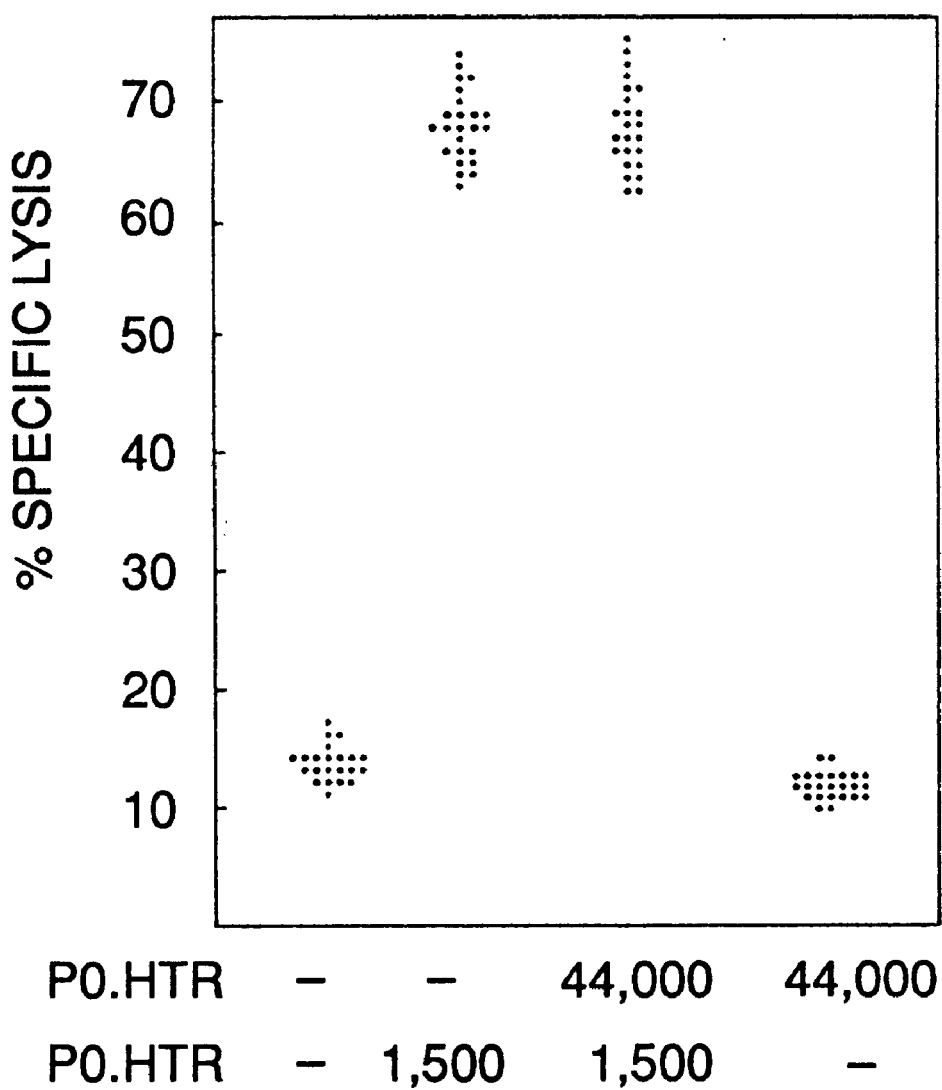
FIGS. 1A and 1B depict detection of transfectants expressing antigen P815A.

SEQ ID NO: 1 is CDNA for part of gene P1A.
SEQ ID NO: 2 presents coding region of cDNA for gene P1A.
SEQ ID NO: 3 shows non coding DNA for P1A CDNA which is 3' to the coding region of SEQ ID NO: 2.
SEQ ID NO: 4 is the entire sequence of cDNA for P1A.
SEQ ID NO: 5 is the genomic DNA sequence for P1A.
SEQ ID NO: 6 shows the amino acid sequence for the antigenic peptides for P1A TRA. The sequence is for cells which are A+ B+, i.e., express both the A and B antigens.
SEQ ID NO: 7 is a nucleic acid sequence coding for antigen E.
SEQ ID NO: 8 is a nucleic acid sequence coding for MAGE-1
SEQ ID NO: 9 is the gene for MAGE-2.
SEQ ID NO: 10 is the gene for MAGE-21.
SEQ ID NO: 11 is cDNA for MAGE-3.
SEQ ID NO: 12 is the gene for MAGE-31.
SEQ ID NO: 13 is the gene for MAGE-4.
SEQ ID NO: 14 is the gene for MAGE-41.
SEQ ID NO: 15 is CDNA for MAGE-4.
SEQ ID NO: 16 is cDNA for MAGE-5.
SEQ ID NO: 17 is genomic DNA for MAGE-51.
SEQ ID NO: 18 is CDNA for MAGE-6.
SEQ ID NO: 19 is genomic DNA for MAGE-7.

SEQ ID NO: 20 is genomic DNA for MAGE-8.
SEQ ID NO: 21 is genomic DNA for MAGE-9.
SEQ ID NO: 22 is genomic DNA for MAGE-10.
SEQ ID NO: 23 is genomic DNA for MAGE-11.
SEQ ID NO: 24 is genomic DNA for smage-I.
SEQ ID NO: 25 is genomic DNA for smage-II.

DETAILED DESCRIPTION OF PREFERRED EMBODIMENTS

Many different "MAGE" genes have been identified, as will be seen from the sequences which follow the application. The protocols described in the following examples were used to isolate these genes and CDNA sequences.

"MAGE" as used herein refers to a nucleic acid sequence isolated from human cells. The acronym "smage" is used to describe sequences of murine origin.

When "TRAP" or "TRAs" are discussed herein as being specific to a tumor type, this means that the molecule under consideration is associated with that type of tumor, although not necessarily to the exclusion of other tumor types.

EXAMPLE 1

In order to identify and isolate the gene coding for antigen P815A, gene transfection was used. This approach requires both a source of the gene, and a recipient cell line. Highly transfectable cell line P1.HTR was the starting material for the recipient, but it could not be used without further treatment, as it presents "antigen A", one of four recognized P815 tumor antigens. See Van Pel et al., Molecular Genetics 11: 467–475 (1985). Thus, screening experiments were carried out to isolate cell lines which did not express the antigen and which nonetheless possessed P1.HTR's desirable qualities.

To do this, P1.HTR was screened with CTLs which were specific for each of tumor antigens A, B, C and D. Such CTLs are described by Uyttenhove et al., J. Exp. Med. 157: 1040–1052 (1983).

To carry out the selection, $10^6$ cells of P1.HTR were mixed with $2–4 \times 10^6$ cells of the CTL clone in a round bottom tube in 2 ml of medium, and centrifuged for three minutes at 150×g. After four hours at 37° C., the cells were washed and resuspended in 10 ml of medium, following Maryanski et al., Eur. J. Immunol. 12: 406–412 (1982). Additional information on the CTL assay and screening protocol, in general may be found in Boon et al., J. Exp. Med. 152: 1184–1193 (1980), and Maryanski et al., Eur. J. Immunol. 12: 406–412 (1982), the disclosure of which are incorporated by reference.

When these selections were carried out, a cell line variant was found which expressed neither antigen A or B. Additional selections with CTLs specific for antigen C then yielded a variant which also lacked antigen C. Please see FIG. 2 for a summary of the results of these screenings. The variant P0.HTR is negative for antigens A, B and C, and was therefore chosen for the transfection experiments.

The cell line P0.HTR has been deposited in accordance with the Budapest Treaty at the Institute Pasteur Collection Nationale De Cultures De Microorganismes, 28, Rue de Docteur Roux, 75724 Paris France, and has accession number I-1117.

This methodology is adaptable to secure other cell lines which are variants of a cell type which normally presents at least one of the four recognized P815 tumor antigens, i.e., antigens A, B, C and D, where the variants present none of antigens A, B and C. P1.HTR is a mastocytoma cell line, so it will be seen that the protocol enables the isolation of biologically pure mastocytoma cell lines which express none of P815 antigens A, B and C, but which are highly transfectable. Other tumor types may also be screened in this fashion to secure desired, biologically pure cell lines. The resulting cell lines should be at least as transfectable with foreign DNA as is P1.HTR, and should be selected so as to not express a specific antigen.

EXAMPLE 2

Previous work reported by DePlaen et al., Proc. Natl. Acad. Sci. USA 85: 2274–2278 (1988) the disclosure of which is incorporated by reference herein had shown the efficacy of using cosmid library transfection to recover genes coding for tum⁻ antigens.

Selective plasmid and genomic DNA of P1.HTR were prepared, following Wölfel et al., Immunogenetics 26: 178–187 (1987). The transfection procedure followed Corsaro et al., Somatic Cell Molec. Genet 7: 603–616 (1981), with some modification. Briefly, 60 µg of cellular DNA and 3 µg of DNA of plasmid pHMR272, described by Bernard et al., Exp. Cell. Biol. 158: 237–243 (1985) were mixed. This plassid confers hygromycin resistance upon recipient cells, and therefore provides a convenient way to screen for transfectants. The mixed DNA was combined with 940 ul of 1 EM Tris-HCl (pH 7.5), 0.1 mM EDTA; and 310 ul 1M $CaCl_2$. The solution was added slowly, and under constant agitation to 1.25 ml of 50 MM Hepes, 280 mM NaCl, 1.5 mM $Na_2HPO_4$, adjusted to pH 7.1 with NaOH. Calcium phosphate—DNA precipitates were allowed to form for 30–45 minutes at room temperature. Following this, fifteen groups of P0.HTR cells ($5 \times 10^6$) per group were centrifuged for 10 minutes at 400 g. Supernatants were removed, and pellets were resuspended directly into the medium containing the DNA precipitates. This mixture was incubated for 20 minutes at 37° C., after which it was added to an 80 $cm^2$ tissue culture flask containing 22.5 ml DMEM, supplemented with 10% fetal calf serum. After 24 hours, medium was replaced. Forty-eight hours after transfection, cells were collected and counted. Transfected cells were selected in mass culture using culture medium supplemented with hygromycin B (350 ug/ml). This treatment selected cells for hygromycin resistance.

For each group, two flasks were prepared, each containing $8 \times 10^6$ cells in 40 ml of medium. In order to estimate the number of transfectants, $1 \times 10^6$ cells from each group were plated in 5 ml DMEM with 10% fetal calf serum (FCS), 0.4% bactoagar, and 300 ug/ml hygromycin B. The colonies were then counted 12 days later. Two independent determinations were carried out and the average taken. This was multiplied by 5 to estimate the number of transfectants in the corresponding group. Correction had to be made for the cloning efficiency of P815 cells, known to be about 0.3.

EXAMPLE 3

Eight days after transfection as described in example 2, supra, antibiotic resistant transfectants were separated from dead cells, using density centrifugation with Ficoll-Paque. These cells were maintained in non-selective medium for 1 or 2 days. The cells were plated in 96 well microplates (round bottom), at 30 cells/microwell in 200 ul of culture medium. Anywhere from 100–400 microwells were prepared, depending on the number of transfectants prepared. Agar colony tests gave estimates of 500–3000. After 5 days, the wells contained about $6 \times 10^4$ cells and replicate plates were prepared by transferring ⅒ of the wells to microplates which were then incubated at 30° C. One day later, master plates were centrifuged, medium removed, and 750 CTLs against P815 antigen A (CTL-P1:5) were added to each well together with $10^6$ irradiated syngeneic feeder spleen cells in CTL culture medium containing 40 U/ml recombinant human IL-2, and HAT medium to kill stimulator cells. Six days later, plates were examined visually to identify wells where CTLs had proliferated. Where plates showed proliferating microcultures, aliquots of 100 ul of the wells were transferred to another plate containing $^{51}$Cr labeled P1.HTR target cells ($2\times10^3$–$4\times10^3$ per well), and chromium release was measured after 4 hours. Replicate microcultures corresponding to those showing high CTL activity were expanded and cloned by limited dilution in DMEM with 10% FCS. Five days later, about 200 clones were collected and screened with the CTL.P1:5 cell line, described supra, in a visual lysis assay. See FIG. 1A for these results.

Figure 1B:
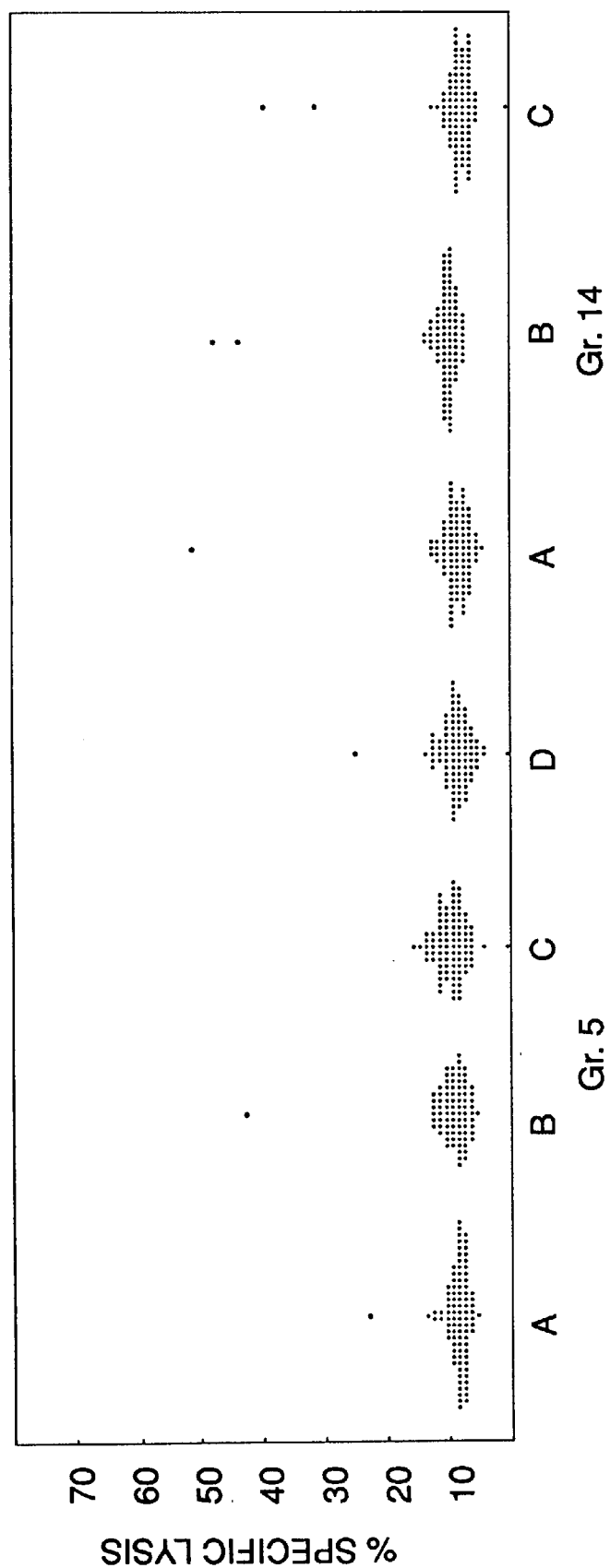

In these experiments, three of the fifteen groups of transfectants yielded a few positive microcultures. These microcultures were tested for lytic activity against P1.HTR, as described supra. Most of the microcultures where proliferation was observed showed lytic activity. This activity was well above background, as shown in FIG. 1B. This figure summarizes data wherein two groups of cells (groups "5" and "14"), 400 and 300 microwells were seeded with 30 hygromycin resistant transfected cells. Amplification and duplication of the microcultures was followed by addition of anti-A CTL P1:5. Six days later, lytic activity against P1.HTR was tested. In the figure, each point represents lytic activity of a single microculture.

Duplicate microcultures corresponding to several positive wells were subcloned, and more than 1% of the subclones were found to be lysed by anti-A CTL. Thus, three independent transfectants expressing P815A were obtained from 33,000 hygromycin resistant transfectants. One of these lines, referred to hereafter as P1A.T2 was tested further.

Figure 2:
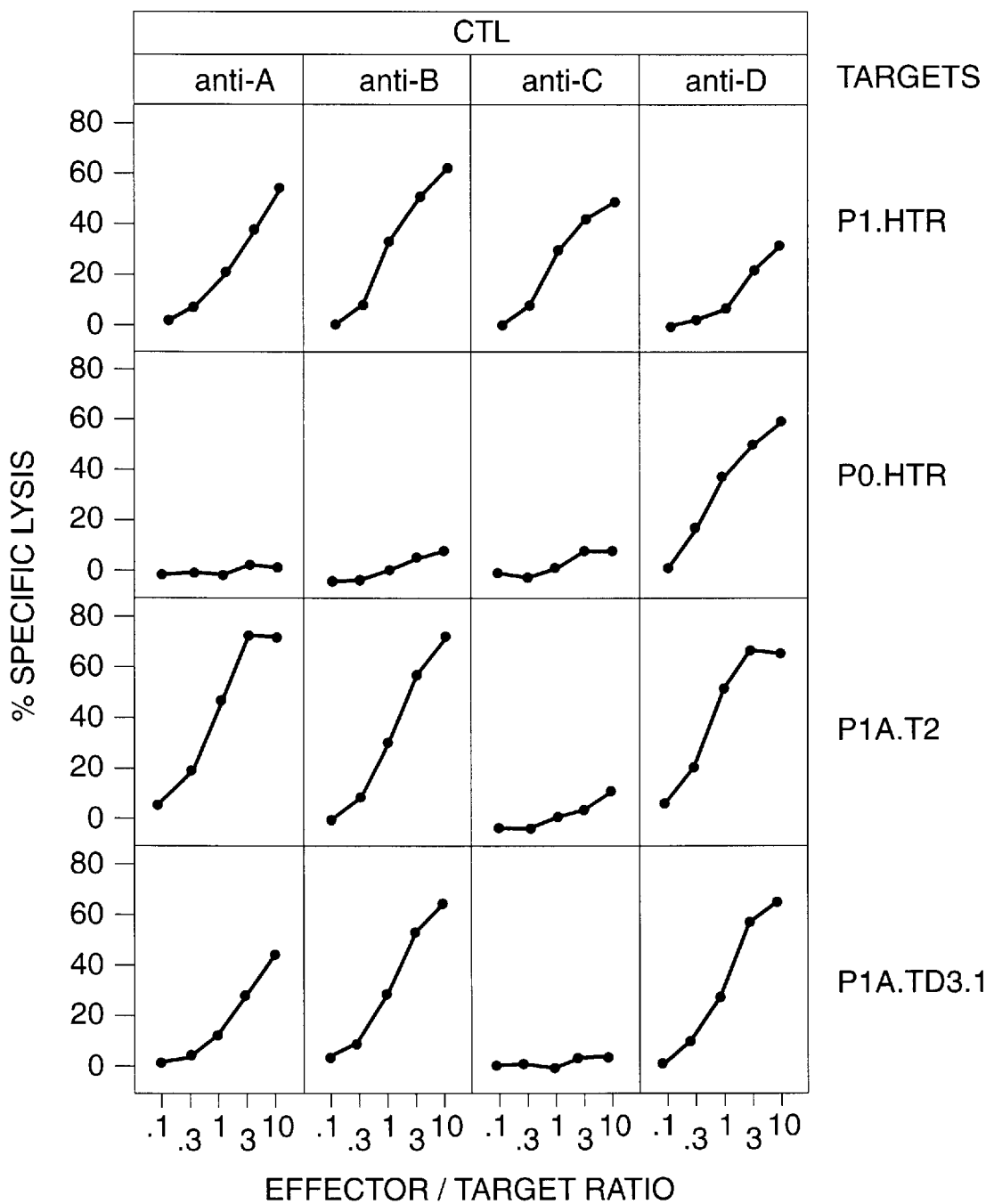
FIG. 2 shows the sensitivity of clones P1. HTR, PO.HTR, genomic transfectant P1A.T2 and cosmid transfectant P1A.TC3.1 to lysis by various CTLS, as determined by chromium release assays.

The relevant antigen profile of P1A.T2 is shown in FIG. 2, this being obtained via anti-CTL assays of the type described supra.

EXAMPLE 4

The CTL assays carried out for P1A.T2 demonstrated that it presented antigen A ("P815A"), and therefore had received the gene from P1.HTR. To that end, this cell line was used as a source for the gene for the antigen precursor in the following experiments.

Prior work had shown that genes coding for tum⁻ antigens could be recovered directly from transfectants obtained with a cosmid library. See DePlaen et al., Proc. Natl. Acad. Sci. USA 85: 2274–2278 (1988). This procedure was followed for recovery of the P815 gene.

Total genomic DNA of P1A.T2 was partially digested with restriction endonuclease Sau 3A1, and fractionated by NaCl density gradient ultracentrifugation to enrich for 35–50 kb DNA fragments, following Grosveld et al., Gene 10: 6715–6732 (1982). These fragments were ligated to cosmid arms of C2RB, described by Bates et al., Gene 26: 137–146 (1983), the disclosure of which is incorporated by reference. These cosmid arms had been obtained by cleavage with SmaI and treatment with calf intestinal phosphatase, followed by digestion with BamHI. Ligated DNA was packaged into lambda phage components, and titrated on *E. coli* ED 8767, following Grosveld et al., supra. Approximately $9\times10^5$ ampicillin resistant colonies were obtained per microgram of DNA insert.

The cosmid groups were amplified by mixing 30,000 independent cosmids with 2 ml of ED 8767 in 10 mM MgCl$_2$, incubated 20 minutes at 37° C., diluted with 20 ml of Luria Bertani ("LB") medium, followed by incubation for one hour. This suspension was titrated and used to inoculate 1 liter of LB medium in the presence of ampicillin (50 ug/ml). At a bacterial concentration of $2\times10^8$ cells/ml (OD$_{600}$=0.8), a 10 ml aliquot was frozen, and 200 ug/ml chloramphenicol was added to the culture for overnight incubation. Total cosmid DNA was isolated by alkaline lysis procedure, and purified on CsCl gradient.

In these experiments, a library of 650,000 cosmids was prepared. The amplification protocol involved the use of 21 groups of approximately 30,000 cosmids.

EXAMPLE 5

Using the twenty-one groups of cosmids alluded to supra, (60 ug) and 4 ug of pHMR272, described supra, groups of $5\times10^6$ P0.HTR cells were used as transfectant hosts. Transfection was carried out in the same manner as described in the preceding experiments. An average of 3000 transfectants per group were tested for antigen presentation, again using CTL assays as described. One group of cosmids repeatedly yielded positive transfectants, at a frequency of about 1/5,000 drug resistant transfectants. The transfectants, as with P1A.T2, also showed expression of both antigen A and B. The pattern of expression of transfectant P1A.TC3.1 is shown in FIG. 2.

EXAMPLE 6

As indicated in Example 5, supra, three independent cosmid transfected cells presenting P815A antigen were isolated. The DNA of these transfectants was isolated and packaged directly with lambda phage extracts, following DePlaen et al., Proc. Natl. Acad. Sci. USA 85: 2274–2278 (1988). The resulting product was titrated on *E. coli* ED 8767 with ampicillin selection, as in Example 5. Similarly, amplification of the cosmids and transfection followed Example 5, again using P0.HTR.

High frequencies of transfection were observed, as described in Table 1, which follows:

TABLE 1

Transfer of the expression of antigen P815A by cosmids obtained by direct packaging

| Transfectant obtained with the cosmid library | No. of cosmids obtained by direct packaging of 0.5 µg of DNA | No. of transfectants expressing P815A/no. of HmB[1] transfectants |
|---|---|---|
| TC3.1 | 32 | 87/192 |
| TC3.2 | 32000 | 49/384 |
| TC3.3 | 44 | 25/77 |

The cosmids were analyzed with restriction enzymes and it was found that directly packaged transfectant P1A.TC3.1 contained 32 cosmids, 7 of which were different. Each of these 7 cosmids was transfected into P0.HTR, in the manner described supra, and again, following the protocols described above, transfectants were studied for presentation of P815A. Four of the cosmid transfectants showed P815A presentation and, as with all experiments described herein, P815B was co-expressed.

Of the four cosmids showing presentation of the two antigens, cosmid C1A.3.1 was only 16.7 kilobases long, and was selected for further analysis as described infra.

Figure 3:
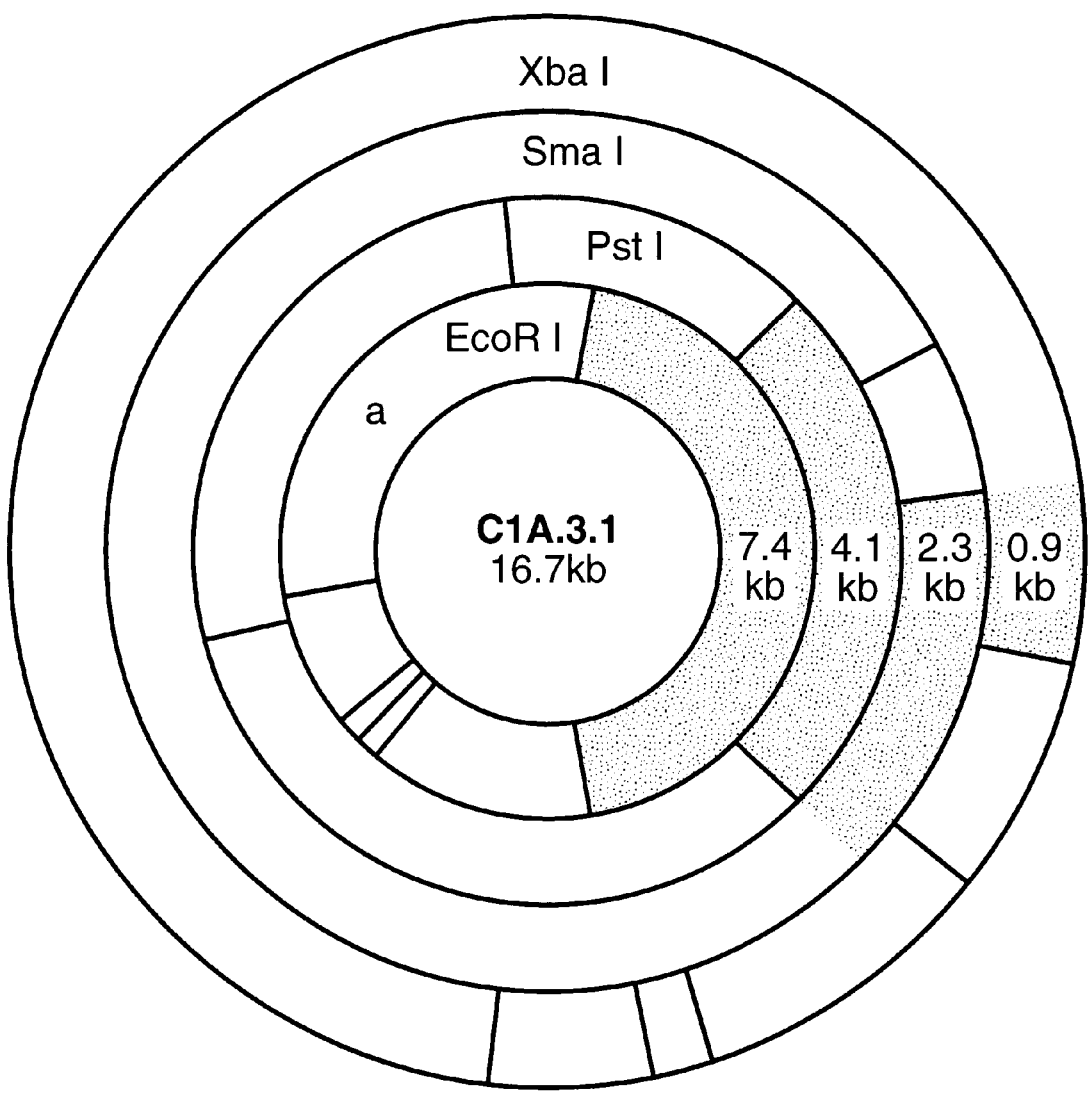
FIG. 3 is a restriction map of cosmid C1A.3.1.

The cosmid C1A.3.1 was subjected to restriction endonuclease analysis, yielding the map shown in FIG. 3.

All EcoRI fragments were transfected, again using the above described protocols, and only the 7.4 kilobase fragment produced a transfectant that anti-A CTLs could lyse. Similar experiments were carried out on the PstI fragments, and only a 4.1 kb fragment fully contained within the 7.4 kb EcoRI fragment produced lysable transfectants.

This fragment (i.e., the 4.1 kb PstI fragment), was digested with SmaI, giving a 2.3 kb fragment which also yielded host cells presenting antigens A and B after transfection. Finally, a fragment 900 bases long, secured with SmaI/XbaI, also transferred expression of the precursors of these two antigens, i.e., the transfected host cell presented both antigen A and antigen B.

EXAMPLE 7

The 900 base fragment described above was used as a probe to detect the expression of the P815A gene in parent cell line P1.HTR. To accomplish this, total cellular RNA was first isolated using the guanidine-isothiocyanate procedure of Davis et al., *Basic Methods In Molecular Biolocy* (Elseview Science Publishing Co, New York) (1986). The same reference was the source of the method used to isolate and purify polyA$^+$ MRNA using oligodT cellulose column chromatography.

Samples were then subjected to Northern Blot analysis. RNA samples were fractionated on 1% agarose gels containing 0.66M formaldehyde. The gels were treated with 10×SSC (SSC: 0.15M NaCl; 0.015M sodium citrate, pH 7.0) for 30 minutes before overnight blotting on nitrocellulose membranes. These were baked for two hours at 80° C., after which the membranes were prehybridized for 15 minutes at 60° C. in a solution containing 10% dextran sulfate, 1% SDS and 1M NaCl. Hybridization was then carried out using denatured probe (the 900 base fragment), together with 100 ug/ml salmon sperm DNA.

Figure 4:
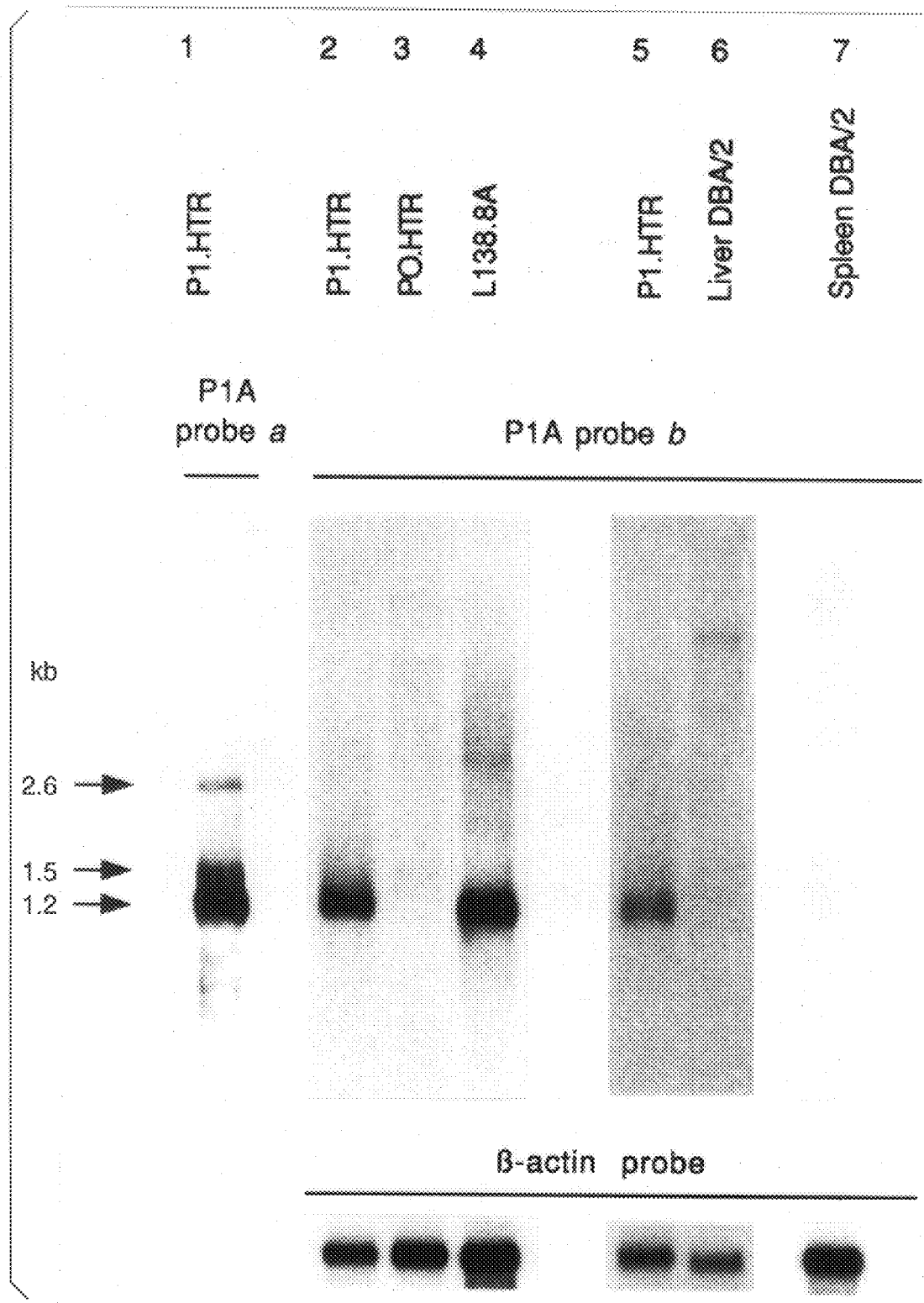
FIG. 4 shows Northern Blot analysis of expression of gene P1A.

When this protocol was carried out using P1.HTR poly A$^+$ RNA, a band of 1.2 kb and two fainter bands were identified, as shown in FIG. 4, lane 1 (6 ug of the RNA).

The same probe was used to screen a cDNA library, prepared from poly-A$^+$ RNA from the cell line. This yielded a clone with a 1kb insert, suggesting a missing 5' end. The Northern blots for the CDNA are not shown.

Hybridization experiments in each case were carried out overnight at 60° C. The blots were washed twice at room temperature with 2×SSC and twice at 60° C. with 2×SSC supplemented with 1% SDS.

The foregoing experiments delineated the DNA expressing the P815A antigen precursor sufficiently to allow sequencing, using the well known Sanger dideoxy chain termination method. This was carried out on clones generated using a variety of restriction endonucleases and by specific priming with synthetic oligonucleotide primers. The results for exons of the gene are set forth in sequence id no: 4.

EXAMPLE 8

The Northern analysis described supra suggested that the 5' end of the cDNA was missing. To obtain this sequence, cDNA was prepared from P1.HTR RNA using a primer corresponding to positions 320–303. The sequence was then amplified using the polymerase chain reaction using a 3' primer corresponding to positions 286–266 and a 5' primer described by Frohman et al., Proc. Natl. Acad. Sci. USA 85: 8998–9002 (1988). A band of the expected size (270 bases) was found, which hybridized to the 900 bp SmaI/XbaI fragment described supra on a Southern blot. Following cloning into m13tg 130 λ tg 131, the small, 270 bp fragment was sequenced. The sequence is shown in sequence id no: 1.

EXAMPLE 9

Following the procurement of the sequences described in Examples 7 and 8 and depicted in seq id no: 4, a 5.7 kb region of cosmid C1A.3.1 was sequenced. This fragment was known to contain the 900 base fragment which expressed P815A in transfectants. This experiment permitted delineation of introns and exons, since the cosmid is genomic in origin.

Figure 5:
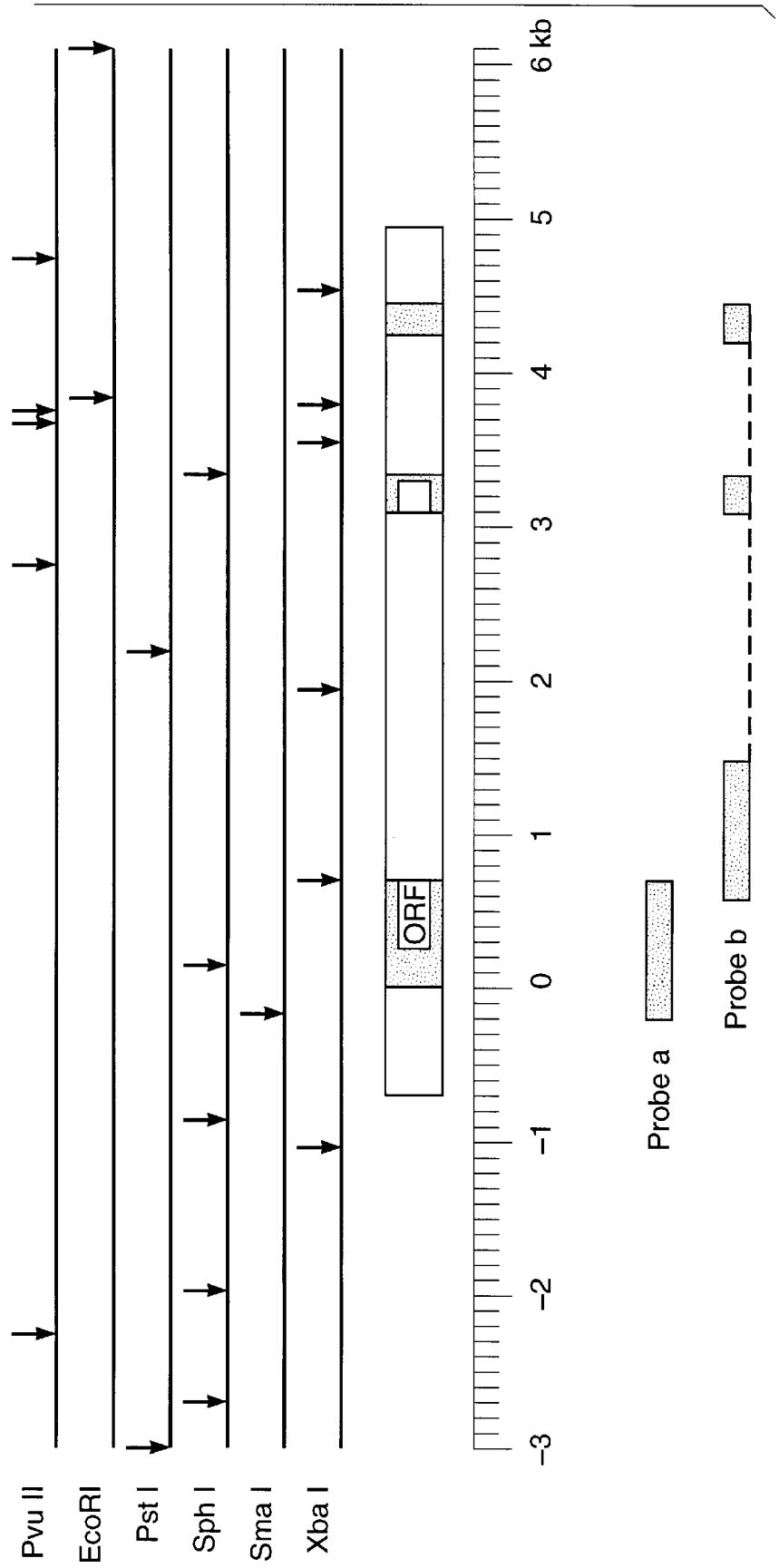
FIG. 5 sets forth the structure of gene P1A with its restriction sites.
Figure 6:
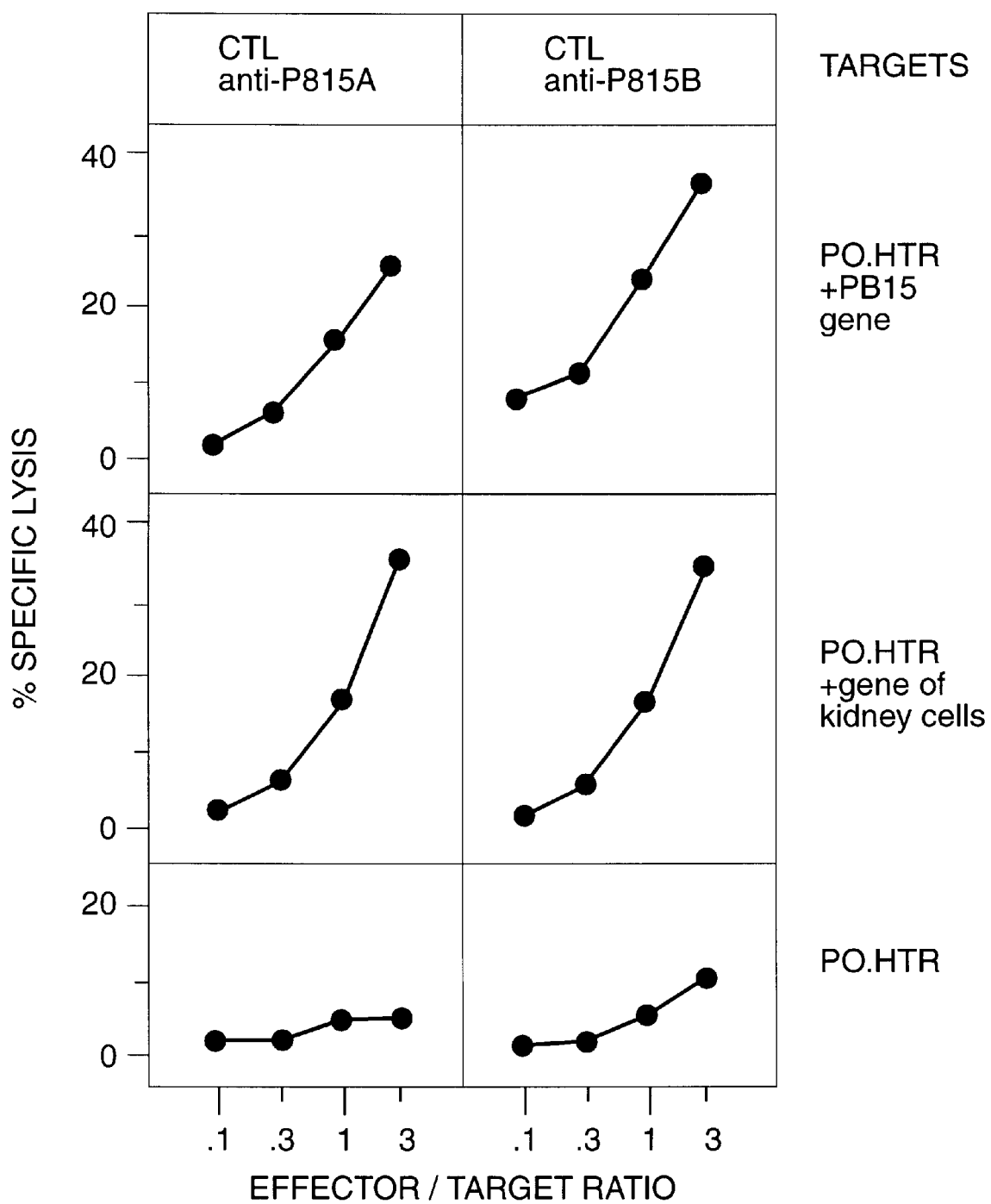
FIG. 6 shows the results obtained when cells were transfected with the gene from P1A, either isolated from P815 or normal cells and then tested with CTL lysis.

The delineated structure of the gene is shown in FIG. 5. Together with seq id no: 4, these data show that the gene for the antigen precursor, referred to as "P1A" hereafter, is approximately 5 kilobases long and contains 3 exons. An ORF for a protein of 224 amino acids starts in exon 1, ending in exon 2. The 900 base pair fragment which transfers expression of precursors for antigens A and B only contains exon 1. The promoter region contains a CAAT box, as indicated in seq. id no: 1, and an enhancer sequence. This latter feature has been observed in promoters of most MHC class I genes, as observed by Geraghty et al., J. Exp. Med 171: 1–18 (1990); Kimura et al., Cell 44: 261–272 (1986).

A computer homology search was carried out, using program FASTA with K-triple parameters of 3 and 6, as suggested by Lipman et al., Science 227: 1435–1441 (1985), and using Genbank database release 65 (October 1990). No homology was found except for a stretch of 95 bases corresponding to part of an acid region coded by exon 1 (positions 524–618), which is similar to sequences coding for acidic regions in mouse nucleolar protein NO38/B23, as described by Bourbon et al., Mol. Biol. 200: 627–638 (1988), and Schmidt-Zachmann et al., Chromosoma 96: 417–426 (1988). Fifty six of 95 bases were identical. In order to test whether these homologies were the reason for cross hybridizing, experiments were carried out using a mouse spleen CDNA library screened with the 900 base fragment. cDNA clones corresponding closely to the sizes of the cross hybridizing bands were obtained. These were partially sequenced, and the 2.6 kb cDNA was found to correspond exactly to reported CDNA sequence of mouse nucleolin, while the 1.5 kb cDNA corresponded to mouse nucleolar protein NO38/B23.

Analysis of the nucleotide sequence of the gene, referred to as "P1A" hereafter, suggests that its coded product has a molecular mass of 25 kd. Analysis of the sequence id no: 4 shows a potential nuclear targeting signal at residues 5–9 (Dingwall et al., Ann. Rev. Cell Biol. 2: 367–390 (1986)), as well as a large acidic domain at positions 83–118. As indicated surra, this contains the region of homology between P1A and the two nucleolar proteins. A putative phosphorylation site can be found at position 125 (serine). Also, a second acidic domain is found close to the C-terminus as an uninterrupted stretch of 14 glutamate residues. A similar C-terminal structure has been found by Kessel et al. Proc. Natl. Acad. Sci. USA 84: 5306–5310 (1987), in a murine homeodomain protein having nuclear localization.

In studies comparing the sequence of gene P1A to the sequences for P91A, 35B and P198, no similarities were found, showing that P1A is indicative of a different class of genes and antigens.

EXAMPLE 10

With the P1A probe and sequence in hand, investigations were carried out to determine whether the gene present in normal tissue was identical to that expressed by the tumor. To do this, phage libraries were prepared, using lambda zapII 10 and genomic DNA of DBA2 murine kidney cells. P1A was used as a probe. Hybridization conditions were as described supra, and a hybridizing clone was found. The clone contained exons one and two of the P1A gene, and corresponded to positions 0.7 to 3.8 of FIG. 5. Following localization of this sequence, PCR amplification was carried out to obtain the sequence corresponding to 3.8 to 4.5 of FIG. 5.

Sequence analysis was carried out, and no differences were found between the gene from normal kidneys and the P1A gene as obtained from the P815 tumor cells.

Figure 7:
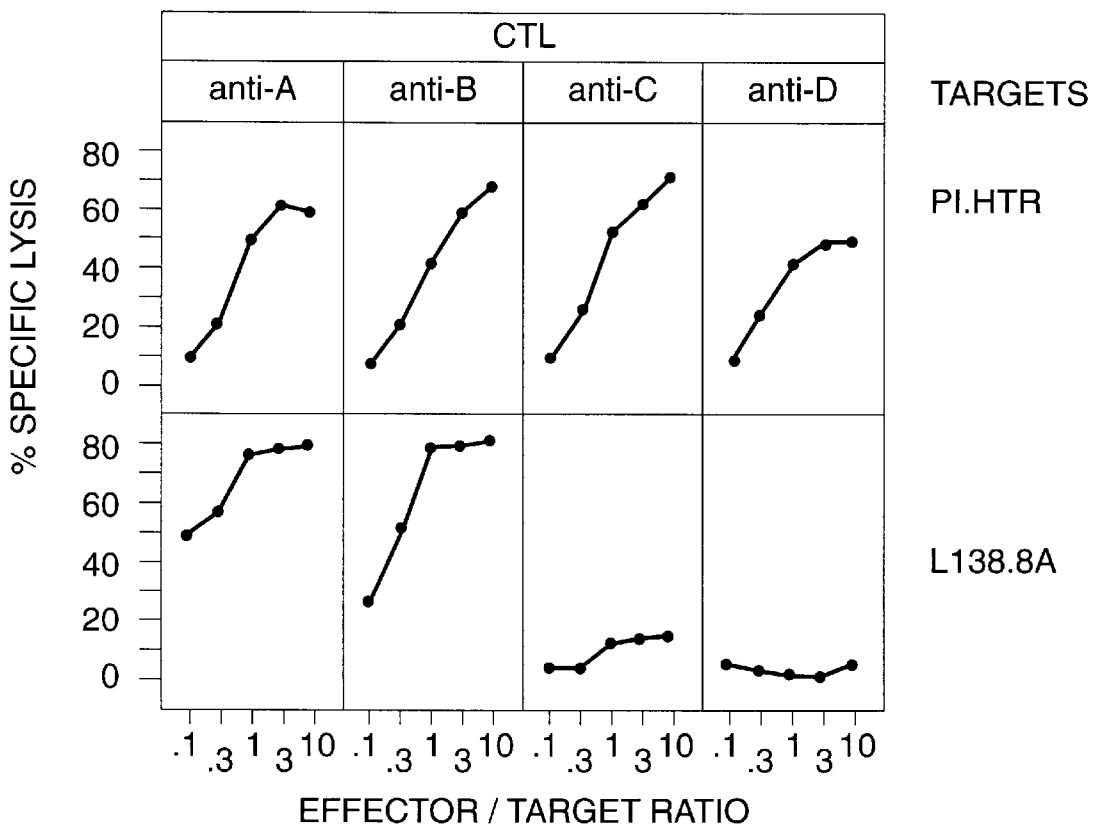
FIG. 7 shows lytic studies using mast cell line L138. 8A.

In further experiments, the gene as found in DBA/2 kidney cells was transfected into P0.HTR, as described supra. These experiments, presented pictorially in FIG. 7, showed that antigens A and B were expressed as efficiently by the kidney gene isolated from normal kidney cells as with the P1A gene isolated from normal kidney cells.

These experiments lead to the conclusion that the gene coding for the tumor rejection antigen precursor is a gene that does not result from a mutation; rather, it would appear that the gene is the same as one present in normal cells, but is not expressed therein. The ramifications of this finding are important, and are discussed infra.

In studies not elaborated upon herein, it was found that variants of the gene were available. Some cells were "P1A⁻ B⁺", rather than the normal "P1A". The only difference between these is a point mutation in exon 1, with the 18th triplet coding for Ala in the variant instead of Val.

EXAMPLE 11

Additional experiments were carried out with other cell types. Following the protocols described for Northern blot hybridizations supra, RNA of normal liver and spleen cells was tested to determine if a transcript of the P1A gene could be found. The Northern blot data are presented in FIG. 4 and, as can be seen, there is no evidence of expression.

The murine P815 cell line from which P1A was isolated is a mastocytoma. Therefore, mast cell lines were studied to determine if they expressed the gene. Mast cell line MC/9, described by Nabel et al., Cell 23: 19–28 (1981), and short term cultures of bone marrow derived mast cells were tested in the manner described supra (Northern blotting), but no transcript was found. In contrast when a Balb/C derived IL-3 dependent cell line L138.8A (Hültner et al., J. Immunol. 142: 3440–3446 (1989)) was tested, a strong signal was found. The mast cell work is shown in FIG. 4.

Figure 8:
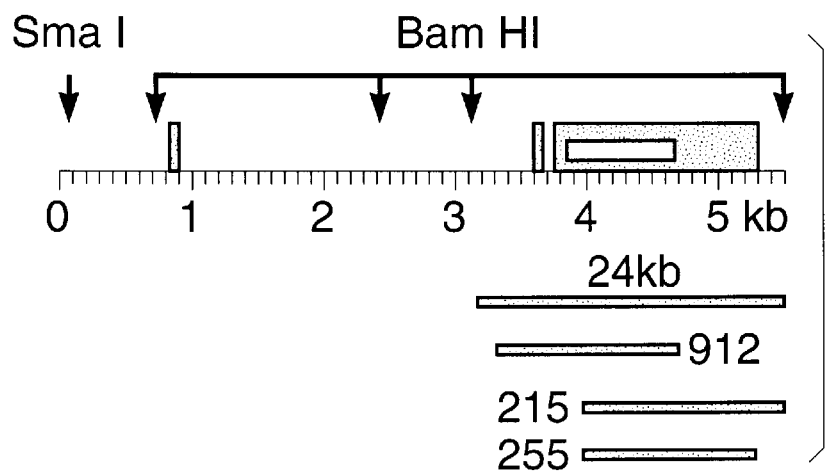
FIG. 8 is a map of subfragments of the 2.4 kb antigen E fragment sequence which also express the antigen.

It is known that both BALB/C and DBA/2 mice share H-$2^d$ haplotype, and thus it was possible to test sensitivity to lysis using the CTLs described supra. FIG. 8 shows these results, which essentially prove that anti-A and anti-B CTLs lysed the cells strongly, whereas anti-C and anti-D lines did not.

Further tests were carried out on other murine tumor cell lines, i.e., teratocarcinoma cell line PCC4 (Boon et al., Proc. Natl. Acad. Sci. USA 74: 272–275 (1977), and leukemias LEC and WEH1-3B. Expression could not be detected in any of these samples.

EXAMPLE 12

The actual presentation of the P1A antigen by MHC molecules was of interest. To test this, cosmid C1A.3.1 was transfected into fibroblast cell line DAP, which shows phenotype H-$2^k$. The cell lines were transfected with genes expressing one of the $K^d$, $D^d$, and $L^d$ antigen. Following transfection with both the cosmid and the MHC gene, lysis with CTLs was studied, again as described supra. These studies, summarized in Table 2, show that $L^d$ is required for presentation of the P1A antigens A and B.

TABLE 2

H-2 restriction of antigens P815A and P815B

| Recipient cell* | No. of clones lysed by the CTL/no. of HMB[1] clones** | |
|---|---|---|
| | CTL anti-A | CTL anti-B |
| DAP (H-$2^k$) | 0/208 | 0/194 |
| DAP + $K^d$ | 0/165 | 0/162 |
| DAP + $D^d$ | 0/157 | 0/129 |
| DAP + $L^d$ | 25/33 | 15/20 |

*Cosmid C1A.3.1 containing the entire P1A gene was tranfected in DAP cells previously transfected with H-$2^d$ class 1 genes as indicated.
**Independent drug-resistant colonies were tested for lysis by anti-A or anti-B CTL is a visual assay.

The observation that one may associate presentation of a tumor rejection antigen with a particular MHC molecule was confirmed in experiments with human cells and HLA molecules, as elaborated upon infra.

EXAMPLE 13

Using the sequence of the P1A gene as well as the amino acid sequence derivable therefrom, antigenic peptides which were A⁺B⁺ (i.e., characteristic of cells which express both the A and B antigens), and those which are A⁻ B⁺ were identified. The peptide is presented in FIG. 10. This peptide when administered to samples of P0.HTR cells in the presence of CTL cell lines specific to cells presenting it, led to lysis of the P0.HTR cells, lending support to the view that peptides based on the product expressed by the gene can be used as vaccines.

EXAMPLE 14

The human melanoma cell line referred to hereafter as MZ2-MEL is not a clonal cell line. It expresses four stable antigens recognized by autologous CTLs, known as antigens "D, E, F, and A". In addition, two other antigens "B" and "C" are expressed by some sublines of the tumor. CTL clones specific for these six antigens are described by Van den Eynde et al., Int. J. Canc. 44: 634–640 (1989). Among the recognized subclones of MZ2-MEL are MEL.43, MEL3.0 and MEL3.1. (Van den Eynde et al., supra). Cell line MEL3.1 expresses antigen E, as determined by CTL studies as described for P815 variants, supra, so it was chosen as a source for the nucleic acid sequence expressing the antigen precursor.

In isolating the pertinent nucleic acid sequence for 20 a tumor rejection antigen precursor, the techniques developed supra, showed that a recipient cell is needed which fulfills two criteria: (i) the recipient cell must not express the TRAP of interest under normal conditions, and (ii) it must express the relevant class I HLA molecule. Also, the recipient cell must have a high transfection frequency, i.e., it must be a "good" recipient.

In order to secure such a cell line, the clonal subline ME3.1 was subjected to repeated selection with anti-E CTL 82/30 as described by Van den Eynde, supra. The repeated cycles of selection led to isolation of subclone MZ2-MEL-2.2 isc E⁻. This subclone is also HPRT⁻, (i.e., sensitive to HAT medium: $10^{-4}$M hypoxanthine, $3.8 \times 10^{-7}$ aminopterine, $1.6 \times 10^{-5}$M 2-deoxythymidine). The subclone is referred to as "MEL-2.2" for simplicity hereafter.

EXAMPLE 15

The genomic DNA of MEL3.0 was prepared following Wölfel et al., Immunogenetics 26: 178–187 (1987), the disclosure of which is incorporated by reference. The plasmid pSVtkneoβ, as described by Nicolas et al., Cold Spring Harb., Conf. Cell Prolif. 10: 469–485 (1983) confers geneticin resistance, so it can be used as a marker for cotransfection, as it was in this experiment.

Following a procedure similar but not identical to that of Corsao et al., Somatic Cell Molec. Genet 7: 603–616 (1981), total genomic DNA and the plasmid were cotransfected. The genomic DNA (60 μg) and plasmid DNA (6 μg) were mixed in 940 μl of 1 uM Tris-HCl (pH 7.5), 0.1 mM EDTA, after which 310 μl of 1M $CaCl_2$ was added. This solution was slowly added, under constant agitation, to 1.25 ml of 2×HBS (50 zM HEPES, 280 mM NaCl 1.5 mM $Na_2HPO_4$, adjusted to pH 7.1 with NaOH). The calcium phosphate DNA precipitates were allowed to form for 30–45 minutes at room temperature, after which they were applied to 80 $cm^2$ tissue culture flasks which had been seeded 24 hours previously with $3 \times 10^6$ MEL2.2 cells, in 22.5 ml of melanoma culture medium (Dulbecco's Modified Eagle's Medium) supplemented with 10% fetal calf serum. After 24 hours, the medium was replaced. Forty eight hours after transfection, the cells were harvested and seeded at $4 \times 10^6$ cells per 80 $cm_2$ flask in melanoma culture medium supplemented with 2 mg/ml of geneticin. The geneticin serves as a selection marker.

EXAMPLE 16

Thirteen days after transfection, geneticin-resistant colonies were counted, harvested, and cultured in nonselective medium for 2 or 3 days. Transfected cells were then plated in 96-well microplates at 200 cells/well in 200 ul of culture medium with 20% fetal calf serum (FCS) in order to obtain approximately 30 growing colonies per well. The number of microcultures was aimed at achieving redundancy, i.e., such that every independent transfectant should be represented at least four times.

After 10 days, wells contained approximately $6 \times 10^4$ cells. These cells were detached, and ⅓ of each microculture was transferred to a duplicate plate. After 6 hours, i.e., after readherence, medium was removed and 1500 anti-E CTL (CTL 82/30), were added to each well in 100 μl of CTL culture medium with 35 U/ml of IL-2. one day later, the supernatant (50 μl) was harvested and examined for TNF concentration, for reasons set forth in the following example.

EXAMPLE 17

The size of the mammalian genome is $6 \times 10^6$ kb. As the average amount of DNA integrated in each drug-resistant transfectant was expected to be about 200 kb, a minimum of 30,000 transfectants would need to be examined to ascertain whether antigen E had been transfected. Prior work with murine cells had shown that when a CTL stimulation assay was used, groups containing only 3% of cells expressing the antigen of interested could be identified. This should reduce the number of assays by a factor of 30. While an anti-E CTL assay, as described supra, in mixed $E^+/E^-$ cells was helpful, it was not sufficient in that consistent results could not be obtained.

As a result, an alternative test was devised. Stimulation of CTLs was studied by release of tumor necrosis factor ("TNF") using well known methodologies which need not be repeated here. As described in Example 15, 1500 CTL 82/30 cells had been added per well of transfectants. These CTLs were collected 6 days after stimulation. As indicated supra, after ⅓ of the cells in each well had been removed and the remaining ⅔ ($4 \times 10^4$) had readhered, the CTLs and IL-2 were added thereto. The 50 μl of supernatant was removed 24 hours later and transferred to a microplate containing $3 \times 10^4$ W13 (WEHI-164 clone 13; Espevik et al., J. Immunol. Meth. 95: 99–105 (1986)) cells in 50 μl of W13 culture medium (RPMI-1640, supplemented with L-arginine (116 mg/l), L-asparagine (36 mg/l), L-glutamine (216 mg/l), and 10% FCS supplemented with 2 μg of actinomycin D at 37% in an 8% $CO_2$ atmosphere. The cell line W13 is a mouse fibrosarcoma cell line sensitive to TNF. Dilutions of recombinant TNF-β in RPMI 1640 were added to target cell controls.

The W13 cultures were evaluated after 20 hours of incubation, and dead cell percentage was measured using an adaptation of the calorimetric assay of Hansen et al., J. Immunol. Meth. 119: 203–210 (1989). This involved adding 50 ml of (3-(4,5-dimethylthiazol-2-yl)-2,5-diphenyl tetrazolium bromide at 2.5 mg/ml in PBS, followed by two hours of incubation at 37° C. Dark blue formazan crystals were dissolved by adding 100 μl of lysis solution (1 volume N,N dimethyl formamide mixed at 37° C. with two volumes of water containing 30% (w/v) sodium dodecyl sulphate, at pH 4.7 from 1.6% acetic acid and 2.5% iN HCl). Plates were incubated at 37° C. overnight, and ODs were taken at 570 nm using 650 nm as control. Dead cell percentage was determined via the formula:

$$100 \times \left[ 1 - \frac{100 - (OD_{570} \text{ sample well})}{OD_{570} \text{ well} + \text{medium}} \right]$$

following Espevik et al., J. Immunol. Meth. 95: 99–105 (1986). The results showed that even when the ratio of $E^+/E^-$ cells was as low as 1/45, significant production of TNF was observed, thus showing active CTLS. This led to the decision to test the drug resistant transfectants in groups of 30.

EXAMPLE 18

Cells were tested for TNF production as discussed in Example 17, supra. A total of 100 groups of $E^-$ cells ($4 \times 10^6$ cells/group) were tested following transfection, and $7 \times 10^4$ independent geneticin resistant transfectants were obtained, for an average of 700 per group. Only one group of transfected cells led to a microculture which caused anti-E antigen CTL clone 82/30 to produce TNF. Of 300 clones tested, 8 were positive. These clones were then tested for lysis by anti-E CTL, using the standard $^{51}Cr$ release assay, and were found to be lysed as efficiently as the original $E^+$ cell line. The transfectant E.T1, discussed herein, had the same lysis pattern as did MEL2.2 for CTLs against antigens B,C,D and F.

The fact that only one transfectant presented the antigen out of 70,000 geneticin resistance transfectants may at first seem very low, but it is not. The work described supra for P815 showed an average frequency of 1/13,000. Human DNA recipient MEL2.2 appears to integrate 5 times less DNA than P1.HTR.

EXAMPLE 19

Once transfectant E.T1 was found, analysis had to address several questions including whether an $E^+$ contaminant of the cell population was the cause. The analysis of antigen presentation, described supra, shows that E.T1 is B⁻ and C⁻, just like the recipient cell MEL2.2. It was also found to be HPRT⁻, using standard selection procedures. All E⁺cells used in the work described herein, however, were HPRT⁺.

It was also possible that an E⁺ revertant of MEL2.2 was the source for E.T1. To test this, the observation by Perucho et al., Cell 22: 309–317 (1980), that cotransfected sequences usually integrate together at a single location of recipient genome was employed. If antigen E in a transfectant results from cotransfection with pSVtkneoB, then sequences should be linked and deletion of the antigen might also delete the neighboring pSVtkneoβ sequences. Wölfel et al., supra has shown this to be true. If a normally E⁻ cell is transfected with pSVtkneoβ, then sequences should be linked and deletion of the antigen might also delete the neighboring pSVtkneoβ sequences. If a normally E⁺ cell transfected with pSVtkneoβ is E.T1, however, "co-deletion" should not take place. To test this, the transfectant E.T1 was subjected to immunoselection with 82/30, as described supra. Two antigen loss variants were obtained, which resisted lysis by this CTL. Neither of these had lost geneticin resistance; however, Southern blot analysis showed loss of several neo$^r$ sequences in the variants, showing close linkage between the E gene and neo$^r$ gene in E.T1, leading to the conclusion that E.T1 was a transfectant.

EXAMPLE 20

The E⁺ subclone MZ2-MEL 4B was used as a source of DNA for preparation of a cosmid library. This library of nearly 700,000 cosmids was transfected into MZ2-MEL 2.2 cells, following the cosmid transfection protocols described supra.

By packaging the DNA of cosmid transfectants directly into lambda phase components, it is sometimes possible to retrieve cosmids that contain the sequences of interest. This procedure was unsuccessful here, so we rescued the transfected sequence by ligating DNA of the transfectant to appropriate restriction fragments of cosmid vector pTL6. This was tried with two transfectants and was successful with one of them. One cosmid, referred to as B3, was recovered from this experiment, and subjected to restriction endonuclease digestion via XmaI, or by BamHI digestion of a large, 12 kb XmaI transfected fragment. The fragments were cloned into vector pTZ 18R, and then transfected into MEL2.2. Again, TNF production was the measure by which successful transfection was determined. The experiments led to the determination of a gene sequence capable of transfecting antigen E on the 12 kb XmaI fragment, and then on the 2.4 kb fragment of BamHI digestion of the 12 kb segment.

Figure 12:
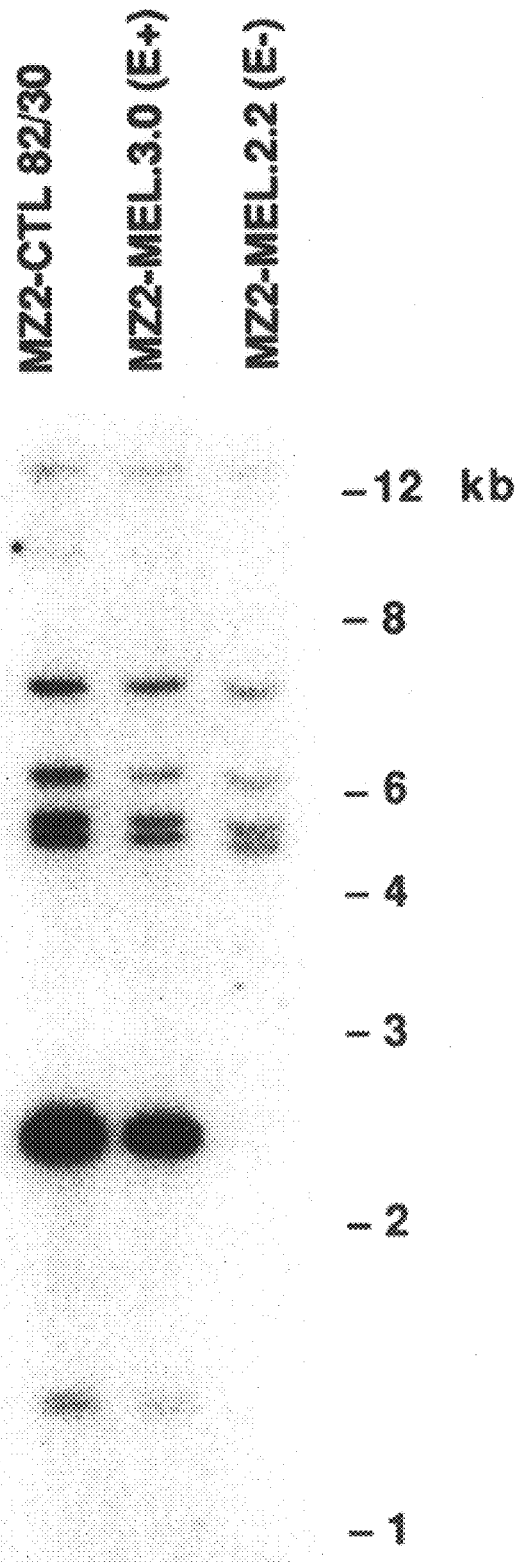
FIG. 12 shows Southern Blot experiments using the various human melanoma cell lines employed in this application.

The 2.4 kb fragment hybridizes with a 2.4 kb fragment from MZ2-MEL and with a T cell clone of patient MZ-2, as determined by Southern Blots (BamHI/SmaI digested DNA). The band is absent from E⁻ antigen loss variants of MZ2-MEL, as seen in FIG. 12.

The sequence for the E antigen precursor gene has been determined, and is presented herein:

|      |            | \|  10      | \|  20     | \|  30     | \|  40     | \|  50     | \|  60     |      |
|------|------------|-------------|------------|------------|------------|------------|------------|------|
| 1    | GGATCCAGGC | CCTGCCAGGA  | AAAATATAAG | GGCCCTGCGT | GAGAACAGAG | GGGGTCATCC |            | 60   |
| 61   | ACTGCATGAG | AGTGGGGATG  | TCACAGAGTC | CAGCCCACCC | TCCTGGTACG | ACTGAGAAGC |            | 120  |
| 121  | CAGGGCTGTG | CTTGCGGTCT  | GCACCCTGAG | GGCCCGTGGA | TTCCTCTTCC | TGGAGCTCCA |            | 180  |
| 181  | GGAACCAGGC | AGTGAGGCCT  | TGGTCTGAGA | CAGTATCCTC | AGGTCACAGA | GCAGAGGATG |            | 240  |
| 241  | CACAGGGTGT | GCCAGCAGTG  | AATGTTTGCC | CTGAATGCAC | ACCAAGGGCC | CCACCTGCCA |            | 300  |
| 301  | CAGGACACAT | AGGACTCCAC  | AGAGTCTGGC | CTCACCTCCC | TACTGTCAGT | CCTGTACAAT |            | 360  |
| 361  | CGACCTCTGC | TGGCCGGCTG  | TACCCTGAGT | ACCCTCTCAC | TTCCTCCTTC | AGGTTTTCAG |            | 420  |
| 421  | GGGACAGGCC | AACCCAGAGG  | ACAGGATTCC | CTGGAGGCCA | CAGAGGAGCA | CCAAGGAGAA |            | 480  |
| 481  | GATCTGTAAG | TAGGCCTTTG  | TTAGAGTCTC | CAAGGTTCAG | TTCTCAGCTG | AGGCCTCTCA |            | 540  |
| 541  | CACACTCCCT | CTCTCCCCAG  | GCCTGTGGGT | CTTCATTGCC | CAGCTCCTGC | CCACACTCCT |            | 600  |
| 601  | GCCTGCTGCC | CTGACGAGAG  | TCATCATGTC | TCTTGAGCAG | AGGAGTCTGC | ACTGCAAGCC |            | 660  |
| 661  | TGAGGAAGCC | CTTGAGGCCC  | AACAAGAGGC | CCTGGGCTGG | TGTGTGTGCA | GGCTGCCACC |            | 720  |
| 721  | TCCTCCTCCT | CTCCTCTGGT  | CCTGGGCACC | CTGGAGGAGG | TGCCCACTGC | TGGGTCAACA |            | 780  |
| 781  | GATCCTCCCC | AGAGTCCTCA  | GGGAGCCTCC | GCCTTTCCCA | CTACCATCAA | CTTCACTCGA |            | 840  |
| 841  | CAGAGGCAAC | CCAGTGAGGG  | TTCCAGCAGC | CGTGAAGAGG | AGGGGCCAAG | CACCTCTTGT |            | 900  |
| 901  | ATCCTGGAGT | CCTTGTTCCG  | AGCAGTAATC | ACTAAGAAGG | TGGCTGATTT | GGTTGGTTTT |            | 960  |
| 961  | CTGCTCCTCA | AATATCGAGC  | CAGGGAGCCA | GTCACAAAGG | CAGAAATGCT | GGAGAGTGTC |            | 1020 |
| 1021 | ATCAAAAATT | ACAAGCACTG  | TTTTCCTGAG | ATCTTCGGCA | AAGCCTCTGA | GTCCTTGCAG |            | 1080 |
| 1081 | CTGGTCTTTG | GCATTGACGT  | GAAGGAAGCA | GACCCCACCG | GCCACTCCTA | TGTCCTTGTC |            | 1140 |
| 1141 | ACCTGCCTAG | GTCTCTCCTA  | TGATGGCCTG | CTGGGTGATA | ATCAGATCAT | GCCCAAGACA |            | 1200 |
| 1201 | GGCTTCCTGA | TAATTGTCCT  | GGTCATGATT | GCAATGGAGG | GCGGCCATGC | TCCTGAGGAG |            | 1260 |

```
1261  GAAATCTGGG  AGGAGCTGAG  TGTGATGGAG  GTGTATGATG  GGAGGGAGCA  CAGTGCCTAT  1320

1321  GGGGAGCCCA  GGAAGCTGCT  CACCCAAGAT  TTGGTGCAGG  AAAAGTACCT  GGAGTACGGC  1380

1381  AGGTGCCGGA  CAGTGATCCC  GCACGCTATG  AGTTCCTGTG  GGGTCCAAGG  GCCCTCGCTG  1440

1441  AAACCAGCTA  TGTGAAAGTC  CTTGAGTATG  TGATCAAGGT  CAGTGCAAGA  GTTCGCTTTT  1500

1501  TCTTCCCATC  CCTGCGTGAA  GCAGCTTTGA  GAGAGGAGGA  AGAGGGAGTC  TGAGCATGAG  1560

1561  TTGCAGCCAA  GGCCAGTGGG  AGGGGACTG   GGCCAGTGCA  CCTTCCAGGG  CCGCGTCCAG  1620

1621  CAGCTTCCCC  TGCCTCGTGT  GACATGAGGC  CCATTCTTCA  CTCTGAAGAG  AGCGGTCAGT  1680

1681  GTTCTCAGTA  GTAGGTTTCT  GTTCTATTGG  GTGACTTGGA  GATTTATCTT  TGTTCTCTTT  1740

1741  TGGAATTGTT  CAAATGTTTT  TTTTTAAGGG  ATGGTTGAAT  GAACTTCAGC  ATCCAAGTTT  1800

1801  ATGAATGACA  GCAGTCACAC  AGTTCTGTGT  ATATAGTTTA  AGGGTAAGAG  TCTTGTGTTT  1860

1861  TATTCAGATT  GGGAAATCCA  TTCTATTTTG  TGAATTGGGA  TAATAACAGC  AGTGGAATAA  1920

1921  GTACTTAGAA  ATGTGAAAAA  TGAGCAGTAA  AATAGATGAG  ATAAAGAACT  AAAGAAATTA  1980

1981  AGAGATAGTC  AATTCTTGCC  TTATACCTCA  GTCTATTCTG  TAAAATTTTT  AAAGATATAT  2040

2041  GCATACCTGG  ATTTCCTTGG  CTTCTTTGAG  AATGTAAGAG  AAATTAAATC  TGAATAAAGA  2100

2101  ATTCTTCCTG  TTCACTGGCT  CTTTTCTTCT  CCATGCACTG  AGCATCTGCT  TTTTGGAAGG  2160

2161  CCCTGGGTTA  GTAGTGGAGA  TGCTAAGGTA  AGCCAGACTC  ATACCCACCC  ATAGGGTCGT  2220

2221  AGAGTCTAGG  AGCTGCAGTC  ACGTAATCGA  GGTGGCAAGA  TGTCCTCTAA  AGATCTAGGG  2280

2281  AAAAGTGAGA  GAGGGGTGAG  GGTGTGGGGC  TCCGGGTGAG  AGTGGTGGAG  TGTCAATGCC  2340

2341  CTGAGCTGGG  GCATTTTGGG  CTTTGGGAAA  CTGCAGTTCC  TTCTGGGGGA  GCTGATTGTA  2400

2401  ATGATCTTGG  GTGGATCC                                                    2418

|    10      |    20      |    30      |    40      |    50      |    60
```

EXAMPLE 21

After the 2.4 kb genomic segment had been identified, studies were carried out to determine if an "E⁺" subline expressed any homologous DNA. Cell line MZ2-MEL 3.0 was used as a source, and a cDNA library was prepared from its mRNA, using art known techniques. The 2.4 kb segment was used as a probe, and mRNA of about 1.8 kb was identified as homologous, using Northern blot analysis. When cDNA was screened, clones were obtained showing almost complete identity to parts of the 2.4 kb fragment. Two exons were thus identified. An additional exon was located upstream of these, via sequencing segments of cosmid B3 located in front of the 2.4 kb BamHI fragment. The gene extends over about 4.5 kb, as shown in FIG. 8. The starting point of the transcribed region was confirmed using PCR for the 5' end of the cDNA. The three exons comprise 65, 73, and 1551 base pairs. An ATG is located at position 66 of exon 3, followed by an 828 base pair reading frame.

EXAMPLE 22

To determine if smaller segments of the 2.4 kb fragment could transfer the expression of antigen E, smaller pieces corresponding to the larger gene were prepared, using art recognized techniques, and transferred into E⁻ cells. FIG. 8 shows the boundaries of the three segments.

Transfer of antigen expression in this manner indicates that the gene codes for the antigen precursor, rather than coding for a protein which activates the antigen.

EXAMPLE 23

The probing of CDNA described supra revealed, surprisingly, two different but closely related cDNAs. These cDNAs, when tested, did not transfer expression of antigen E, but they do show substantial homology to the first cDNA segment. The three segments, appear to indicate a newly recognized family of genes, referred to as "MAGE" for "melanoma antigen". In FIG. 9, "mage-1" directs expression of the antigen from MZ2 cells. Portions of the third exon of each gene are presented in FIG. 9. The second and third sequences are more closely related to each other than the first (18.1 and 18.9% difference compared to the first; 12% with each other). Out of 9 cDNA clones obtained, three of each type were obtained, suggesting equal expression. "MAGE" as used hereafter refers to a family of molecules, and the nucleic acids coding for them. These nucleic acids share a certain degree of homology and are expressed in tumor cells including several types of human tumor cells as well as in human tumors. The family is referred to as "MAGE" because the first members were identified in human melanoma cells. As the experiments which follow indicate, however, the members of the MAGE family are not at all restricted to melanoma tumors; rather, MAGE refers to a family of tumor rejection antigen precursors and the nucleic acid sequences coding therefore. The antigens resulting therefrom are referred to herein as "MAGE TRAS" or "melanoma antigen tumor rejection antigens"

EXAMPLE 24

Experiments with mouse tumors have demonstrated that new antigens recognized by T cells can result from point mutations that modify active genes in a region that codes for the new antigenic peptide. New antigens can also arise from the activation of genes that are not expressed in most normal cells. To clarify this issue for antigen MZ2-E, the mage-1 gene present in the melanoma cells was compared to that present in normal cells of patient MZ2. Amplification by polymerase chain reaction (PCR) of DNA of phytohemagglutinin-activated blood lymphocytes using primers surrounding a 1300 bp stretch covering the first half of the 2.4 kb fragment was carried out. As expected, a PCR product was obtained whereas none was obtained with the DNA of the E⁻ variant. The sequence of this PCR product proved identical to the corresponding sequence of the gene carried by the E⁺ melanoma cells. Moreover, it was found that antigen MZ2-E was expressed by cells transfected with the cloned PCR product. This result suggests that the activation of a gene normally silent is responsible for the appearance of tumor rejection antigen MZ2-E.

EXAMPLE 25

Figure 10:
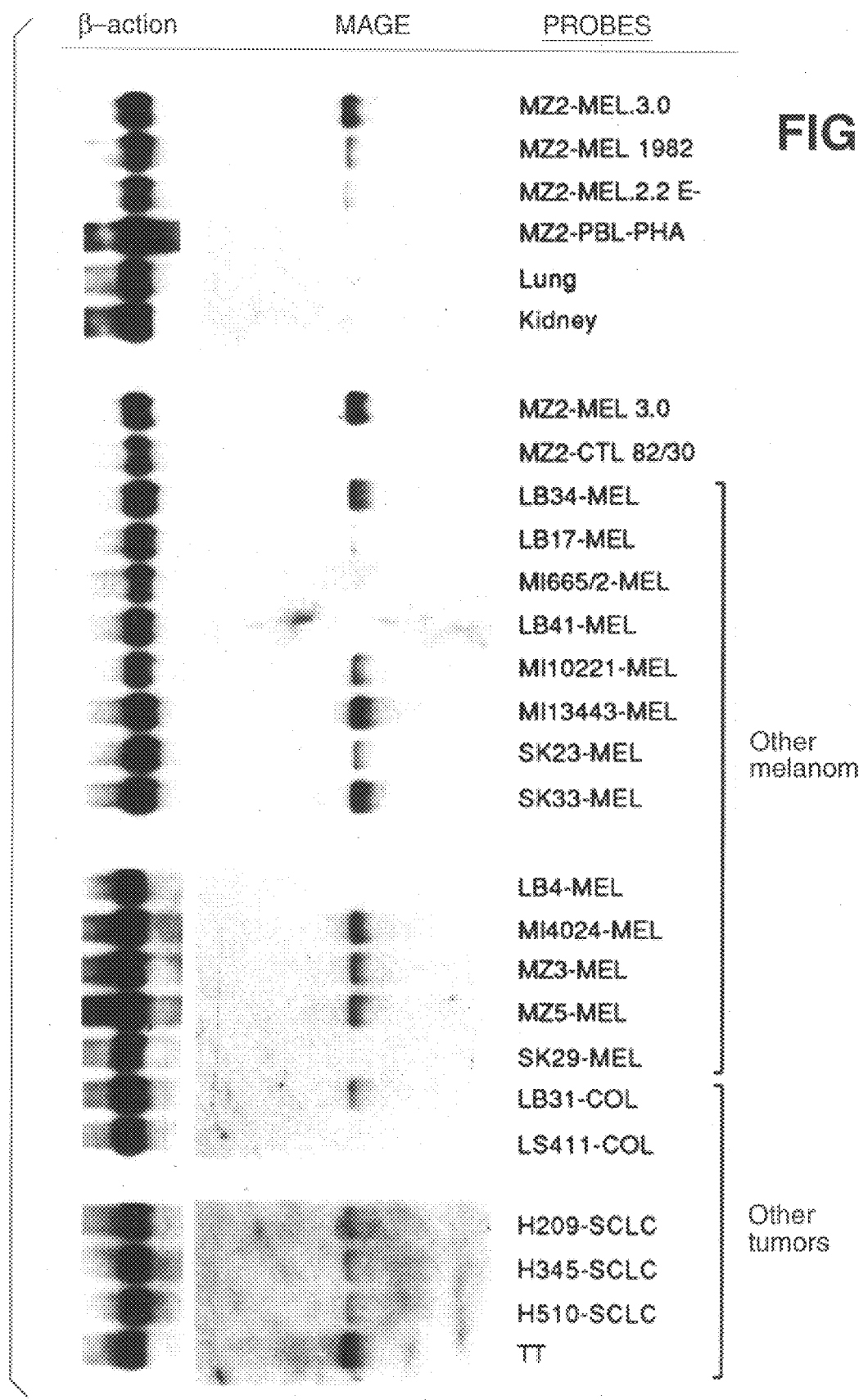
FIG. 10 shows the result of Northern blots for MAGE genes on various tissues.

In order to evaluate the expression of gene mage-1 by various normal and tumor cells, Northern blots were hybridized with a probe covering most of the third exon. In contrast with the result observed with human tumor cell line MZ2-MEL 3.0, no band was observed with RNA isolated from a CTL clone of patient MZ2 and phytohemagglutinin-activated blood lymphocytes of the same patient. Also negative were several normal tissues of other individuals (FIG. 10 and FIG. 11). Fourteen melanoma cell lines of other patients were tested. Eleven were positive with bands of varying intensities. In addition to these culture cell lines, four samples of melanoma tumor tissue were analyzed. Two samples, including a metastasis of patient MZ2 proved positive, excluding the possibility that expression of the gene represented a tissue culture artefact. A few tumors of other histological types, including lung tumors were tested. Most of these tumors were positive (FIGS. 10 and 11). These results indicated that the MAGE gene family is expressed by many melanomas and also by other tumors. However, they provided no clear indication as to which of genes mage-1, 2 or 3 were expressed by these cells, because the DNA probes corresponding to the three genes cross-hybridized to a considerable extent. To render this analysis more specific, PCR amplification and hybridization with highly specific oligo-nucleotide probes were used. cDNAs were obtained and amplified by PCR using oligonucleotide primers corresponding to sequences of exon 3 that were identical for the three MAGE genes discussed herein. The PCR products were then tested for their ability to hybridize to three other oligonucleotides that showed complete specificity for one of the three genes (FIG. 9). Control experiments carried out by diluting RNA of melanoma MZ2-MEL 3.0 in RNA from negative cells indicated that under the conditions used herein the intensity of the signal decreased proportionally to the dilution and that positive signals could still be detected at a dilution of $\frac{1}{300}$. The normal cells (lymphocytes) that were tested by PCR were confirmed to be negative for the expression of the three MAGE genes, suggesting therefore a level of expression of less than $\frac{1}{300}^{th}$ that of the MZ2 melanoma cell line (FIG. 11). For the panel of melanoma cell lines, the results clearly showed that some melanomas expressed MAGE genes mage 1, 2 and 3 whereas other expressed only mage-2 and 3 (FIGS. 11 and 10). Some of the other tumors also expressed all three genes whereas others expressed only mage-2 and 3 or only mage-3. It is impossible to exclude formally that some positive PCR results do not reflect the expression of one of the three characterized MAGE genes but that of yet another closely related gene that would share the sequence of the priming and hybridizing oligonucleotides. It can be concluded that the MAGE gene family is expressed by a large array of different tumors and that these genes are silent in the normal cells tested to this point.

EXAMPLE 26

Figure 13:
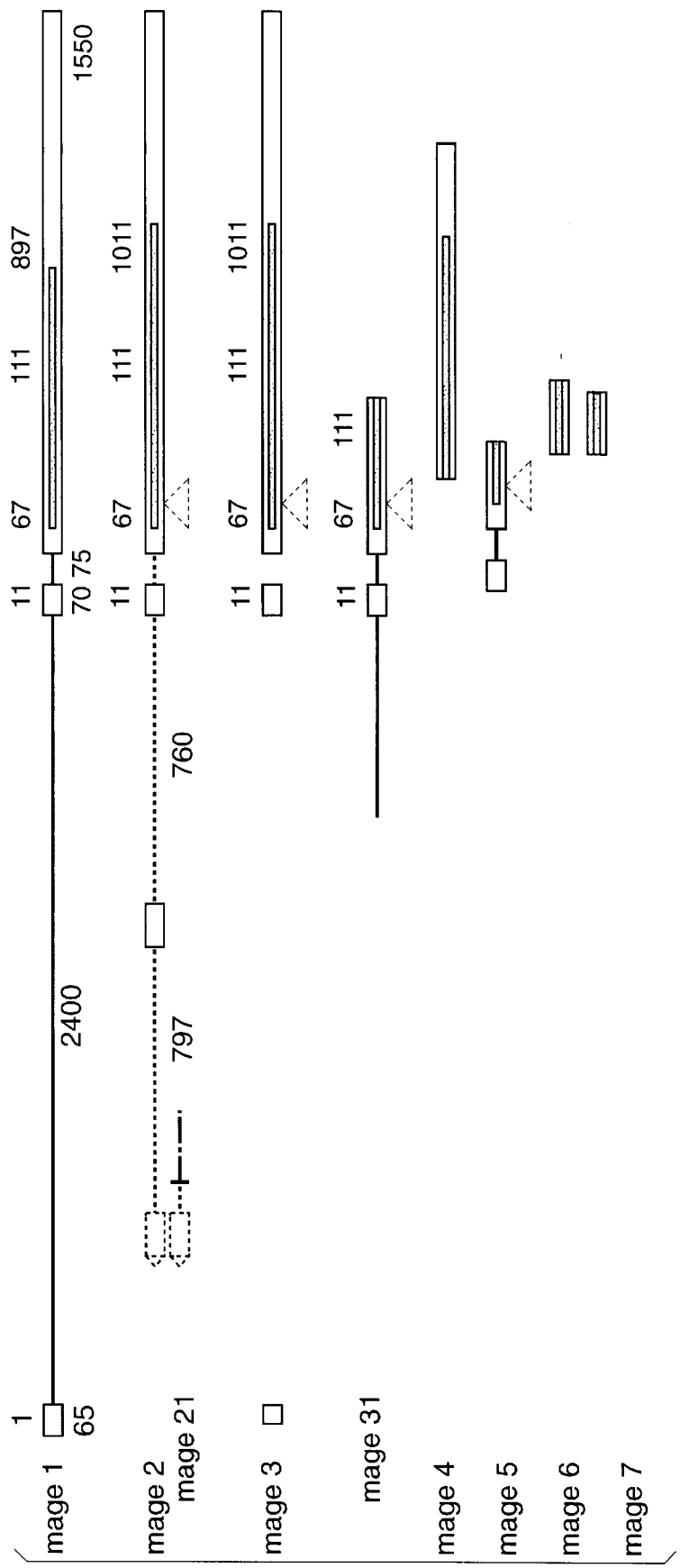
FIG. 13 is a generalized schematic of the expression of MAGE 1, 2 and 3 genes by tumor and normal tissues.

The availability of a sequence that transfects at high efficiency and efficiently expresses a TRAP made it possible to search for the associated major histo-compatibility complex (MHC) class I molecule. The class I specificities of patient MZ2 are HLA-A1, A29, B37, B44 and C6. Four other melanomas of patients that had A1 in common with MZ2 were cotransfected with the 2.4 kb fragment and pSVtkneoβ. Three of them yielded neo$^r$ transfectants that stimulated TNF release by anti-E CTL clone 82/30, which is CD8+ (FIG. 10). No E- transfectant was obtained with four other melanomas, some of which shared A29, B44 or C6 with MZ2. This suggests that the presenting molecule for antigen MZ2-E is HLA-A1. In confirmation, it was found that, out of 6 melanoma cell lines derived from tumors of HLA-A1 patients, two stimulated TNF release by anti-E CTL clone 82/30 of patient MZ2. One of these tumor cell lines, MI13443-MEL also showed high sensitivity to lysis by these anti-E CTL. These two melanomas were those that expressed mage-1 gene (FIG. 13). Eight melanomas of patients with HLA haplotypes that did not include A1 were examined for their sensitivity to lysis and for their ability to stimulate TNF release by the CTL. None was found to be positive. The ability of some human anti-tumor CTL to lyse allogeneic tumors sharing an appropriate HLA specificity with the original tumor has been reported previously (Darrow, et al., J. Immunol. 142: 3329 (1989)). It is quite possible that antigenic peptides encoded by genes mage 2 and 3 can also be presented to autologous CTL by HLA-A1 or other class I molecules, especially in view of the similar results found with murine tumors, as elaborated upon supra.

EXAMPLE 27

As indicated supra, melanoma MZ2 expressed antigens F, D and A', in addition to antigen E. Following the isolation of the nucleic acid sequence coding for antigen E, similar experiments were carried out to isolate the nucleic acid sequence coding for antigen F.

To do this, cultures of cell line MZ2-MEL2.2, an E⁻ cell line described supra, were treated with anti-F CTL clone 76/6, in the same manner described for treatment with anti-E CTL clones. This resulted in the isolation of an F antigen loss variant, which was then subjected to several rounds of selection. The resulting cell line, "MZ2-MEL2.2.5" was completely resistant to lysis by anti-F CTLS, yet proved to be lysed by anti-D CTLs.

Again, following the protocols set forth for isolation of antigen -E precursor DNA, the F⁻ variant was transfected with genomic DNA from F⁺ cell line MZ2-MEL3.0. The experiments yielded 90,000 drug resistant transfectants. These were tested for MZ2-F expression by using pools of 30 cells in the TNF detection assay elaborated upon supra. One pool stimulated TNF release by anti-F CTLs, and was cloned. Five of 145 clones were found to stimulate anti-F CTLS. Lysis assays, also following protocols described supra, confirmed (i) expression of the gene coding for antigen F, and (ii) presentation of antigen F itself.

EXAMPLE 28

Following identification of F⁺ cell lines, the DNA therefrom was used to transfect cells. To do this, a cosmid library of F+ cell line MZ2-MEL.43 was prepared, again using the protocols described supra. The library was divided into 14 groups of about 50,000 cosmids, and DNA from each group was transfected into MZ2-MEL2.2.5. Transfectants were then tested for their ability to stimulate TNF release from anti-F CTL clone 76/6. Of 14 groups of cosmids, one produced two independent transfectants expressing antigen F; a yield of two positives out of 17,500 geniticin resistant transfectants.

EXAMPLE 29

The existence of a gene family was suggested by the pattern observed on the Southern blot (FIG. 12). To do this, the 2.4 kb BamHI fragment, which transferred the expression of antigen M22-E, was labelled with 32p and used as a probe on a Southern Blot of BamHI digested DNA of E+cloned subclone M22-MEL2.2. Hybridization conditions included 50 $\mu$l/cm$^2$ of 3.5×SSC, 1×Denhardt's solution; 25 mM sodium phosphate buffer (pH 7.0), 0.5% SDS, 2mM EDTA, where the 2.4 kb probes had been labelled with [$\alpha^{32}$p]dCTP (2–3000 Ci/mole), at 3×10$^6$ cpm/ml. Hybridization was carried out for 18 hours at 65° C. After this, the membranes were washed at 65° C. four times for one hour each in 2×SSC, 0.1% SDS, and finally for 30 minutes in 0.1×SSC, 0.1% SDS. To identify hybridization, membranes were autoradiographed using Kodak X-AR film and Kodak X-Omatic fine intensifying screens.

In the following examples, whenever "hybridization" is referred to, the stringency conditions used were similar to those described supra. "Stringent conditions" as used herein thus refers to the foregoing conditions; subject to routine, art recognized modification.

EXAMPLE 30

The cDNA coding for mage 4 was identified from a sample of the human sarcoma cell line LB23-SAR. This cell line was found to not express mage 1, 2 or 3, but the mRNA of the cell line did hybridize to the 2.4 kb sequence for mage 1. To study this further, a cDNA library was prepared from total LB23-SAR mRNA, and was then hybridized to the 2.4 kb fragment. A cDNA sequence was identified as hybridizing to this probe, and is identified hereafter as mage 4.

EXAMPLE 31

Experiments were carried out using PHA-activated lymphocytes from patient "MZ2", the source of the "MZ" cells discussed supra. An oligonucleotide probe which showed homology to mage 1 but not mage 2 or 3 was hybridized with a cosmid library derived from the PHA activated cells. The size of the hybridizing BamHI cosmid fragment, however, was 4.5 kb, thus indicating that the material was not mage 1; however, on the basis of homology to mage 1–4, the fragment can be referred to as "mage 5". The sequence of MAGE 5 is presented in SEQ ID NO: 16.

EXAMPLE 32

Melanoma cell line LB-33-MEL was tested. Total mRNA from the cell line was used to prepare cDNA, which was then amplified with oligos CHO9: (ACTCAGCTCCTCCCAGATTT), and CHO10: (GAAGAGGAGGGGCCAAG). These oligos correspond to regions of exon 3 that are common to previously described mage 1, 2 and 3.

To do this, 1 gg of RNA was diluted to a total volume of 20 $\mu$l, using 2 $\mu$l of 10×PCR buffer, 2 $\mu$l of each of 10 mM dNTP, 1.2 $\mu$l of 25 mM MgCl$_2$, 1 $\mu$l of an 80 mM solution of CHO9, described supra, 20 units of RNAsin, and 200 units of M-MLV reverse transcriptase. This was followed by incubation for 40 minutes at 42° C. PCR amplification followed, using 8 $\mu$l of 10×PCR buffer, 4.8 $\mu$l of 25 mM MgCl$_2$, 1 $\mu$l of CHO10, 2.5 units of Thermus acquaticus ("Taq") polymerase, and water to a total volume of 100 $\mu$l. Amplification was then carried out for 30 cycles (1 minute 94° C.; 2 minutes at 52° C., 3 minutes at 72° C.). Ten $\mu$l of each reaction were then size fractionated on agarose gel, followed by nitrocellulose blotting. The product was found to hybridize with oligonucleotide probe CHO18 (TCTTGTATCCTGGAGTCC). This probe identified mage 1 but not mage 2 or 3. However, the product did not hybridize to probe SEQ 4 (TTGCCAAGATCTCAGGAA). This probe also binds mage 1 but not 2 and 3. This indicated that the PCR product contained a sequence that differed from mage 1, 2 and 3. Sequencing of this fragment also indicated differences with respect to mage 4 and 5. These results indicate a sequence differing from previously identified mage 1, 2, 3, 4 and 5, and is named mage 6.

EXAMPLE 33

In additional experiments using cosmid libraries from PHA-activated lymphocytes of MZ2, the 2.4 kb mage 1 fragment was used as a probe and isolated a complementary fragment. This clone, however, did not bind to oligonucleotides specific for mage 1, 2, 3 or 4. The sequence obtained shows some homology to exon 3 of mage 1, and differs from mages 1–6. It is referred to as mage 7 hereafter. Additional screenings yielded mage 8–11.

EXAMPLE 34

The usefulness of the TRAPs, as well as TRAs derived therefrom, was exemplified by the following.

Exon 3 of mage 1 was shown to transfer expression of antigen E. As a result, it was decided to test whether synthetic peptides derived from this exon 3 could be used to confer sensitivity to anti-E CTL.

To do this, and using standard protocols, cells normally insensitive to anti-E/CTLs were incubated with the synthetic peptides derived from Exon 3.1. Using the CTL lytic assays described supra on P815A, and a peptide concentration of 3 mM, the peptide Glu-Ala-Asp-Pro-Thr-Gly-His-Ser-Tyr was shown to be best. The assay showed lysis of 30%, indicating conferring of sensitivity to the anti-E CTL.

EXAMPLE 35

Nucleic acid sequences referred to as "smage" were isolated from murine cells. Using the protocols described supra, a cosmid library was prepared from the DNA of normal DBA/2 kidney cells, using cosmid vector C2RB. As a probe, the 2.4 kb BamHI fragment of MAGE-1 was used. The DNA was blotted to nylon filters, and these were washed in 2×SSC at 65° C. to identify the smage material.

EXAMPLE 36

Further tissue samples were tested for the presence of MAGE genes, using the protocols discussed supra. Some of these results follow.

There was no expression of the MAGE genes in brain or kidney tumor tissue. Colon tumor tissue showed expression of MAGE 1, 2, 3 and 4, although not all tumors tested showed expression of all MAGE genes. This is also true for pancreatic tumor (MAGE 1); non-small cell lung (MAGE 1, 2, 3 and 4), prostate (MAGE 1), sarcomas (MAGE 1, 2, 3 and 4), breast (MAGE 1, 2 and 3), and larynx (MAGE 1 and 4).

The foregoing disclosure, including the examples, places many tools of extreme value in the hands of the skilled artisan. To begin, the examples identify and provide a methodology for isolating nucleic acid molecules which code for tumor rejection antigen precursors as well as the nucleic acid molecules complementary thereto. It is known that DNA exists in double stranded form, and that each of the two strands is complementary to the other. Nucleic acid hybridization technology has developed to the point where, given a strand of DNA, the skilled artisan can isolate its complement, or synthesize it.

"Nucleic acid molecule" as used herein refers to all species of DNA and RNA which possess the properties discussed supra. Genomic and complementary DNA, or "cDNA" both code for particular proteins, and as the examples directed to isolation of MAGE coding sequences show, this disclosure teaches the artisan how to secure both of these.

Similarly, RNA molecules, such as mRNA can be secured. Again, with reference to the skilled artisan, once one has a coding sequence in hand, mRNA can be isolated or synthesized.

Complementary sequences which do not code for TRAP, such as "antisense DNA" or mRNA are useful, e.g., in probing for the coding sequence as well as in methodologies for blocking its expression.

It will also be clear that the examples show the manufacture of biologically pure cultures of cell lines which have been transfected with nucleic acid sequences which code for or express the TRAP molecules. Such cultures can be used as a source for tumor rejection antigens, e.g., or as therapeutics. This aspect of the invention is discussed infra.

Cells transfected with the TRAP coding sequences may also be transfected with other coding sequences. Examples of other coding sequences include cytokine genes, such as interleukins (e.g., IL-2 or IL-4), or major histo-compatibility complex (MHC) or human leukocyte antigen (HLA) molecules. Cytokine gene transfection is of value because expression of these is expected to enhance the therapeutic efficacy of the biologically pure culture of the cells in vivo. The art is well aware of therapies where interleukin transfectants have been administered to subjects for treating cancerous conditions. In a particularly preferred embodiment, cells are transfected with sequences coding for each of (i) a TRAP molecule, (ii) an HLA/MHC molecule, and (iii) a cytokine.

Transfection with an MHC/HLA coding sequence is desirable because certain of the TRAs may be preferentially or specifically presented only by particular MHC/HLA molecules. Thus, where a recipient cell already expresses the MHC/HLA molecule associated with presentation of a TRA, additional transfection may not be necessary although further transformation could be used to cause over-expression of the antigen. On the other hand, it may be desirable to transfect with a second sequence when the recipient cell does not normally express the relevant MHC/HLA molecule. It is to be understood, of course, that transfection with one additional sequence does not preclude further transfection with other sequences.

The term "biologically pure" as used in connection with the cell line described herein simply means that these are essentially free of other cells. Strictly speaking, a "cell line" by definition is "biologically pure", but the recitation will establish this fully.

Transfection of cells requires that an appropriate vector be used. Thus, the invention encompasses expression vectors where a coding sequence for the TRAP of interest is operably linked to a promoter. The promoter may be a strong promoter, such as those well known to the art, or a differential promoter, i.e., one which is operative only in specific cell types. The expression vectors may also contain all or a part of a viral or bacterial genome, such as vaccinia virus or BCG. Such vectors are especially useful in preparing vaccines.

The expression vectors may incorporate several coding sequences, as long as the TRAP sequence is contained therein. The cytokine and/or MHC/HLA genes discussed sunra may be included in a single vector with the TRAP sequence. Where this is not desired, then an expression system may be provided, where two or more separate vectors are used where each coding sequence is operably linked to a promoter. Again, the promoter may be a strong or differential promoter. Co-transfection is a well known technique, and the artisan in this field is expected to have this technology available for utilization. The vectors may be constructed so that they code for the TRA molecule directly, rather than the TRAP molecule. This eliminates the need for post-translational processing.

As the foregoing discussion makes clear, the sequences code for "tumor rejection antigen precursors" ("TRAPs") which, in turn, are processed into tumor rejection antigens ("TRAs"). Isolated forms of both of these categories are described herein, including specific examples of each. Perhaps their most noteworthy aspect is as vaccines for treating various cancerous conditions. The evidence points to presentation of TRAs on tumor cells, followed by the development of an immune response and deletion of the cells. The examples show that when various TRAs are administered to cells, a CTL response is mounted and presenting cells are deleted. This is behavior characteristic of vaccines, and hence TRAPs, which are processed into TRAs, and the TRAs themselves may be used, either alone or in pharmaceutically appropriate compositions, as vaccines. Similarly, presenting cells may be used in the same manner, either alone or as combined with ingredients to yield pharmaceutical compositions. Additional materials which may be used as vaccines include isolated cells which present the TRA molecule on their surface, as well as TRAP fragments, mutated viruses, especially etiolated forms, and transfected bacteria. "Fragments" as used herein refers to peptides which are smaller than the TRA, but which possess the properties required of a vaccine, as discussed supra. Another vaccine comprises or consists of complexes of TRA and HLA molecule. Vaccines of the type described herein may be used preventively, i.e., via administration to a subject in an amount sufficient to prevent onset of a cancerous condition.

The generation of an immune response, be it T-cell or B-cell related, is characteristic of the effect of the presented tumor rejection antigen. With respect to the Bcell response, this involves, inter alia, the generation of antibodies to the TRA, i.e., which specifically bind thereto. In addition, the TRAP molecules are of sufficient size to render them immunogenic, and antibodies which specifically bind thereto are a part of this invention. These antibodies may be polyclonal or monoclonal, the latter being prepared by any of the well recognized methodologies for their preparation which need not be repeated here. For example, mAbs may be prepared using an animal model, e.g., a Balb/C mouse or in a test tube, using, e.g., EBV transformants. In addition, antiserum may be isolated from a subject afflicted with a cancerous condition where certain cells present a TRA. Such antibodies may also be generated to epitopes defined by the interaction of TRA and HLA/MHC molecules.

Review of the foregoing disclosure will show that there are a number of facets to the system which may be referred to as "tumor rejection antigen presentation and recognition". Recognition of these phenomena has diagnostic consequences. For example, the existence of specific CTL clones, or antibodies to the TRA makes it possible to diagnose or monitor cancerous conditions (explained infra), by monitoring the CTLs in a sample from a subject, binding of antibodies to TRAs, or the activity of anti-TRA CTLs in connection with subject samples. Similarly, the expression of nucleic acid molecules for TRAPs can be monitored via amplification (e.g., "polymerase chain reaction"), anti-sense hybridization, probe technologies, and so forth. Various subject samples, including body fluids (blood, serum, and other exudates, e.g.), tissues and tumors may be so assayed.

A particular manner of diagnosis is to use an adaptation of the standard "tuberculin test" currently used for diagnosis of tuberculosis. This standard skin test administers a stable form of "purified protein derivative" or "PPD" as a diagnostic aid. In a parallel fashion, TRAs in accordance with this invention may be used in such a skin test as a diagnostic aid or monitoring method.

The term "cancerous condition" is used herein to embrace all physiological events that commence with the initiation of the cancer and result in final clinical manifestation. Tumors do not spring up "ab initio" as visible tumors; rather there are various events associated with the transformation of a normal cell to malignancy, followed by development of a growth of biomass, such as a tumor, metastasis, etc. In addition, remission may be conceived of as part of "a cancerous condition" as tumors seldom spontaneously disappear. The diagnostic aspects of this invention include all events involved in carcinogenesis, from the first transformation to malignancy of a single cell, through tumor development and metastasis, as well as remission. All are embraced herein.

Where "subject" is used, the term embraces any species which can be afflicted with a cancerous condition. This includes humans and non-humans, such as domesticated animals, breeding stock, and so forth.

There are therapeutic aspects of this invention as well. The efficacy of administration of effective amounts of TRAPs and TRAs as vaccines has already been discussed supra. Similarly, one may develop the specific CTLs in vitro and then administer these to the subject. Antibodies may be administered, either polyclonal or monoclonal, which specifically bind to cells presenting the TRA of interest. These antibodies may be coupled to specific antitumor agents, including, but not being limited to, methotrexate radioiodinated compounds, toxins such as ricin, other cytostatic or cytolytic drugs, and so forth. Thus, "targeted" antibody therapy is included herein, as is the application of deletion of the cancerous cells by the use of CTLs.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. Isolated tumor rejection antigen consisting of the amino acid sequence of SEQ ID NO:26.

\* \* \* \* \*

UNITED STATES PATENT AND TRADEMARK OFFICE
CERTIFICATE OF CORRECTION

PATENT NO. : 5,925,729
DATED : July 20, 1999
INVENTOR(S) : Boon et al.

It is certified that error appears in the above-indentified patent and that said Letters Patent is hereby corrected as shown below:

In column 2, line 56, change "EKBO" to read as -- EMBO --.
In column 2, line 63, change "surra" to read as -- supra --.
In column 2, line 66, change "tum" to read as -- tum --.
In column 3, line 3, change "turn" to read as -- tum- --.
In column 3, line 11, change "lurguin" to read as -- lurquin --.
In column 3, line 51, change "all" to read as -- al --.
In column 3, line 56, change "all" to read as -- al --.
In column 6, line 23, change "plassid" to read as -- plasmid --.
In column 6, line 26, change "EM" to read as -- mM --.
In column 6, line 28, change "MM" to read as -- mM --.
In column 7, line 33, change "subdlones" to read as -- subclones --.
In column 8, line 60, delete the period before "following".
In column 9, line 23, change "Biolocy" to read as -- Biology --.

UNITED STATES PATENT AND TRADEMARK OFFICE
CERTIFICATE OF CORRECTION

PATENT NO. : 5,925,729
DATED : July 20, 1999
INVENTOR(S) : Boon et al.

It is certified that error appears in the above-indentified patent and that said Letters Patent is hereby corrected as shown below:

In column 9, line 26, change "MRNA" to read as -- mRNA --.
In column 10, line 51, change "surra" to read as -- supra --.
In column 12, line 52, delete "20".
In column 13, line 14, change "uM" to read as -- mM --.
In column 13, line 17, change "zM" to read as -- mM --.
In column 13, line 60, change "Interested" to read as -- interest --.
In column 14, line 27, change "iN" to read as -- 1N --.
In column 18, line 63, change "MAGETRAS" to read as -- MAGETRAs --.
In column 19, line 62, change "other" to read as -- others --.
In column 21, line 66, change "gg" to read as -- $\mu$g --.
In column 24, line 14, change "surra" to read as -- supra --.

Signed and Sealed this

Twenty-second Day of May, 2001

Attest:

NICHOLAS P. GODICI

Attesting Officer    Acting Director of the United States Patent and Trademark Office